United States Patent
Seligmann et al.

(10) Patent No.: US 10,294,515 B2
(45) Date of Patent: May 21, 2019

(54) METHODS OF DETECTING GENE FUSIONS

(75) Inventors: Bruce Seligmann, Tucson, AZ (US);
BJ Kerns, Tucson, AZ (US); John Luecke, Tucson, AZ (US); Matt Rounseville, Tucson, AZ (US); Ihab Botros, Tucson, AZ (US); Mark Schwartz, Tucson, AZ (US)

(73) Assignee: HTG Molecular Diagnostics, Inc., Tucson, AZ (US)

(*) Notice: Subject to any disclaimer, the term of this patent is extended or adjusted under 35 U.S.C. 154(b) by 148 days.

(21) Appl. No.: 14/130,397

(22) PCT Filed: Dec. 7, 2011

(86) PCT No.: PCT/US2011/063803
§ 371 (c)(1),
(2), (4) Date: Dec. 31, 2013

(87) PCT Pub. No.: WO2013/006195
PCT Pub. Date: Jan. 10, 2013

(65) Prior Publication Data
US 2014/0120540 A1 May 1, 2014

Related U.S. Application Data

(60) Provisional application No. 61/504,040, filed on Jul. 1, 2011.

(51) Int. Cl.
*C12Q 1/68* (2018.01)
*C07H 21/04* (2006.01)
(Continued)

(52) U.S. Cl.
CPC ......... *C12Q 1/6813* (2013.01); *C12Q 1/6827* (2013.01); *C12Q 1/6886* (2013.01); *C12Q 2600/156* (2013.01)

(58) Field of Classification Search
None
See application file for complete search history.

(56) References Cited

U.S. PATENT DOCUMENTS 6,632,610 B2 * 10/2003 Thill ............... C12Q 1/6809
435/6.15
6,900,013 B1 5/2005 Wang et al.
(Continued)

FOREIGN PATENT DOCUMENTS

WO    WO 89/09285    10/1989
WO    WO 91/15600    10/1991
(Continued)

OTHER PUBLICATIONS

Clark et al. (Science, vol. 296, pp. 907-910, May 2002).*
(Continued)

*Primary Examiner* — Jeanine A Goldberg
(74) *Attorney, Agent, or Firm* — Klarquist Sparkman, LLP

(57) ABSTRACT

Disclosed herein are methods of detecting presence of a gene fusion in a sample from a subject. In some embodiments, the methods of detecting presence of a fusion gene in a sample from a subject utilize a fusion probe that spans the point of fusion between two nucleic acids or genes, and detecting the fusion probe after nuclease treatment. In other embodiments, the methods of detecting presence of a fusion gene in a sample from a subject utilize two or more probes that flank the point of fusion between two nucleic acids or genes, and detecting these probes after nuclease treatment. In additional embodiments, the methods can include determining the percentage of gene fusion in the sample relative to the first nucleic acid or the second nucleic acid.

19 Claims, 12 Drawing Sheets
Specification includes a Sequence Listing.

(51) Int. Cl.
*C12Q 1/6813* (2018.01)
*C12Q 1/6886* (2018.01)
*C12Q 1/6827* (2018.01)

(56) References Cited

U.S. PATENT DOCUMENTS

| | | | | |
|---|---|---|---|---|
| 7,034,144 | B2* | 4/2006 | van Donge | C12Q 1/6841 |
| | | | | 435/6.11 |
| 7,175,982 | B1* | 2/2007 | McCarthy | C12Q 1/6827 |
| | | | | 435/6.12 |
| 7,585,964 | B2* | 9/2009 | Palanisamy | C12Q 1/6841 |
| | | | | 435/6.11 |
| 8,163,477 | B2* | 4/2012 | Yu | C12Q 1/6834 |
| | | | | 435/6.1 |
| 2002/0132251 | A1 | 9/2002 | Shuber | |
| 2003/0190654 | A1 | 10/2003 | Heidenreich et al. | |
| 2004/0219565 | A1* | 11/2004 | Kauppinen | C07H 19/06 |
| | | | | 435/5 |
| 2006/0084105 | A1* | 4/2006 | Ares | C07H 21/04 |
| | | | | 435/6.1 |
| 2009/0048785 | A1* | 2/2009 | Katzir | G06K 9/00134 |
| | | | | 702/20 |
| 2009/0081222 | A1* | 3/2009 | Wong | C07K 14/71 |
| | | | | 424/138.1 |
| 2009/0136918 | A1* | 5/2009 | Newkirk | C12Q 1/6827 |
| | | | | 435/6.11 |
| 2012/0052498 | A1* | 3/2012 | Nguyen | C12Q 1/682 |
| | | | | 435/6.11 |
| 2012/0215459 | A1* | 8/2012 | Stef | C12Q 1/6837 |
| | | | | 702/19 |
| 2013/0023433 | A1* | 1/2013 | Luo | C12Q 1/6841 |
| | | | | 506/9 |

FOREIGN PATENT DOCUMENTS

| | | |
|---|---|---|
| WO | WO 03/002750 | 1/2003 |
| WO | WO 2008/121927 | 10/2008 |
| WO | WO 2009/102446 | 8/2009 |
| WO | WO 2011/043220 | 4/2011 |

OTHER PUBLICATIONS

Ladanyi et al. (Genes, Chromosomes and Cancer, vol. 15, pp. 173-177, 1996).*
Goldrick et al., "RNA analysis by nuclease protection," *Current Protocols in Neuroscience*, Ch. 5.1, 2003 (30 pages).
Lira et al., "Multiplexed Gene Expression and Fusion Transcript Analysis to Detect ALK Fusions in Lung Cancer," *J. Mol. Diagnostics* vol. 15, No. 1, pp. 51-61, 2013.
Shtivelman et al., "bcr-abl RNA in Patients with Chronic Myelogenous Leukemia," *Blood*, vol. 69, pp. 971-973, 1987.
Van Sant, "qNPA Measurement of Fusion Genes," *ADAPT Congress 2011*, Sep. 7-9, 2011 (28 pages).
Voz et al., "The Recurrent Translocation t(5;8)(p13;q12) in Pleomorphic Adenomas Results in Upregulation of PLAG1 Gene Expression Under Control of the LIFR Promoter," *Oncogene*, vol. 16, pp. 1409-1416, 1998.
Wei et al., "A 3 kb Sequence from the Mouse Cellular Retinoic-Acid-Binding Protein Gene Upstream Region Mediates Spatial and Temporal LacZ Expression in Transgenic Mouse Embryos," *Development*, vol. 112, pp. 847-854, 1991.
Young et al., "A Fused Mitochondrial Gene Associated with Cytoplasmic Male Sterility is Developmentally Regulated," *Cell*, vol. 50, pp. 41-49, 1987.
Clark et al, "Expression of a Distinctive BCR-ABL Oncogene in Ph[1]-Positive Acute Lymphocytic Leukemia (ALL)," *Science*, vol. 239, pp. 775-777, 1988.
Petrovic et al., "The Ig Heavy Chain 3' End Confers a Post-transcriptional Processing Advantage to Bcl-2-IgH Fusion RNA in t(14; 18) Lymphoma," *Blood*, vol. 91, No. 10, pp. 3952-3961, 1998.
Supplementary European Search Report for European Patent Application No. 11868918.1, dated May 14, 2014 (9 pages).

* cited by examiner

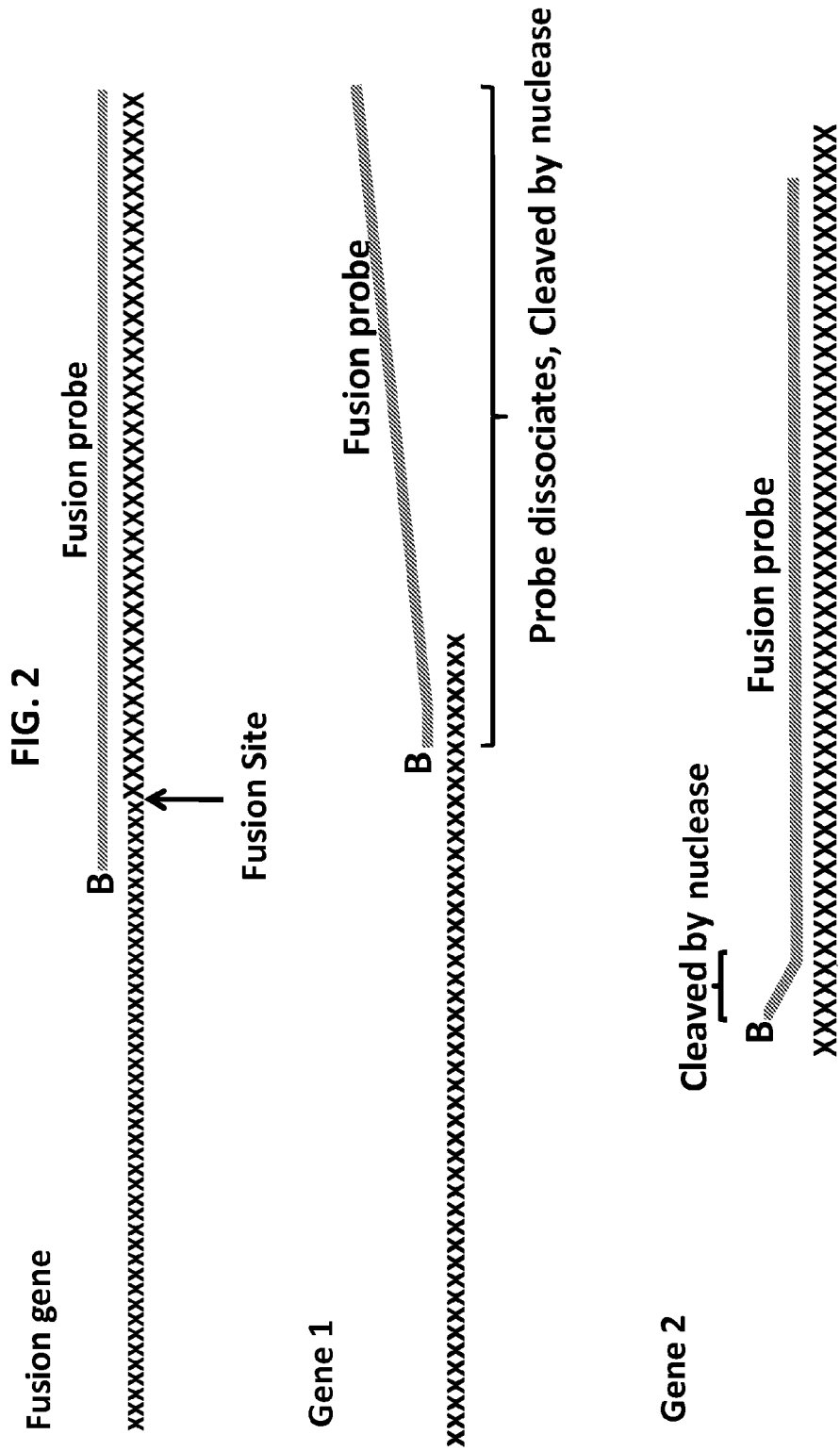

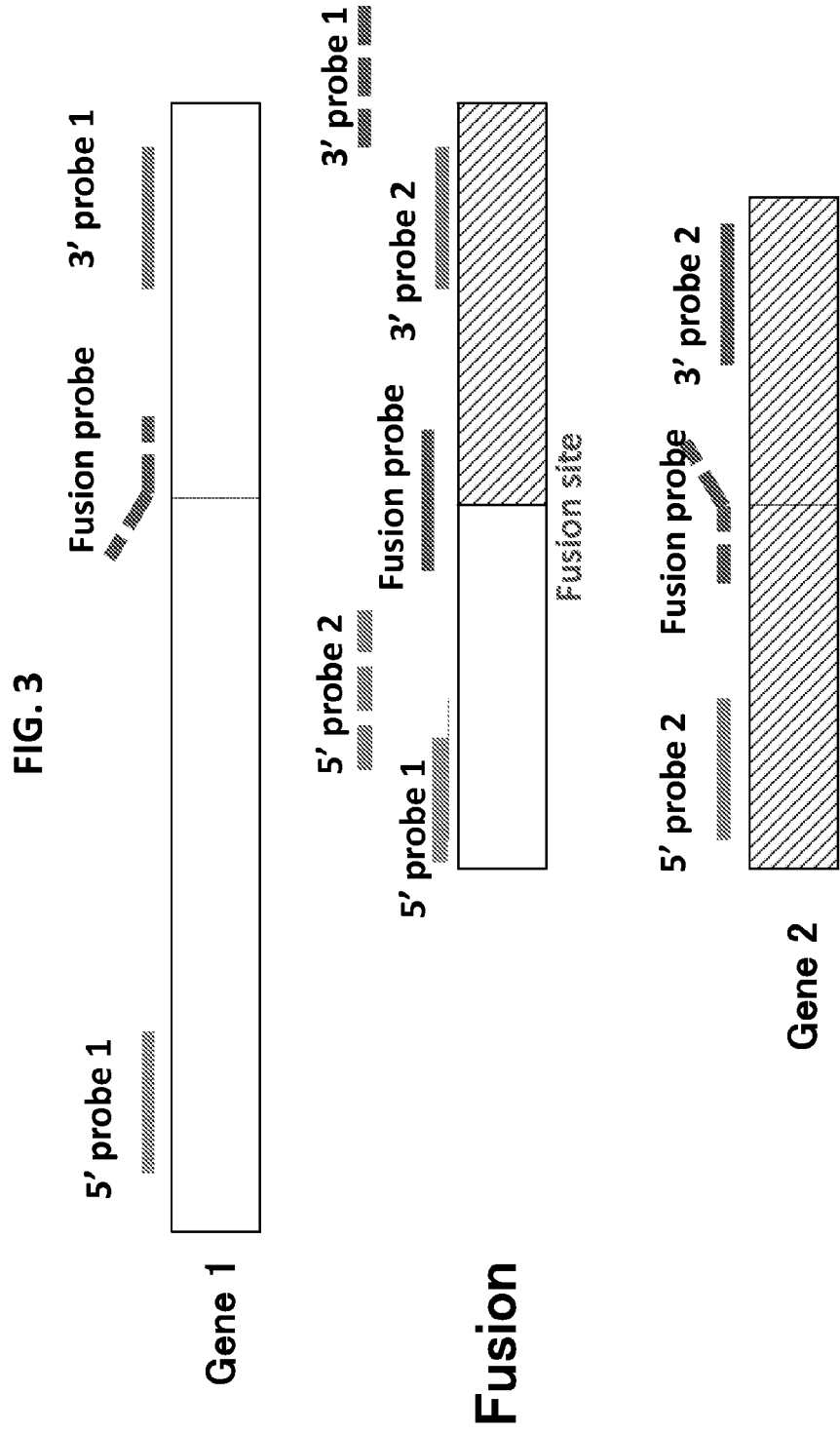

FIG. 4

BCR/ABL Fusion Test

| | | E1A2 | E6A2 | E12A2 | E13A2 | E14A2 | E19A2 | E20A2 | E1A3 | E6A3 | E12A3 | E13A3 | E14A3 | E19A3 | E20A3 |
|---|---|---|---|---|---|---|---|---|---|---|---|---|---|---|---|
| | | | | | | | *In Vitro* Transcript (Sample) | | | | | | | | |
| Array Target | E1A2 | Yes | No | No | No | No | No | No | No | No | No | No | No | No | No |
| | E6A2 | No | Yes | No | No | No | No | No | No | No | No | No | No | No | No |
| | E12A2 | No | No | Yes | No | No | No | No | No | No | No | No | No | No | No |
| | E13A2 | No | No | No | Yes | No | No | No | No | No | No | No | No | No | No |
| | E14A2 | No | No | No | No | Yes | No | No | No | No | No | No | No | No | No |
| | E19A2 | No | No | No | No | No | Yes | No | No | No | No | No | No | No | No |
| | E20A2 | No | No | No | No | No | No | Yes | No | No | No | No | No | No | No |
| | E1A3 | No | No | No | No | No | No | No | Yes | No | No | No | No | No | No |
| | E6A3 | No | No | No | No | No | No | No | No | Yes | No | No | No | No | No |
| | E12A3 | No | No | No | No | No | No | No | No | No | Yes | No | No | No | No |
| | E13A3 | No | No | No | No | No | No | No | No | No | No | Yes | No | No | No |
| | E14A3 | No | No | No | No | No | No | No | No | No | No | No | Yes | No | No |
| | E19A3 | No | No | No | No | No | No | No | No | No | No | No | No | Yes | No |
| | E20A3 | No | No | No | No | No | No | No | No | No | No | No | No | No | Yes* |

METHODS OF DETECTING GENE FUSIONS

CROSS REFERENCE TO RELATED APPLICATION

This is the U.S. National Stage of International Application No. PCT/US2011/063803, filed Dec. 7, 2011, which was published in English under PCT Article 21(2), which in turn claims the benefit of U.S. Provisional Application No. 61/504,040, filed Jul. 1, 2011, which is incorporated herein in its entirety.

FIELD

This disclosure relates to methods of detecting gene fusions, particularly oncogenic gene fusions.

BACKGROUND

Many cancers are characterized by disruptions in cellular signaling pathways that lead to aberrant control of cellular processes, or to uncontrolled growth and proliferation of cells. These disruptions are often caused by genetic changes (also called mutations) that affect the activity of particular signaling proteins. A fusion gene is one type of mutation which is a hybrid gene formed from two previously separate genes or from previously non-contiguous regions of the same gene. It can occur, for example, as the result of a translocation, interstitial deletion, or chromosomal inversion.

Among other known examples, tyrosine kinase genes, which encode important enzymes directly regulating cell growth, have been reported to contain oncogenic mutations. Kinase activity can be activated, for example, by substitution or deletion in amino acid sequences and thereby bring about carcinogenesis or contribute to aggressive versus less aggressive cancers, or lead to a propensity for metastasis, or cause drug sensitivity or drug resistance. Although there are many examples, the BCR-ABL gene fusion is one that has long been associated with cancer; in particular, chronic myelogenous leukemia (CML) and in some cases acute myelogenous leukemia (AML) or acute lymphoblastic leukemia (ALL). Other examples include gene rearrangements involving EML4/ALK (e.g., lung cancer), TMPRSS2/ERG (e.g., prostate cancer), IgH/MYC (e.g., Burkitt lymphoma), MYB/NFIB (e.g., carcinomas of the breast and head and neck), TMPRSS2/ETV4 (e.g., prostate cancer), EWSR1/FLI1 (e.g., Ewing sarcoma), and many others known to those of skill in the art or yet to be discovered.

In the context of neoplastic transformation, it is known that some genes are highly promiscuous in that they may recombine with many different partners, for example, within the same tumor entities, e.g., MLL in acute leukemias (Collins and Rabbitts, *Trends in Molecular Medicine*, 8(9): 436-442 2002), EWSR1 in bone and soft tissue tumors (Helman and Meltzer, *Nature Reviews Cancer*, 3(9): 685-694, 2003), and RET in thyroid carcinomas (Pierotti, *Nature Reviews Cancer*, 1(3): 245-250, 2001). However, the same fusion gene may also give rise to tumors of totally different derivations, and one particular fusion gene, ETV6-NTRK3, has been described in cancers as diverse as acute myeloid leukemia, infantile fibrosarcoma, mesoblastic nephroma, and breast carcinoma (Tognon et al., *Cancer Cell*, 2(5): 367-376, 2002). There are also several examples where seemingly identical chromosomal aberrations produce different fusion genes. One of the most common translocations in pre-B acute lymphoblastic leukemia, t(1;19)(q23;p13) leading to a TCF3/PBX1 fusion, may result in a chimeric transcript consisting of two entirely different genes, MEF2D in 1q23 and DAZAP1 in 19q13 (Yuki et al., *Cancer Science*, 95 (6):503-507, 2004).

Gene fusions can be diagnostic markers or therapeutic targets, as well as useful for predicting patient prognosis and/or response to drugs. Further, it is clear that multiple fusions may arise in the same tumor or subject and/or that each subject may have medically relevant gene fusions that differ from other afflicted subjects. Accordingly, new technologies for detecting gene fusions are critically important to advance science and medicine.

SUMMARY

Disclosed herein are methods of detecting presence of a gene fusion (such as an oncogenic gene fusion) in a sample from a subject. The disclosed methods can be used to detect known gene fusions (such as a known gene translocation, interstitial deletion, or inversion) and in some examples, can also be used to detect previously unknown gene fusions, for example a fusion between two genes at a previously unidentified fusion point, or a fusion between two genes previously unknown to participate in a gene fusion. The methods are highly sensitive and specific, optionally can be used to quantify detected gene fusions, and can be used to detect a gene fusion in any nucleic acid molecule, such as DNA or RNA. The disclosed methods are also amenable to multiplexing, so as to detect multiple gene fusions in a sample from a subject, or to detect the same set of gene fusions (or set of genes, including some gene fusions) in samples from multiple subjects.

The foregoing and other features of the disclosure will become more apparent from the following detailed description, which proceeds with reference to the accompanying figures.

BRIEF DESCRIPTION OF THE DRAWINGS

FIG. 2 is a schematic diagram showing exemplary wild-type genes (Genes 1 and 2) and a fusion gene and an exemplary direct-labeled fusion probe having a four nucleotide overlap with the 5' portion of the fusion gene. The label (biotin in this example) is located at the 5' end of the probe. When the gene fusion is present in a sample, the fusion probe hybridizes and the label is detected following nuclease treatment (top panel). The fusion probe does not hybridize to Gene 1 and is hydrolyzed by the nuclease treatment (middle panel). The fusion probe hybridizes to Gene 2; however the 5' end including the label does not hybridize and is cleaved by the nuclease treatment (bottom panel). Therefore, the labeled probe is only detected in samples where the gene fusion is present.

FIG. 3 is a schematic diagram showing exemplary full-length wild type genes (Genes 1 and 2) and a fusion gene and exemplary flanking probes and an exemplary fusion probe. The fusion gene includes a 5' portion of Gene 1 and a 3' portion of Gene 2. The flanking 5' probe 1 and 3' probe 1 hybridize to full-length Gene 1 and are detected following nuclease treatment. The flanking 5' probe 1 also hybridizes to the fusion gene and is detected following nuclease treatment; however the flanking 3' probe 1 does not hybridize to the fusion gene and is hydrolyzed by nuclease treatment. The flanking 5' probe 2 and 3' probe 2 can optionally be included in the assay; these hybridize to the full-length gene 2 and are detected following nuclease treatment. The 3' probe 2 also hybridizes to the fusion gene and is detected following nuclease treatment; however the flanking 5' probe 2 does not hybridize to the fusion gene and is hydrolyzed by the nuclease treatment (dotted line). A fusion probe spanning the fusion point can also optionally be included in the assay. When the gene fusion is present in a sample, the fusion probe hybridizes and is detected following nuclease treatment (solid line). When the gene fusion is not present in a sample, the fusion probe only partially hybridizes to Genes 1 and 2 and at least the non-hybridized portion is hydrolyzed by the nuclease treatment (dotted lines).

FIG. 4 is a diagram showing a checkerboard assay detecting Bcr-Abl in vitro transcribed fusion targets with Bcr-Abl fusion probes (Table 4, below). "Yes" indicates detectable signal, "No" indicates lack of detectable signal.

Figure 5A:
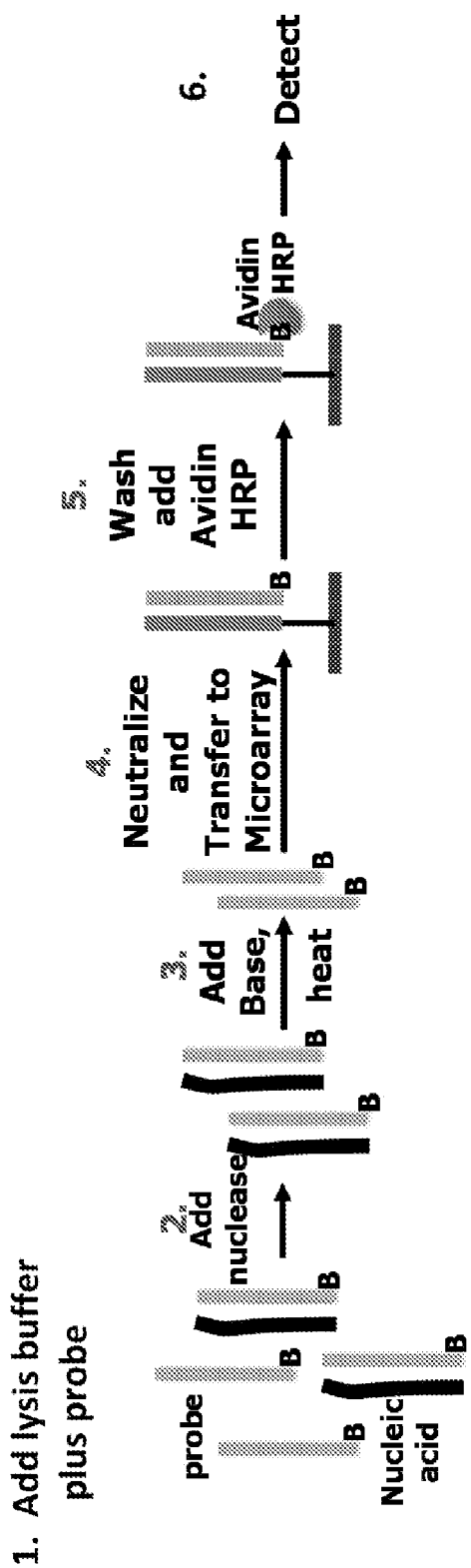
Figure 5B:
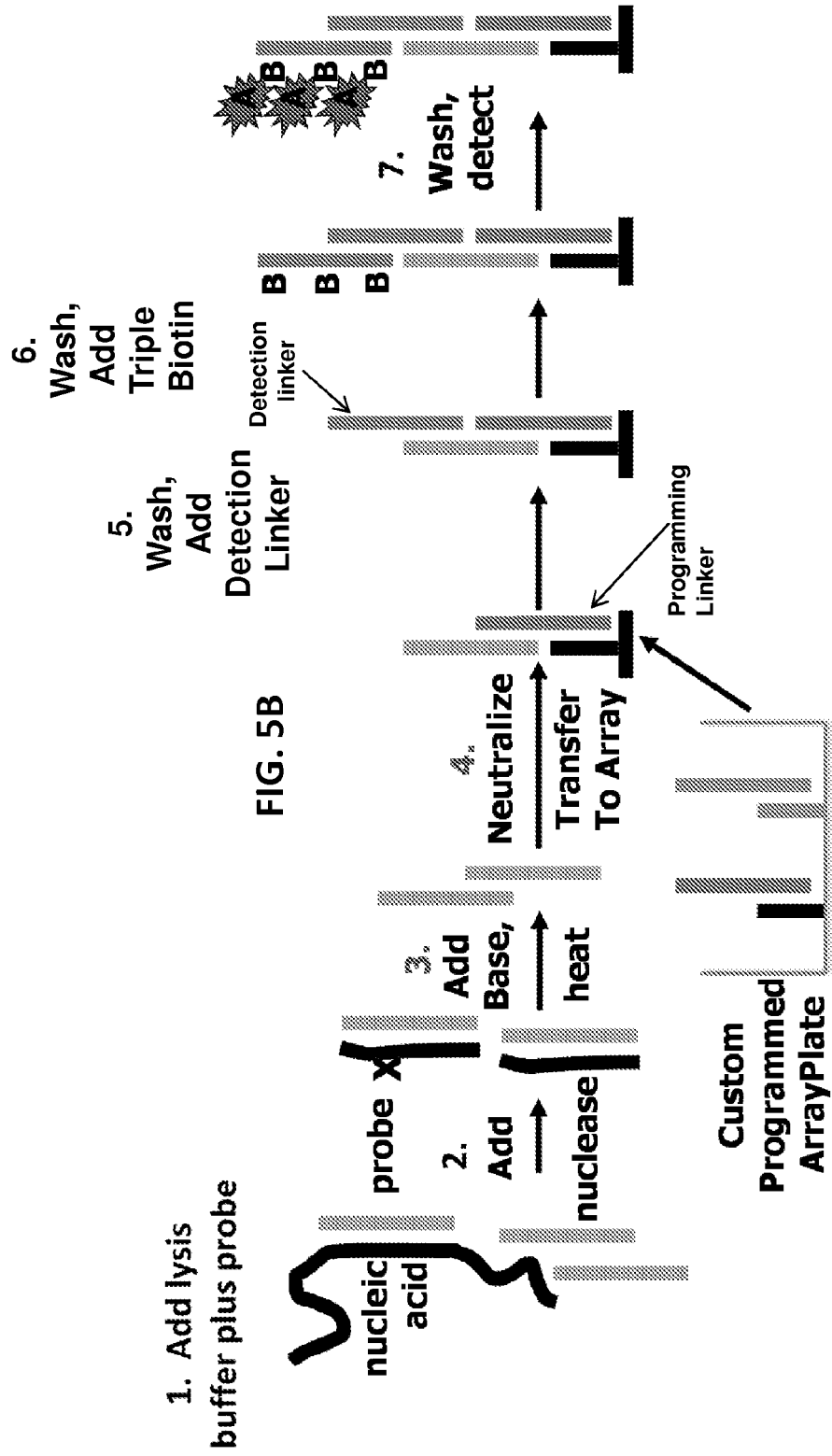
Figure 6A:
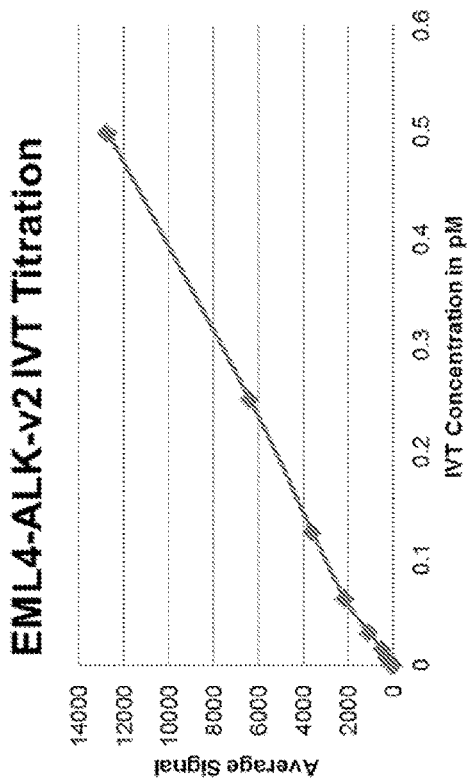
Figure 6B:
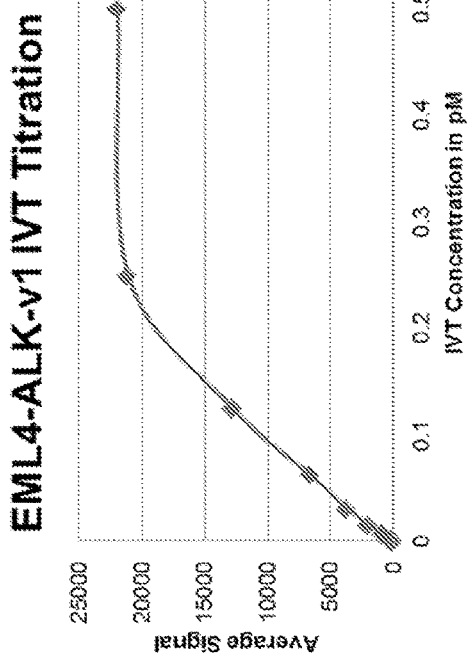
Figures 6C, 6D:
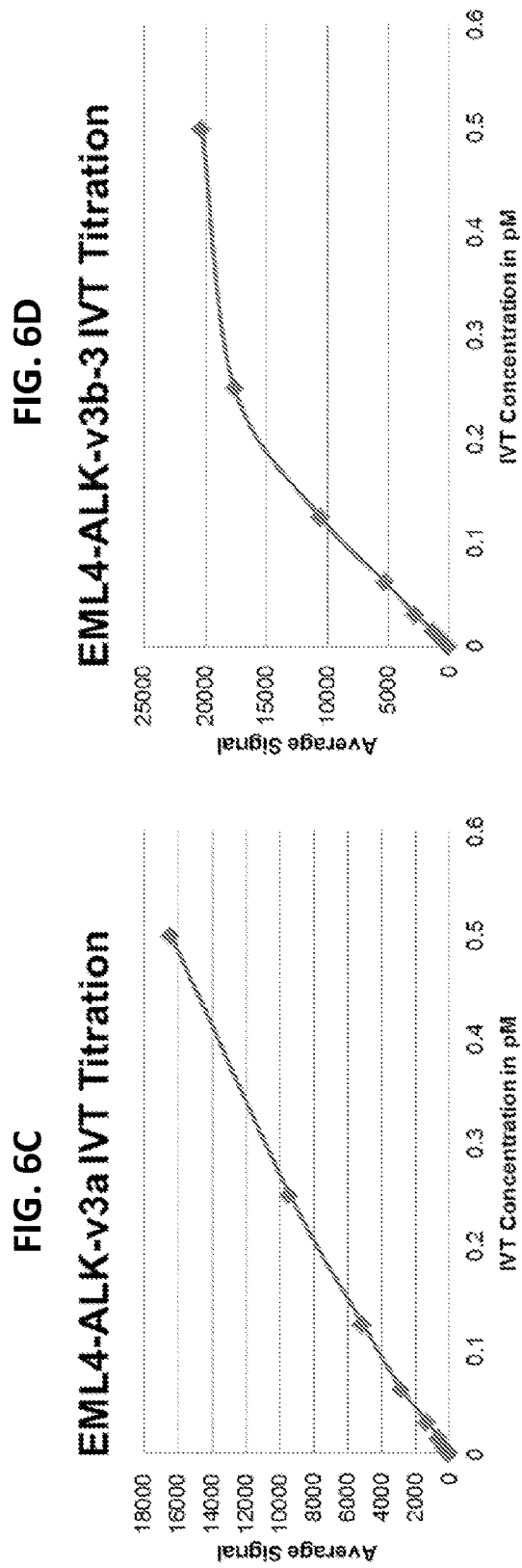
Figure 6F:
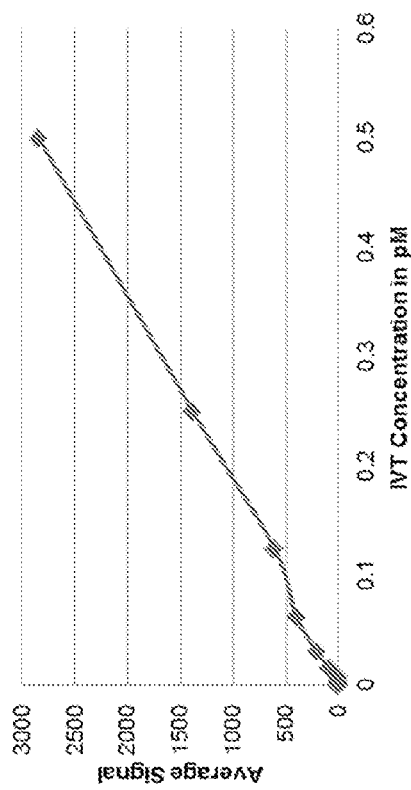
Figure 6E:
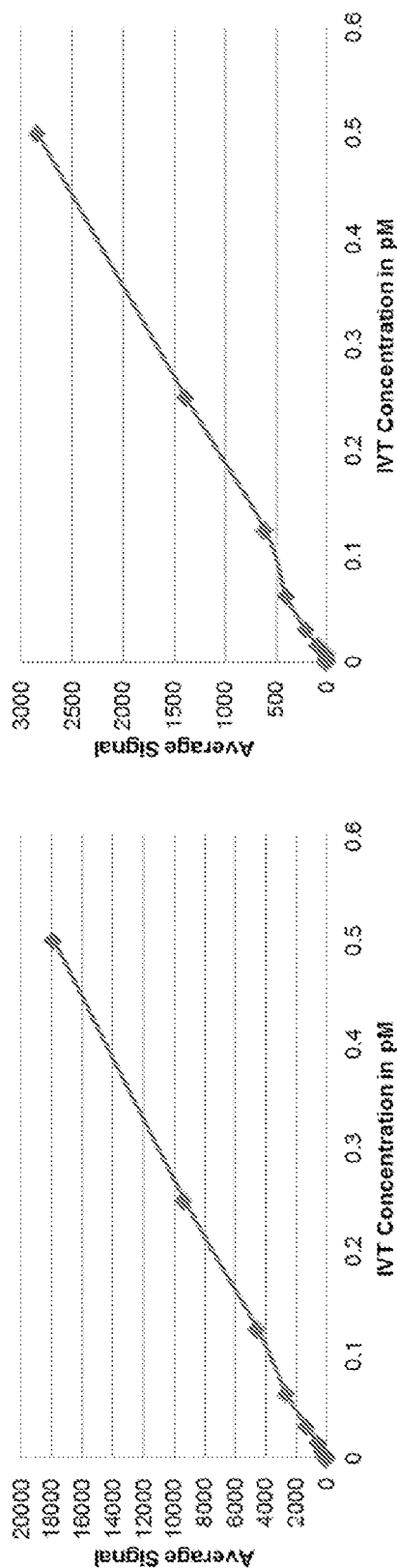
Figure 6G:
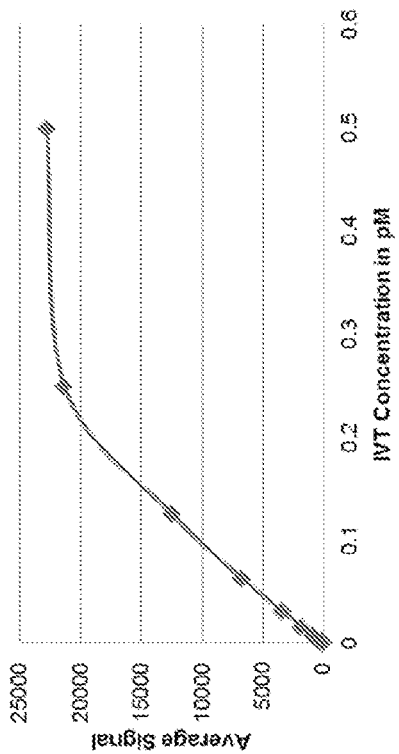
Figure 6H:
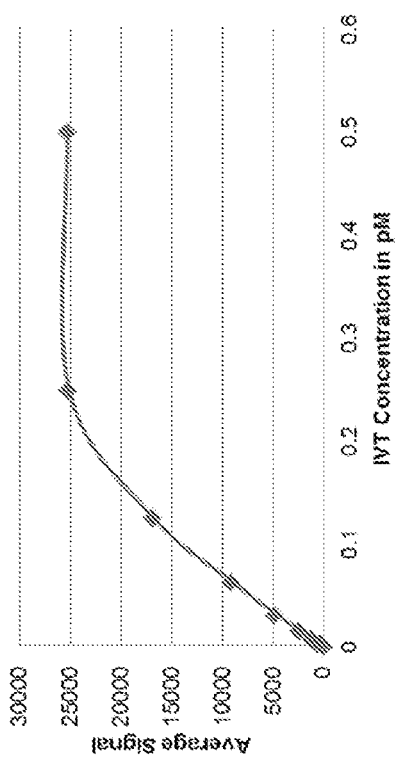

FIGS. 5A and B are schematic diagrams of exemplary methods of capturing one or more fusion probes and/or flanking probes on an array to detect the presence of one or more gene fusions in a single sample. FIG. 5A shows hybridization of a detectably labeled fusion or flanking probe (biotinylated in this case) with a target nucleic acid (step 1), nuclease treatment (step 2), dissociation of the probe from the target nucleic acid (step 3), hybridization of the detectably labeled probe on a microarray including a nucleic acid complementary to the probe (step 4), and detection of the labeled probe (steps 5 and 6). FIG. 5B shows hybridization of a fusion or flanking probe with a target nucleic acid (step 1), nuclease treatment (step 2), dissociation of the probe from the target nucleic acid (step 3), hybridization of the probe on a microarray including a programming linker which is complementary to a portion of the probe (step 4), hybridization with a detection linker, a portion of which is complementary to a different portion of the probe (step 5), hybridization with a detectably labeled nucleic acid (biotinylated in this case) which is complementary to a different portion of the detection linker (step 6), and detection of the labeled nucleic acid (step 7).

FIGS. 6A-H are a series of panels showing titration of fusion probes for EML4-ALK-v1 (FIG. 6A), EML4-ALK-v2 (FIG. 6B), EML4-ALK-v3a (FIG. 6C), EML4-ALK-v3b-3 (FIG. 6D), EML4-ALK-v4 (FIG. 6E), EML4-ALK-v5a (FIG. 6F), EML4-ALK-v5b-3 (FIG. 6G), and EML4-ALK-v6 (FIG. 6H) with increasing amounts of the corresponding EML4-ALK in vitro transcribed (IVT) RNAs.

Figure 7A:
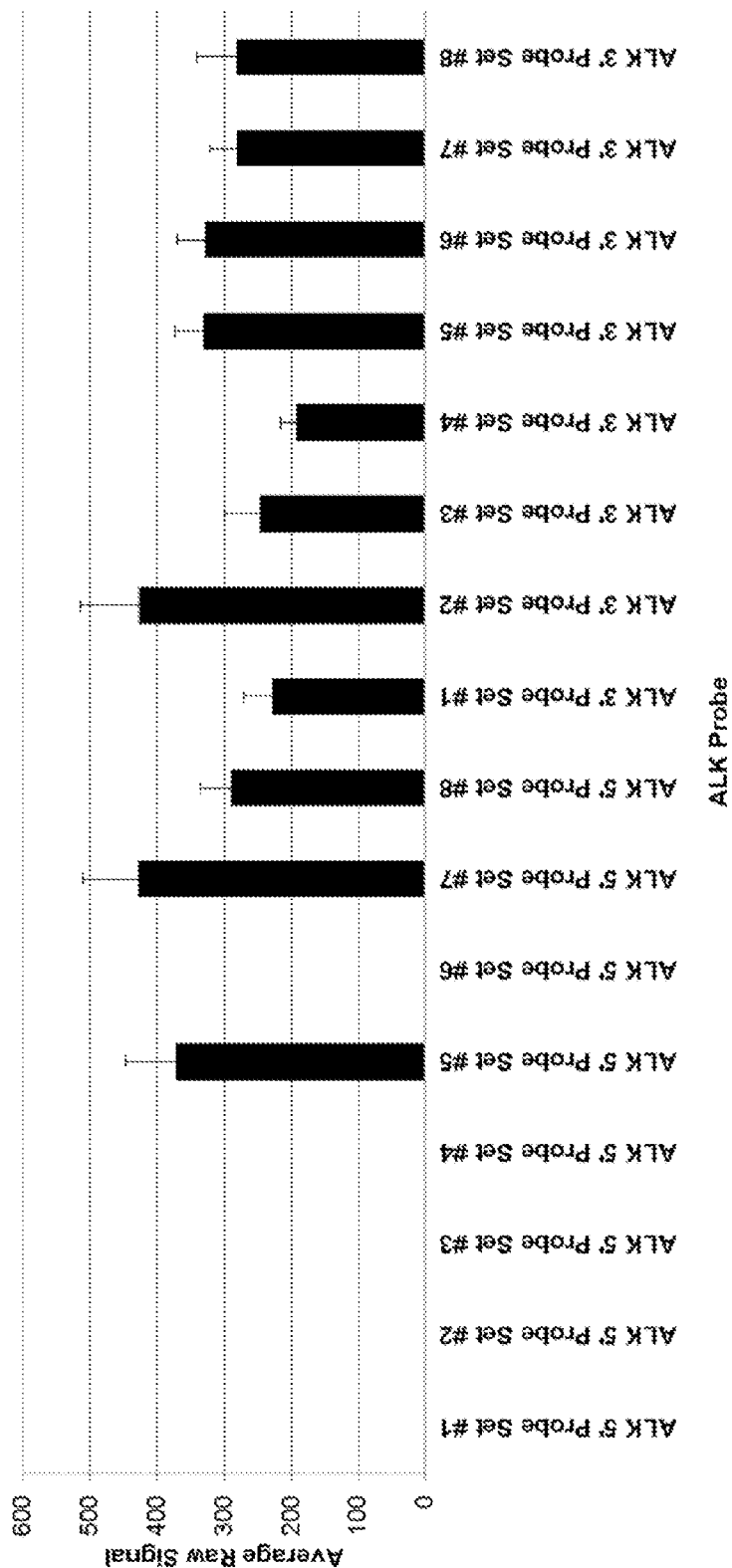
Figure 7B:
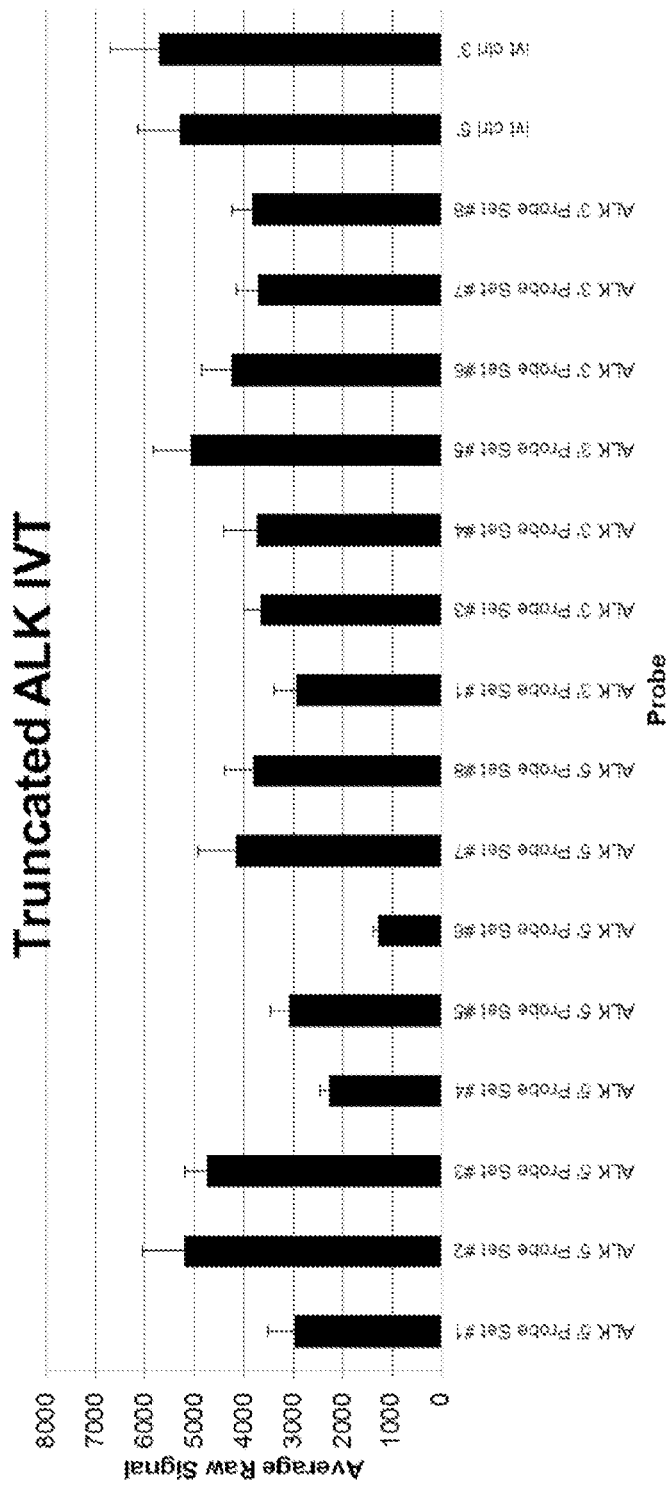

FIGS. 7A and B are graphs showing signal obtained using the identified ALK flanking probes with full-length ALK IVT (FIG. 7A) or a truncated ALK IVT (FIG. 7B).

SEQUENCE LISTING

Any nucleic acid and amino acid sequences listed herein or in the accompanying sequence listing are shown using standard letter abbreviations for nucleotide bases, and three letter code for amino acids, as defined in 37 C.F.R. 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Dec. 27, 2013, and is 40,290 bytes, which is incorporated by reference herein.

SEQ ID NOs: 1-32 are exemplary fusion probe nucleic acid sequences.

SEQ ID NOs: 33-132 are exemplary flanking probe nucleic acid sequences.

SEQ ID NOs: 133-146 are Bcr-Abl fusion probe nucleic acid sequences.

SEQ ID NOs: 147-160 are Bcr-Abl programming linker nucleic acid sequences.

SEQ ID NOs: 161-174 are Bcr-Abl detection linker nucleic acid sequences.

SEQ ID NO: 175 is an exemplary Bcr-Abl E1A2 fusion region nucleic acid sequence.

SEQ ID NO: 176 is an exemplary Bcr-Abl "short overlap" fusion probe nucleic acid sequence.

SEQ ID NOs: 177-184 are exemplary EML4-ALK fusion probe target nucleic acid sequences.

SEQ ID NOs: 185-192 are exemplary 5'-ALK flanking probe target nucleic acid sequences.

SEQ ID NOs: 193-200 are exemplary 3'-ALK flanking probe target nucleic acid sequences.

DETAILED DESCRIPTION

I. Introduction

Disclosed herein are methods of detecting one or more gene fusions in a biological sample. In some embodiments, the methods of detecting presence of a fusion gene in a sample from a subject utilize a fusion probe that spans the point of fusion between two nucleic acids or genes. In particular embodiments, the methods include detecting presence of a fusion gene mRNA in a sample from a subject. The methods can include contacting a sample from a subject (such as a sample including nucleic acids) with a fusion probe. The fusion probe includes a 5' portion complementary to a first nucleic acid and a 3' portion complementary to a second nucleic acid, wherein the fusion probe spans a fusion point of the first nucleic acid and the second nucleic acid. The fusion probe is incubated with the sample under conditions sufficient for the fusion probe to specifically hybridize to a gene fusion. The sample is contacted with a nuclease specific for single-stranded nucleic acids (for example, S1 nuclease), and the presence of the fusion probe is detected. The fusion gene is identified as present in the sample when the fusion probe is detected.

In some examples, the fusion probe includes a detectable label (such as biotin or horseradish peroxidase) and detecting the presence of the fusion probe includes detecting the detectable label. In other examples, the fusion probe is detected indirectly, for example by hybridization with a labeled nucleic acid complementary to all or a portion of the fusion probe (e.g., a "programming linker"). In some examples, the fusion probe is detected using a microarray, for example, a microarray including a nucleic acid that is complementary to the fusion probe (see, for example, FIG. 5A). In other examples, the fusion probe is detected using a microarray including a programming linker complementary to a portion of the fusion probe and subsequently incubating with a detection linker, a portion of which is complementary to a separate portion of the fusion probe. The detection linker can be detectably labeled, or a separate portion of the detection linker can be complementary to an additional nucleic acid including a detectable label (such as biotin or horseradish peroxidase). See, for example, FIG. 5B.

In some embodiments, the methods include contacting a sample from a subject (such as a sample including nucleic acids) with a fusion probe. The fusion probe includes a 5' portion complementary to a first nucleic acid and a 3' portion complementary to a second nucleic acid, wherein the fusion probe spans a fusion point of the first nucleic acid and the second nucleic acid. The fusion probe is incubated with the sample under conditions sufficient for the fusion probe to specifically hybridize to a gene fusion. The sample is contacted with a nuclease specific for single-stranded nucleic acids (for example, S1 nuclease) and the sample is then contacted with a surface including at least two spatially discrete regions, wherein at least one region includes an anchor in association with a bifunctional linker under conditions sufficient for the fusion probe to specifically bind (e.g., hybridize to) the bifunctional linker and detecting the hybridized fusion probe. The bifunctional linker has a first portion specific for (e.g., complementary to) the anchor and a second portion specific for (e.g., complementary to) the fusion probe. The gene fusion is identified as present in the sample when the fusion probe is detected.

In some examples, the methods include detecting presence of more than one gene fusion in a sample from the subject. The methods can include contacting a sample from a subject (such as a sample including nucleic acids) with at least two fusion probes. Each fusion probe includes a 5' portion complementary to a first nucleic acid and a 3' portion complementary to a second nucleic acid, wherein the fusion probe spans a fusion point of the first nucleic acid and the second nucleic acid of a particular (different) gene fusion. The at least two fusion probes are incubated with the sample under conditions sufficient for the fusion probes to specifically hybridize to the gene fusion. The sample is contacted with a nuclease specific for single-stranded nucleic acids (for example, S1 nuclease) and the sample is then contacted with a surface including at least two spatially discrete regions including at least one anchor, wherein each anchor is in association with a bifunctional linker which has a first portion specific for (e.g., complementary to) the anchor and a second portion specific for (e.g., complementary to) one of the at least two fusion probes, under conditions sufficient for the fusion probes to bind (e.g., hybridize to) the bifunctional linker, detecting the hybridized fusion probes, and identifying presence of the gene fusion by the spatially distinct region to which the fusion probe is bound.

In some embodiments, fusion probes of use in the disclosed methods are about 10-200 nucleotides in length. In some examples, the fusion probe includes approximately equal numbers of nucleotides from each of the first and second nucleic acids. In other examples, the fusion probe includes a small number of nucleotides from one of the two nucleic acids and a greater number of nucleotides from the other nucleic acid. For example, the 5' portion of the probe can be about 1-10 nucleotides in length and the 3' portion of the probe can be about 10 nucleotides or more in length or the 5' portion of the probe can be about 10 nucleotides or more in length and the 3' portion of the probe can be about 1-10 nucleotides in length.

In other embodiments, the methods of detecting presence of a fusion gene in a sample from a subject utilize two or more probes that flank the point of fusion between two nucleic acids or genes. The methods can include contacting a sample from a subject with a first probe complementary to a first nucleic acid 5' to a fusion point between the first nucleic acid and a second nucleic acid under conditions sufficient for the first probe to specifically hybridize to the first nucleic acid and contacting the sample with a second probe complementary to the first nucleic acid 3' to the fusion point between the first and second nucleic acids under conditions sufficient for the second probe to specifically hybridize to the first nucleic acid. The sample is contacted with a nuclease specific for single-stranded nucleic acids (for example, S1 nuclease), the presence of the first probe and the second probe is detected, and a ratio of the first probe to the second probe is determined. The fusion gene is identified as present in the sample when the ratio of the first probe to the second probe is different from one (for example, statistically significantly different from one). In some examples, the gene fusion is detected and does not include a 3' portion of the first nucleic acid if the ratio of the first probe to the second probe is greater than one (for example, statistically significantly greater than one). In other examples, the gene fusion is detected and does not include a 5' portion of the first nucleic acid if the ratio of the first probe to the second probe is less than one (for example, statistically significantly less than one). In some examples, the first probe and the second probe are each about 10-200 nucleic acids in length.

In some examples, the first and/or second probes (e.g., the flanking probes) include a detectable label (such as biotin or horseradish peroxidase) and detecting the presence of the probe(s) includes detecting the detectable label. In some examples, the flanking probes are labeled with the same detectable label. In other examples, the flanking probes are labeled with different detectable labels. In other examples, the flanking probes are detected indirectly, for example by hybridization with a labeled nucleic acid complementary to all or a portion of the fusion probe (e.g., a "programming linker"). In some examples, the flanking probes are detected using a microarray, for example, a microarray including nucleic acids that are complementary to the flanking probes (see, for example, FIG. 5A). In other examples, the flanking probes are detected using a microarray including programming linkers complementary to a portion of each of the flanking probes and subsequently incubating with detection linkers, a portion of which is complementary to a separate portion of the flanking probes. The detection linkers can be detectably labeled, or a separate portion of the detection linkers are complementary to additional nucleic acids including a detectable label (such as biotin or horseradish peroxidase). See, for example, FIG. 5B.

In additional embodiments, the methods include determining the percentage of gene fusion in the sample relative to the first nucleic acid or the second nucleic acid. These methods further include contacting the sample with a fusion probe that includes a 5' portion complementary to a first nucleic acid and a 3' portion complementary to a second nucleic acid, wherein the fusion probe spans a fusion point of the first nucleic acid and the second nucleic acid, under conditions sufficient for the fusion probe to specifically hybridize to a gene fusion, in addition to contacting the sample with the first probe and the second probe as above. The methods can further include detecting the presence of the fusion probe and determining a ratio of the fusion probe to the first probe and/or a ratio of the fusion probe to the second probe.

In other embodiments, the methods include contacting a sample from a subject (such as a sample including nucleic acids) with two or more probes that flank the point of fusion between two nucleic acids or genes. The methods can include contacting a sample from a subject with a first probe complementary to a first nucleic acid 5' to a fusion point between the first nucleic acid and a second nucleic acid under conditions sufficient for the first probe to specifically hybridize to the first nucleic acid and contacting the sample with a second probe complementary to the first nucleic acid 3' to the fusion point between the first and second nucleic acids under conditions sufficient for the second probe to specifically hybridize to the first nucleic acid. The sample is contacted with a nuclease specific for single-stranded nucleic acids (for example, S1 nuclease) and the sample is then contacted with a surface including at least two spatially discrete regions including at least one anchor, wherein each anchor is in association with a bifunctional linker which has a first portion specific for (e.g., complementary to) the anchor and a second portion specific for (e.g., complementary to) one of the at least flanking probes, under conditions sufficient for the flanking probes to bind (e.g., hybridize to) the bifunctional linker, detecting the hybridized flanking probes, and determining a ratio of the first probe to the second probe. The gene fusion is identified as present in the sample when the ratio of the first probe to the second probe is different from one (for example, statistically significantly different from one).

In some examples, a nuclease protection step can reduce the need for extensive handling of nucleic acids, particularly RNA, which can be sensitive to degradation by contaminating nucleases and thus difficult to work with. In addition, embodiments in which nucleic acid purification (before or after probe hybridization) is not required decrease interassay variability introduced by nucleic acid extraction steps. In addition, lysis-only embodiments permit the ability to measure both soluble nucleic acids as well as cross-linked nucleic acids (for example in FFPE sections).

Nuclease protection of a sample can allow for greater sensitivity and reproducibility in an assay. In some embodiments, the methods result in decreased background, for example, because nuclease treatment destroys most non-specifically hybridized nucleic acids. Thus, the disclosed assays can be sensitive enough such that amplification of the gene fusion is not necessary in order to detect a signal. Particular method embodiments specifically do not include an amplification (e.g., PCR amplification) step. This reduces drawbacks of an amplification step, such as sequence-specific artifacts or bias, limited dynamic range, and the necessity for using purified and intact nucleic acids. The increased sensitivity of the disclosed methods allow for multiple assays to be performed on a single sample (for example, a single FFPE section can be divided into multiple tests). Furthermore, the increased sensitivity of the assay allows for single copy gene detection in as few as 1000 cells.

Finally, the disclosed methods are amenable to multiplexing, for example, using a microarray. Particular microarray embodiments are discussed in Section V, below. This allows screening or detection of multiple gene fusions simultaneously (such as detecting the same fusion in many samples, or detecting multiple different gene fusions in a single sample), for example at least 10, at least 25, at least 40, at least 50, at least 100, at least 200, at least 300, at least 400, at least 500, at least 750, at least 1000, or more gene fusions in a single assay. The multiplex microarray embodiment results in capture of fusion probes at spatially distinct locations, therefore the fusion probes can be detected using the same detectable label and distinguished based on their position in the microarray.

II. Terms

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, and Proteomics*, 2nd Edition, 2003 (ISBN: 0-471-26821-6).

The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

All publications, patent applications, patents, and other references mentioned herein are incorporated by reference in their entirety for all purposes. All sequences associated with the GenBank Accession Nos. mentioned herein are incorporated by reference in their entirety as were present on Jun. 29, 2011, to the extent permissible by applicable rules and/or law. In case of conflict, the present specification, including explanations of terms, will control.

Suitable methods and materials to practice or test the disclosed technology are described below; nevertheless, methods and materials similar or equivalent to those described herein can be used. The materials, methods, and examples are illustrative only and not intended to be limiting.

To facilitate review of the various embodiments of this disclosure, the following explanations of specific terms are provided:

Complementary: Ability to from base pairs between nucleic acids. Oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acids or two distinct regions of the same nucleic acid.

"Specifically hybridizable" and "specifically complementary" are terms that indicate a sufficient degree of complementarity such that stable and specific binding occurs between the probe (or its analog) and the nucleic acid target (e.g., DNA or RNA). The probe or analog may, but need not have 100% complementarity to its target sequence to be specifically hybridizable. A probe or analog is specifically hybridizable when there is a sufficient degree of complementarity to avoid non-specific binding of the probe or analog to non-target sequences under conditions where specific binding is desired, for example in the methods disclosed herein. Such binding is referred to as specific hybridization.

Contact: Placement in direct physical association; includes both in solid and liquid form. For example, contacting can occur in vitro with a nucleic acid probe and biological sample in solution or on a surface.

Detect: To determine if an agent (such as a signal, particular nucleotide, amino acid, nucleic acid molecule, and/or organism) is present or absent, for example a gene fusion nucleic acid. In some examples, this can further include quantification. For example, use of the disclosed methods and probes in particular examples permits detection of a gene fusion in a sample.

Detectable label: A compound or composition that is conjugated directly or indirectly to another molecule (such as a nucleic acid molecule, for example a fusion probe, a flanking probe, or a detection probe) to facilitate detection of that molecule. Specific, non-limiting examples of labels include fluorescent and fluorogenic moieties, chromogenic moieties, haptens, affinity tags, and radioactive isotopes. The label can be directly detectable (e.g., optically detectable) or indirectly detectable (for example, via interaction with one or more additional molecules that are in turn detectable). Exemplary labels in the context of the probes disclosed herein are described below. Methods for labeling nucleic acids, and guidance in the choice of labels useful for various purposes, are discussed, e.g., in Sambrook and Russell, in *Molecular Cloning: A Laboratory Manual*, 3$^{rd}$ Ed., Cold Spring Harbor Laboratory Press (2001) and Ausubel et al., in *Current Protocols in Molecular Biology*, Greene Publishing Associates and Wiley-Intersciences (1987, and including updates).

Gene Fusion: A hybrid gene formed from two or more previously separate genes. Gene fusions can occur as the result of a chromosomal rearrangement, such as a translocation, interstitial deletion, or chromosomal inversion. The "fusion point" or "breakpoint" of a gene fusion is the point of transition between the sequence from the first gene in the fusion to the sequence from the second gene in the fusion. The terms "gene fusion" and "fusion gene" are used interchangeably herein and indicate the products of a chromosomal rearrangement, including but not limited to DNA (such as genomic DNA or cDNA), RNA, (including mRNA), or protein.

Hybridization: The ability of complementary single-stranded DNA, RNA, or DNA/RNA hybrids to form a duplex molecule (also referred to as a hybridization complex). Nucleic acid hybridization techniques can be used to form hybridization complexes between a nucleic acid probe, and the gene it is designed to target. In particular non-limiting examples, nucleic acid probes are optimized to target the individual genes or gene fusions listed in Table 1.

Hybridization conditions resulting in particular degrees of stringency will vary depending upon the nature of the hybridization method and the composition and length of the hybridizing nucleic acid sequences. Generally, the temperature of hybridization and the ionic strength (such as the Na$^+$ concentration) of the hybridization buffer will determine the stringency of hybridization. Calculations regarding hybridization conditions for attaining particular degrees of stringency are discussed in Sambrook et al., (1989) *Molecular Cloning*, second edition, Cold Spring Harbor Laboratory, Plainview, N.Y. (chapters 9 and 11).

Nuclease: An enzyme that cleaves a phosphodiester bond. An endonuclease is an enzyme that cleaves an internal phosphodiester bond in a nucleotide chain (in contrast to exonucleases, which cleave a phosphodiester bond at the end of a nucleotide chain). Some nucleases have both endonuclease and exonuclease activities. Endonucleases include restriction endonucleases or other site-specific endonucleases (which cleave DNA at sequence specific sites), DNase I, Bal 31 nuclease, S1 nuclease, Mung bean nuclease, Ribonuclease A, Ribonuclease T1, RNase I, RNase PhyM, RNase U2, RNase CLB, micrococcal nuclease, and apuiinic/apyrimidinic endonucleases. Exonucleases include exonuclease III and exonuclease VII. In particular examples, a nuclease is specific for single-stranded nucleic acids, such as S1 nuclease, Mung bean nuclease, Ribonuclease A, or Ribonuclease T1.

Nucleic acid: A deoxyribonucleotide or ribonucleotide polymer in either single or double stranded form, and unless otherwise limited, encompassing analogs of natural nucleotides that hybridize to nucleic acids in a manner similar to naturally occurring nucleotides. The term "nucleotide" includes, but is not limited to, a monomer that includes a base (such as a pyrimidine, purine or synthetic analogs thereof) linked to a sugar (such as ribose, deoxyribose or synthetic analogs thereof), or a base linked to an amino acid, as in a peptide nucleic acid (PNA). A "nucleotide" also includes a locked nucleic acid (LNA). A nucleotide is one monomer in a polynucleotide. A nucleotide sequence refers to the sequence of bases in a polynucleotide.

Probe: A nucleic acid molecule that is capable of hybridizing with a target nucleic acid molecule (e.g., genomic DNA, cDNA, RNA, or mRNA target nucleic acid molecule) and, after hybridization to the target, is capable of being detected either directly or indirectly. Thus probes permit the detection, and in some examples quantification, of a target nucleic acid molecule, such as a gene fusion nucleic acid molecule or a nucleic acid molecule that is involved in a gene fusion event. In some examples, a probe includes a detectable label. In some examples, probes can include one or more peptide nucleic acids and/or one or more locked nucleic acids.

A probe is capable of hybridizing with sequences including one or more variations from a "wild type" sequence or portion of a sequence (for example in a gene fusion). For example, a probe may include a sequence having at least 90% identity (such as 90%, 91%, 92%, 93%, 94%, 95%, 96%, 97%, 98%, 99%, or more identity) with a "wild type" gene sequence.

In some examples, a "fusion probe" is a probe that includes nucleic acid sequences capable of hybridizing with sequences from two separate genes when the two genes are part of a gene fusion. A fusion probe includes a 5' portion capable of hybridizing with a first nucleic acid (for example from a first gene) and a 3' portion capable of hybridizing with a second nucleic acid (for example, from a second gene), wherein the fusion probe spans the point where the first gene and the second gene are fused (the "fusion point").

In other examples, a "flanking probe" is a probe that includes nucleic acid sequences capable of hybridizing with a single nucleic acid and located 5' or 3' to a fusion point. A 5' flanking probe includes a probe capable of hybridizing with a portion of a nucleic acid 5' to a fusion point and a 3' flanking probe includes a probe capable of hybridizing with a portion of a nucleic acid 3' to a fusion point.

Sample: A biological specimen containing DNA (for example, genomic DNA or cDNA), RNA (including mRNA), protein, or combinations thereof, obtained from a subject. Examples include, but are not limited to cells, cell lysates, chromosomal preparations, peripheral blood, urine, saliva, tissue biopsy (such as a tumor biopsy or lymph node biopsy), surgical specimen, bone marrow, amniocentesis samples, and autopsy material. In one example, a sample includes RNA, such as mRNA. In particular examples, samples are used directly (e.g., fresh or frozen), or can be manipulated prior to use, for example, by fixation (e.g., using formalin) and/or embedding in wax (such as formalin-fixed paraffin-embedded (FFPE) tissue samples).

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, Gene, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100.

One indication that two nucleic acid molecules are closely related is that the two molecules hybridize to each other under stringent conditions. Stringent conditions are sequence-dependent and are different under different environmental parameters.

The nucleic acid probes disclosed herein are not limited to the exact sequences shown, as those skilled in the art will appreciate that changes can be made to a sequence, and not substantially affect the ability of a probe to function as desired. For example, sequences having at least 80%, at least 85%, at least 90%, at least 91%, at least 92%, at least 93%, at least 94%, at least 95%, at least 96%, at least 97%, at least 98%, or at least 99%, such as 100% sequence identity to the disclosed probes are provided herein. One of skill in the art will appreciate that these sequence identity ranges are provided for guidance only; it is possible that probes can be used that fall outside these ranges.

Subject: Any organism having a genome, including viruses, single-celled organisms (such as bacteria or yeast), or multi-cellular invertebrate or vertebrate organisms (such as human and non-human mammals). In one example, a subject is known or suspected of having a tumor associated with a gene fusion.

III. Methods of Detecting Gene Fusions Using a Fusion Probe

Figure 1:
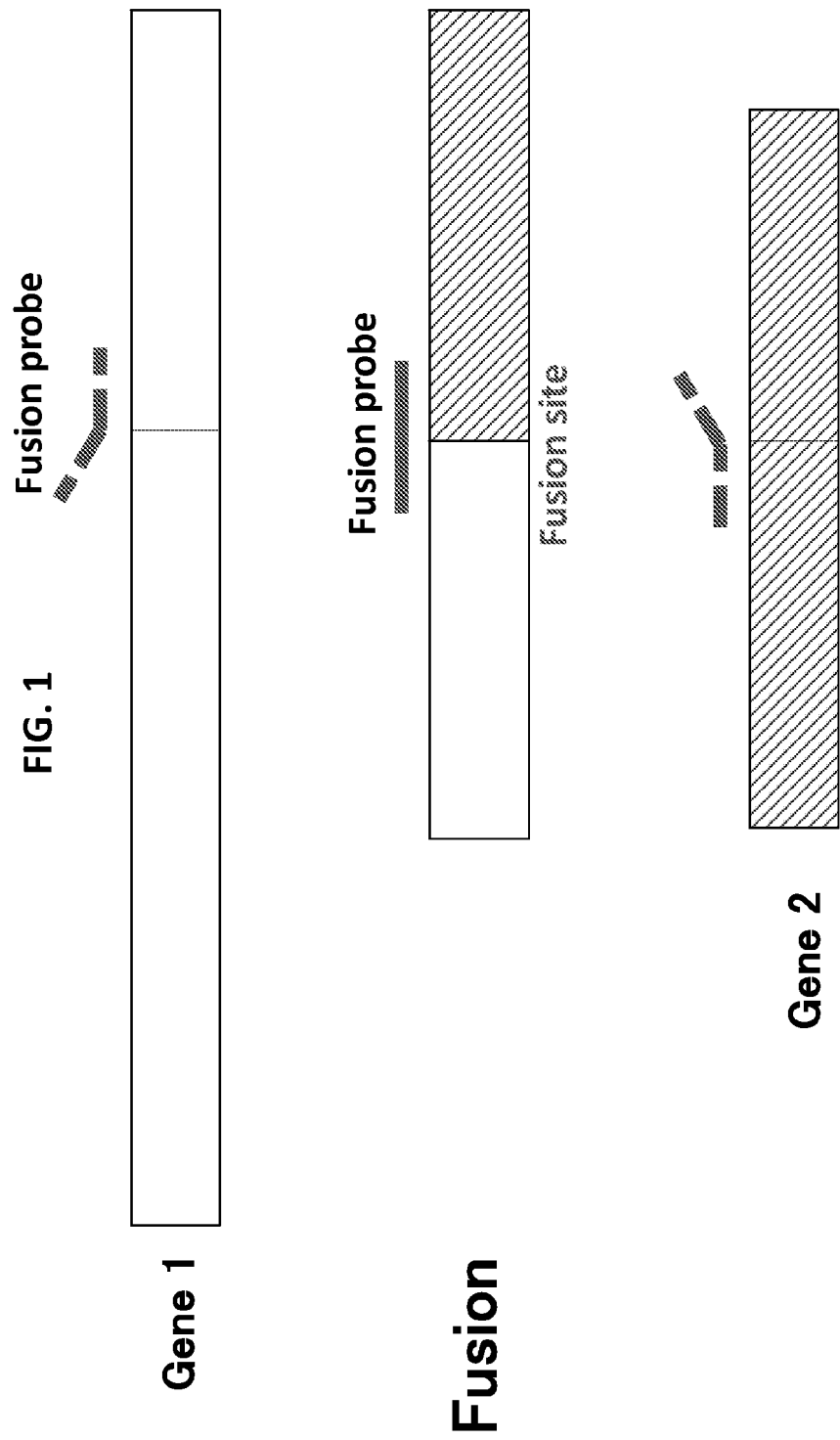
FIG. 1 is a schematic diagram showing exemplary wild-type genes (Genes 1 and 2) and a fusion gene and an exemplary fusion probe. When the gene fusion is present in a sample, the fusion probe hybridizes and is detected following nuclease treatment (solid line). When the gene fusion is not present in a sample, the fusion probe only partially hybridizes to Genes 1 and 2 and at least the non-hybridized portion is hydrolyzed by the nuclease treatment (dotted lines).

In some embodiments, the methods utilize a fusion probe that spans the point of fusion between two nucleic acids or genes. In some examples, a sample is contacted with the fusion probe and treated with a nuclease specific for single-stranded nucleic acids. Only probe that is hybridized and thereby forms a duplex with to the target gene (e.g., a nucleic acid having the target gene fusion) will survive nuclease treatment and be subsequently detected. FIG. 1 is a schematic diagram showing exemplary wild-type and fusion genes and an exemplary fusion probe. When the gene fusion is present in a sample, the fusion probe hybridizes and is detected following nuclease treatment (solid line). When the gene fusion is not present in a sample, the fusion probe only partially hybridizes to Genes 1 and 2 and any portion of the fusion probe that is not duplexed with a target is hydrolyzed by the nuclease treatment. In some examples, the portion of the fusion probe that is duplexed to Gene 1 or Gene 2 survives nuclease treatment, but is not detected (for example, because the detectable portion of the probe is hydrolyzed).

The methods can include contacting a sample (such as a sample including nucleic acids, for example a sample from a subject) with a fusion probe that has a 5' portion complementary to a first nucleic acid and a 3' portion complementary to a second nucleic acid wherein the fusion probe spans a fusion point of the first nucleic acid and the second nucleic acid. The probe is incubated with the sample under conditions sufficient for the fusion probe to specifically hybridize to a gene fusion. The sample is contacted with a nuclease specific for single-stranded nucleic acids (for example, S1 nuclease), and the presence of the fusion probe detected. The fusion gene is identified as present in the sample when the fusion probe is detected. In particular examples, the first nucleic acid and the second nucleic acid are mRNA (for example, the gene fusion nucleic acid detected is mRNA).

The disclosed methods are amenable to multiplexing. This allows screening or detection of multiple gene fusions simultaneously (such as detecting the same fusion in many samples, or detecting multiple different gene fusions in a single sample), for example at least 2, at least 5, at least 10, at least 25, at least 40, at least 50, at least 100, at least 200, at least 300, at least 400, at least 500, at least 750, at least 1000, or more gene fusions in a single assay. In some examples, fusion probes specific for two or more distinct gene fusions (for example, gene fusions involving a different combination of genes or gene fusions involving the same genes, but different fusion points) can be included in the assay. In other examples, the same probe is used for multiple samples and the identity of the sample is based on sample location (for example, position on a microarray). The fusion probes can be labeled (directly or indirectly) with different detectable labels in order to identify the gene fusions. Alternatively, the fusion probes can be labeled (directly or indirectly) with the same label and their identity can be determined based on their spatial position (for example in a microarray).

One of skill in the art can identify conditions sufficient for a fusion probe to specifically hybridize to a gene fusion, such as a gene fusion present in a sample from a subject. For example, one of skill in the art can determine experimentally the features (such as length, base composition, and degree of complementarity) that will enable a nucleic acid (e.g., a fusion probe) to hybridize to another nucleic acid (e.g., a gene fusion nucleic acid) under conditions of selected stringency, while minimizing non-specific hybridization to other substances or molecules. Typically, the nucleic acid sequence of a fusion probe will have sufficient complementarity to the corresponding gene fusion to enable it to hybridize under selected stringent hybridization conditions, for example hybridization at about 37° C. or higher (such as about 37° C., 42° C., 50° C., 55° C., 60° C., 65° C., 70° C., 75° C., or higher). Among the hybridization reaction parameters which can be varied are salt concentration, buffer, pH, temperature, time of incubation, amount and type of denaturant such as formamide. For example, nucleic acid (e.g., a fusion probe) can be added to a sample at a concentration ranging from about 10 pM to about 10 nM (such as about 30 pM to 5 nM, about 100 pM to about 1 nM), in a buffer such as, for example, 6×SSPE-T (0.9 M NaCl, 60 mM $NaH_2PO_4$, 6 mM EDTA, and 0.05% Triton X-100) or lysis buffer (described below). In one example, the probe is added to the sample at a final concentration of about 30 pM. In another example, the probe is added to the sample at a final concentration of about 167 pM. In a further example, the probe is added to the sample at a final concentration of about 1 nM.

The nucleic acids in the sample are denatured (for example at about 95° C. to about 105° C. for about 5-15 minutes) and hybridized to a gene fusion for between about 10 minutes and about 24 hours (for example, at least about 1 hour to 20 hours, or about 6 hours to 16 hours) at a temperature ranging from about 4° C. to about 70° C. (for example, about 37° C. to about 65° C., about 45° C. to about 60° C., or about 50° C. to about 60° C.). In some examples, the fusion probe is incubated with the sample at a temperature of at least about 40° C., at least about 45° C., at least about 50° C., at least about 55° C., at least about 60° C., at least about 65° C., or at least about 70° C. In one example, the fusion probe is incubated with the sample at about 60° C. In another example, the fusion probe is incubated with the sample at about 50° C. These hybridization temperatures are exemplary, and one of skill in the art can select appropriate hybridization temperature depending on factors such as the length and nucleotide composition of the fusion probe.

In some embodiments, the methods do not include nucleic acid purification (for example, nucleic acid purification is not performed prior to contacting the sample with the fusion probe and/or nucleic acid purification is not performed following contacting the sample with the fusion probe). In some examples, no pre-processing of the sample is required except for cell lysis. In some examples, cell lysis and contacting the sample with the fusion probe occur sequentially. In other examples, cell lysis and contacting the sample with the fusion probe occur concurrently, in some non-limiting examples without any intervening steps.

Following hybridization of the fusion probe and nucleic acids in the sample, the sample is subjected to a nuclease protection procedure. Fusion probes which have hybridized to a gene fusion are not hydrolyzed by the nuclease and can be subsequently detected.

Treatment with one or more nucleases will destroy nucleic acid molecules other than the fusion probes which have hybridized to a gene fusion nucleic acid present in the sample. For example, if the sample includes a cellular extract or lysate, unwanted nucleic acids, such as genomic DNA, cDNA, tRNA, rRNA and mRNAs other than the gene fusion of interest and portions of the gene fusion of interest that are not hybridized to complementary probe sequences, can be substantially destroyed in this step. Any of a variety of nucleases can be used, including, pancreatic RNAse, mung bean nuclease, S1 nuclease, RNAse A, Ribonuclease T1, Exonuclease III, Exonuclease VII, RNAse CLB, RNAse PhyM, RNAse U2, or the like, depending on the nature of the hybridized complexes and of the undesirable nucleic acids present in the sample. One of skill in the art can select an appropriate nuclease, for example based on whether DNA or RNA is to be detected. In a particular example, the nuclease is specific for single-stranded nucleic acids, for example S1 nuclease. An advantage of using a nuclease specific for single-stranded nucleic acids in some method embodiments disclosed herein is to remove such single-stranded ("sticky") molecules from subsequent reaction steps where they may lead to unnecessary background or cross-reactivity. S1 nuclease is commercially available from for example, Promega, Madison, Wis. (cat. no. M5761); Life Technologies/Invitrogen, Carlsbad, Calif. (cat. no. 18001-016); Fermentas, Glen Burnie, Md. (cat. no. EN0321), and others. Reaction conditions for these enzymes are well-known in the art and can be optimized empirically.

In some examples, S1 nuclease diluted in an appropriate buffer (such as 0.25 M sodium acetate, pH 4.5, 1.4 M NaCl, 0.0225 M $ZnSO_4$, 0.05% KATHON) is added to the hybridized probe mixture and incubated at about 50° C. for about 30-120 minutes (for example, about 60-90 minutes) to digest non-hybridized nucleic acid and fusion probe.

The samples optionally are treated to otherwise remove non-hybridized material and/or to inactivate or remove residual enzymes (e.g., by phenol extraction, precipitation, column filtration, etc.). In some examples, the samples are optionally treated to dissociate the target nucleic acid (such as target gene fusion or target full length or wild type gene) from the probe (e.g., using base hydrolysis and heat). After hybridization, the hybridized target can be degraded, e.g., by nucleases or by chemical treatments, leaving the fusion probe in direct proportion to how much probe had been hybridized to target. Alternatively, the sample can be treated so as to leave the (single strand) hybridized portion of the target, or the duplex formed by the hybridized target and the probe, to be further analyzed.

The presence of the fusion probe is then detected. Any suitable method can be used to detect the fusion probe following hybridization and nuclease treatment. In some examples, the fusion probe includes a detectable label and detecting the presence of the fusion probe includes directly detecting the detectable label. In other examples, the fusion probe is detected indirectly, for example by hybridization with a labeled nucleic acid. In some examples, the fusion probe is detected using a microarray, for example, a microarray including a detectably labeled nucleic acid (for example labeled with biotin or horseradish peroxidase) that is complementary to the fusion probe (see, for example, FIG. 5A). In other examples, the fusion probe is detected using a microarray including a programming linker complementary to a portion of the fusion probe and subsequently incubating with a detection linker, a portion of which is complementary to a separate portion of the fusion probe. The detection linker can be detectably labeled, or a separate portion of the detection linker is complementary to an additional nucleic acid including a detectable label (such as biotin or horseradish peroxidase). See, for example, FIG. 5B. Methods of detecting the probes are provided in greater detail in Section V below.

In some embodiments, fusion probes of use in the disclosed methods are about 10-200 nucleotides in length. In some embodiments, fusion probes of use in the disclosed methods are no more than 500, no more than 400, no more than 300, or no more than 200 nucleotides in length, such as 20 to 100 nucleotides in length. In some examples, the fusion probe includes approximately equal numbers of nucleotides from each of the first and second nucleic acids. Fusion probes are discussed in more detail in Section VIB, below.

In other examples, the fusion probe includes a small number of nucleotides complementary to one of the two nucleic acids (a "short overlap") and a greater number of nucleotides from the other nucleic acid. In particular examples, the "short overlap" portion of the fusion probe also includes a detectable label (such as biotin, fluorescein or other fluorescent molecules, digoxigenin, or dinitrophenol). The fusion probe can be end-labeled (for example, the detectable label is included at the 5' or 3' end of the probe) or the detectable label can be included at one or more internal positions of the fusion probe. FIG. 2 is a schematic diagram showing exemplary wild-type and fusion genes and an exemplary direct-labeled fusion probe having a four nucleotide overlap with the 5' portion of the fusion gene. The label (biotin in this example) is located at or near the 5' end of the probe (for example at the 5' end or in the "short overlap" portion of the probe). When the gene fusion is present in a sample, the fusion probe hybridizes and the label is detected following nuclease treatment (top panel). The fusion probe does not hybridize to Gene 1 and is hydrolyzed by the nuclease treatment (middle panel). The fusion probe hybridizes to Gene 2, however the 5' end including the label does not hybridize and is cleaved by the nuclease treatment (bottom panel). Therefore, the labeled probe is only detected in samples where the gene fusion is present.

In some examples, the 5' portion of the probe can be about 1-10 nucleotides in length and the 3' portion of the probe can be about 10-200 nucleotides or more in length or the 5' portion of the probe can be about 10-200 nucleotides or more in length and the 3' portion of the probe can be about 1-10 nucleotides in length. Short overlap fusion probes are discussed in more detail in Section VIB, below.

IV. Methods of Detecting Gene Fusions Using Ratio of Flanking Probes

In other embodiments, the methods of detecting the presence of a fusion gene in a sample from a subject utilize two or more probes that flank the point of fusion between two nucleic acids or genes. FIG. 3 is a schematic diagram showing exemplary wild type and fusion genes and exemplary flanking probes and (an optional exemplary fusion probe). The fusion gene includes a 5' portion of Gene 1 and a 3' portion of Gene 2 (middle panel). The flanking 5' probe 1 and 3' probe 1 hybridize to the full-length (e.g., wild type) Gene 1 and are detected following nuclease treatment (top panel). The flanking 5' probe 1 also hybridizes to the fusion gene and is detected following nuclease treatment (middle panel); however the flanking 3' probe 1 does not hybridize to the fusion gene and is hydrolyzed by nuclease treatment (middle panel). The flanking 5' probe 2 and 3' probe 2 can optionally be included in the assay; these hybridize to the full-length (e.g., wild type) Gene 2 and are detected following nuclease treatment (bottom panel). The 3' probe 2 also hybridizes to the fusion gene and is detected following nuclease treatment; however the flanking 5' probe 2 does not hybridize to the fusion gene and is hydrolyzed by the nuclease treatment (middle panel). A fusion probe spanning the fusion point can also optionally be included in the assay.

When the gene fusion is present in a sample, the fusion probe hybridizes and is detected following nuclease treatment (solid line). When the gene fusion is not present in a sample, the fusion probe only partially hybridizes to Genes 1 and 2 and is hydrolyzed by the nuclease treatment (dotted lines). In some examples, the portion of the fusion probe that is duplexed to Gene 1 or Gene 2 remains, but is not detected (for example, because the detectable portion of the probe is hydrolyzed).

The methods can include contacting a sample from a subject with a first probe complementary to a first nucleic acid 5' to a fusion point between the first nucleic acid and a second nucleic acid under conditions sufficient for the first probe to specifically hybridize to the first nucleic acid, contacting the sample with a second probe complementary to the first nucleic acid 3' to the fusion point between the first and second nucleic acids under conditions sufficient for the second probe to specifically hybridize to the first nucleic acid, contacting the sample with a nuclease specific for single-stranded nucleic acids (for example, S1 nuclease), detecting presence of the first probe and the second probe, and determining a ratio of the first probe to the second probe. The fusion gene is identified as present in the sample when the ratio of the first probe to the second probe is different from one (for example, statistically significantly different from one). In some examples, the gene fusion is detected and does not include a 3' portion of the first nucleic acid if the ratio of the first probe to the second probe is greater than one (for example, statistically significantly greater than one). In other examples, the gene fusion is detected and does not include a 5' portion of the first nucleic acid if the ratio of the first probe to the second probe is less than one (for example, statistically significantly less than one). In particular examples, the first nucleic acid and the second nucleic acid are mRNA (for example, the gene fusion nucleic acid detected is mRNA). In other examples, the methods include determining a ratio of the second probe to the first probe. In some examples, the gene fusion is detected and does not include a 5' portion of the first nucleic acid if the ratio of the second probe to the first probe is greater than one (for example, statistically significantly greater than one). In other examples, the gene fusion is detected and does not include a 3' portion of the first nucleic acid if the ratio of the second probe to the first probe is less than one (for example, statistically significantly less than one). In some examples, the first probe and the second probe are each about 10-200 nucleic acids in length. In some examples, the sample is contacted with two or more probes that are complementary to the first nucleic acid 5' to the fusion point and/or contacted with two or more probes that are complementary to the first nucleic acid 3' to the fusion point. In other examples, the sample is contacted with one or more probes that are complementary to the first nucleic acid in the gene fusion (for example at least one 5' flanking probe and at least one 3' flanking probe) and one or more probes that are complementary to the second nucleic acid in the gene fusion (for example, at least one 5' flanking probe and at least one 3' flanking probe). In still further examples, the sample is contacted with one or more 5' and 3' flanking probes complementary to a first or second nucleic acid in a gene fusion and one or more 5' and 3' flanking probes complementary to a first or second nucleic acid in a different gene fusion. The probes can be labeled with different detectable labels or can be labeled with the same detectable label and distinguished based on spatial information (for example, using a microarray).

The disclosed methods are amenable to multiplexing. This allows screening or detection of multiple gene fusions simultaneously (such as detecting the same fusion in many samples, or detecting multiple different gene fusions in a single sample), for example at least 2, at least 5, at least 10, at least 25, at least 40, at least 50, at least 100, at least 200, at least 300, at least 400, at least 500, at least 750, at least 1000, or more gene fusions in a single assay. In some examples, 5' and 3' flanking probes specific for two or more distinct gene fusions (for example, gene fusions involving a different combination of genes or gene fusions involving the same genes, but different fusion points) can be included in the assay. In other examples, the same set of flanking probes is used for multiple samples and the identity of the sample is based on sample location (for example, position on a microarray). The flanking probes can be labeled (directly or indirectly) with different detectable labels in order to identify the gene fusions. Alternatively, the flanking probes can be labeled (directly or indirectly) with the same label and their identity can be determined based on their spatial position (for example in a microarray).

One of skill in the art can identify conditions sufficient for a probe (such as a 5' flanking probe and a 3' flanking probe) to specifically hybridize to a nucleic acid, such as a full-length and/or gene fusion nucleic acid present in a sample from a subject. For example, one of skill in the art can determine experimentally the features (such as length, base composition, and degree of complementarity) that will enable a nucleic acid (e.g., a flanking probe) to hybridize to another nucleic acid (e.g., a full-length or a gene fusion nucleic acid) under conditions of selected stringency, while minimizing non-specific hybridization to other substances or molecules. Typically, the nucleic acid sequence of a flanking probe will have sufficient complementarity to the corresponding full-length gene and the gene fusion to enable it to hybridize under selected stringent hybridization conditions, for example hybridization at about 37° C. or higher (such as about 37° C., 42° C., 50° C., 55° C., 60° C., 65° C., 70° C., 75° C., or higher). Among the hybridization reaction parameters which can be varied are salt concentration, buffer, pH, temperature, time of incubation, amount and type of denaturant such as formamide. For example, nucleic acid (e.g., a flanking probe) can be added to a sample at a concentration ranging from about 10 pM to about 10 nM (such as about 30 pM to 5 nM, about 100 pM to about 1 nM), in a buffer such as, for example, 6×SSPE-T (0.9 M NaCl, 60 mM NaH$_2$PO$_4$, 6 mM EDTA, and 0.05% Triton X-100) or lysis buffer (described below). In one example, the probe is added to the sample at a final concentration of about 30 pM. In another example, the probe is added to the sample at a final concentration of about 167 pM. In a further example, the probe is added to the sample at a final concentration of about 1 nM.

The nucleic acids in the sample are denatured (for example at about 95° C. to about 105° C. for about 5-15 minutes) and hybridized to a gene fusion for between about 10 minutes and about 24 hours (for example, at least about 1 hour to 20 hours, or about 6 hours to 16 hours) at a temperature ranging from about 4° C. to about 70° C. (for example, about 37° C. to about 65° C., about 45° C. to about 60° C., or about 50° C. to about 60° C.). In some examples, the flanking probes are incubated with the sample at a temperature of at least about 40° C., at least about 45° C., at least about 50° C., at least about 55° C., at least about 60° C., at least about 65° C., or at least about 70° C. In one example, the flanking probes are incubated with the sample at about 60° C. In another example, the flanking probes are incubated with the sample at about 50° C. These hybridization temperatures are exemplary, and one of skill in the art can select appropriate hybridization temperature depending on factors such as the length and nucleotide composition of the flanking probes.

In some embodiments, the methods do not include nucleic acid purification (for example, nucleic acid purification is not performed prior to contacting the sample with the flanking probes and/or nucleic acid purification is not performed following contacting the sample with the flanking probes). In some examples, no pre-processing of the sample is required except for cell lysis. In some examples, cell lysis and contacting the sample with the flanking probes occur sequentially. In other examples, cell lysis and contacting the sample with the flanking probes occur concurrently, in some non-limiting examples without any intervening steps.

Following hybridization of the one or more flanking probes and nucleic acids in the sample, the sample is subjected to a nuclease protection procedure. Flanking probes which have hybridized to a full-length nucleic acid or a gene fusion are not hydrolyzed by the nuclease and can be subsequently detected.

Treatment with one or more nucleases will destroy nucleic acid molecules other than the flanking probes which have hybridized to a full-length or gene fusion nucleic acid present in the sample. For example, if the sample includes a cellular extract or lysate, unwanted nucleic acids, such as genomic DNA, cDNA, tRNA, rRNA and mRNAs other than the gene or gene fusion of interest and portions of the gene fusion of interest that are not hybridized to complementary probe sequences, can be substantially destroyed in this step. Any of a variety of nucleases can be used, including, pancreatic RNAse, mung bean nuclease, S1 nuclease, RNAse A, Ribonuclease T1, Exonuclease III, Exonuclease VII, RNAse CLB, RNAse PhyM, RNAse U2, or the like, depending on the nature of the hybridized complexes and of the undesirable nucleic acids present in the sample. In a particular example, the nuclease is specific for single-stranded nucleic acids, for example S1 nuclease. An advantage of using a nuclease specific for single-stranded nucleic acids in some method embodiments disclosed here is to remove such single-stranded ("sticky") molecules from subsequent reaction steps where they may lead to unnecessary background or cross-reactivity. S1 nuclease is commercially available from for example, Promega, Madison, Wis. (cat. no. M5761); Life Technologies/Invitrogen, Carlsbad, Calif. (cat. no. 18001-016); Fermentas, Glen Burnie, Md. (cat. no. EN0321), and others. Reaction conditions for these enzymes are well-known in the art and can be optimized empirically.

In some examples, 51 nuclease diluted in an appropriate buffer (such as a buffer including sodium acetate, sodium chloride, zinc sulfate, and detergent, for example, 0.25 M sodium acetate, pH 4.5, 1.4 M NaCl, 0.0225 M ZnSO$_4$, 0.05% KATHON) is added to the hybridized probe mixture and incubated at about 50° C. for about 30-120 minutes (for example, about 60-90 minutes) to digest unhybridized nucleic acid and unbound probes.

The samples optionally are treated to otherwise remove unhybridized material and/or to inactivate or remove residual enzymes (e.g., by phenol extraction, precipitation, column filtration, etc.). In some examples, the samples are optionally treated to dissociate the target nucleic acid (such as target gene fusion or target full length or wild type gene) from the probe (e.g., using base hydrolysis and heat). After hybridization, the hybridized target can be degraded, e.g., by nucleases or by chemical treatments, leaving the flanking probes in direct proportion to how much probe had been hybridized to target. Alternatively, the sample can be treated so as to leave the (single strand) hybridized portion of the target, or the duplex formed by the hybridized target and the probe, to be further analyzed.

The presence of the flanking probes in the sample is then detected and a ratio of the first probe (5' flanking probe) to the second probe (3' flanking probe) is determined. The presence of a gene fusion in the sample is detected if the ratio of the 5' flanking probe to the 3' flanking probe is different from one (for example, statistically significantly different from one). As shown in FIG. 3, the effect of a gene fusion on the ratio of 5' and 3' flanking probes depends on whether the flanking probes are complementary to the 5' gene in the fusion (Gene 1 in FIG. 3) or the 3' gene in the fusion (Gene 2 in FIG. 3).

In one example, the first and second probes (the 5' and 3' flanking probes, respectively) are complementary to the 5' gene in the fusion. In this example, the gene fusion is detected and does not include a 3' portion of the nucleic acid (Gene 1) if the ratio of the first probe to the second probe is greater than one (for example, statistically significantly greater than one). In some examples, the gene fusion is present and does not include a 3' portion of the nucleic acid if the ratio is about at least 1.1, such as at least 1.5, at least 1.8, at least 2, at least 2.5, at least 3, at least 4, at least 5, at least 10 or at least 20, for example 1.1 to 20 or 1.1 to 60, such as 1.1, 1.2, 1.3, 1.4, 1.5, 1.6, 1.7, 1.8, 1.9, 2.0, 2.5, 3.0, 3.5, 4.0, 0.4.5, 5.0, 5.5, 6.0, 6.5, 7.0, 7.5, 8.0, 8.5, 9.0, 9.5, 10, 11, 12, 13, 14, 15, 16, 17, 18, 19, 20, 330, 40, 50, 60, or more. In particular examples, a gene fusion is present and does not include a 3' portion of the nucleic acid if the ratio is about at least 1.5. In other examples, a gene fusion is present and does not include a 3' portion of the nucleic acid if the ratio is about at least 1.8. In other examples, the gene fusion is detected and does not include a 5' portion of the nucleic acid (gene 1) if the ratio of the first probe to the second probe is less than one (for example, statistically significantly less than one). In some examples, the gene fusion is present and does not include a 5' portion of the nucleic acid if the ratio is no more than 0.95, such as no more than 0.9, no more than 0.8, no more than 0.7, no more than 0.6, no more than 0.5, or no more than 0.1, for example 0.05 to 0.95, such as about 0.95, 0.9, 0.85, 0.8, 0.75, 0.7, 0.65, 0.6, 0.55, 0.5, 0.45, 0.4, 0.35, 0.3, 0.25, 0.2, 0.15, 0.1, 0.05, or less.

In another example, the first and second probes (the 5' and 3' flanking probes, respectively) are complementary to the 3' gene in the fusion. In this example, the gene fusion is detected and does not include a 3' portion of the nucleic acid if the ratio of the first probe to the second probe is greater than one (for example, statistically significantly greater than one). In some examples, the gene fusion is present and does not include a 3' portion of the nucleic acid (gene 2) if the ratio is at least 1.1, such as at least 1.5, at least 1.8, at least 2, at least 2.5, at least 3, at least 4, at least 5, at least 10 or at least 20, for example 1.1 to 20 or 1.1 to 60, such as about 1.1, 1.2, 1.3, 1.4, 1.5, 1.6, 1.7, 1.8, 1.9, 2.0, 2.5, 3.0, 3.5, 4.0, 0.4.5, 5.0, 5.5, 6.0, 6.5, 7.0, 7.5, 8.0, 8.5, 9.0, 9.5, 10, 11, 12, 13, 14, 15, 16, 17, 18, 19, 20, 30, 40, 50, 60, or more. In particular examples, a gene fusion is present and does not include a 5' portion of the nucleic acid if the ratio is about at least 1.5. In other examples, a gene fusion is present and does not include a 3' portion of the nucleic acid if the ratio is about at least 1.8. In other examples, the gene fusion is detected and does not include a 5' portion of the nucleic acid (gene 2) if the ratio of the first probe to the second probe is less than one (for example, statistically significantly less than one). In some examples, the gene fusion is present and does not include a 3' portion of the nucleic acid if the ratio is no more than 0.95, such as no more than 0.9, no more than 0.8, no more than 0.7, no more than 0.6, no more than 0.5, or no more than 0.1, for example 0.05 to 0.95, such as about 0.95, 0.9, 0.85, 0.8, 0.75, 0.7, 0.65, 0.6, 0.55, 0.5, 0.45, 0.4, 0.35, 0.3, 0.25, 0.2, 0.15, 0.1, 0.05, or less.

In some embodiments, the gene fusion is present if the ratio of the flanking probes (for example, the ratio of a 5' flanking probe to a 3' flanking probe or the ratio of a 3' flanking probe to a 5' flanking probe) differs from a control (such as an average ratio in a wild-type sample) by at least two standard deviations (for example, at least 2, 3, 4, 5, or more standard deviations). In some examples, the control is the ratio (for example the average ratio) of flanking probes in a sample that does not include a gene fusion.

In some examples, for example in the case of an RNA or mRNA that is normally expressed at high levels, the flanking probe ratio when a gene fusion is present may be less than when the RNA or mRNA is normally expressed at lower levels. One of skill in the art can determine the level at which an RNA or mRNA is normally expressed in a cell and determine the range of ratios that are expected to reflect the presence of a gene fusion in the sample.

In additional embodiments, the methods include determining the percentage of gene fusion in the sample relative to the first nucleic acid or the second nucleic acid. The methods include contacting the sample with a fusion probe including a 5' portion complementary to a first nucleic acid and a 3' portion complementary to a second nucleic acid (such as discussed in Section III, above) under conditions sufficient for the fusion probe to specifically hybridize to a gene fusion, wherein the fusion probe spans a fusion point of the first nucleic acid and the second nucleic acid in addition to contacting the sample with the first probe and the second probe above. The methods further include detecting presence of the fusion probe and determining a ratio of the fusion probe to the first probe and/or a ratio of the fusion probe to the second probe.

In some examples, the percentage of the gene fusion relative to the full length gene (e.g., the wild type or non-fusion gene) can be determined by determining the ratio of the fusion probe to the first probe (e.g., the 5' flanking probe) or the ratio of the fusion probe to the second probe (e.g., the 3' flanking probe). For example, if the 5' portion of the gene is present in the gene fusion, the ratio of the fusion probe to the 5' flanking probe will be the percentage of the gene fusion nucleic acid present in the sample relative to the full length nucleic acid. Likewise, if the 3' portion of the gene is present in the gene fusion, the ratio of the fusion probe to the 3' flanking probe will be the percentage of the gene fusion nucleic acid present in the sample relative to the full length nucleic acid.

Any suitable method can be used to detect the probes. In some examples, the first and/or second probe (the flanking probes) includes a detectable label and detecting the presence of the probe(s) includes detecting the detectable label. In some examples, the flanking probes are labeled with the same detectable label. In other examples, the flanking probes are labeled with different detectable labels. In other examples, the flanking probes are detected indirectly, for example by hybridization with a labeled nucleic acid. In some examples, the flanking probes are detected using a microarray, for example, a microarray including nucleic acids that are complementary to the flanking probes (see, for example, FIG. 5A). In other examples, the flanking probes are detected using a microarray including programming linkers complementary to a portion of each of the flanking probes and subsequently incubating with detection linkers, a portion of which is complementary to a separate portion of the flanking probes. The detection linkers can be detectably labeled, or a separate portion of the detection linkers are complementary to additional nucleic acids including a detectable label (such as biotin or horseradish peroxidase). See, for example, FIG. 5B. Methods of detecting the probes are provided in greater detail in Section V below.

V. Methods of Detecting Probe Hybridization

Any suitable method of detecting the presence of a nucleic acid (such as a probe) in a sample can be utilized in the disclosed methods. One of skill in the art can select appropriate detection methods. In some examples, the disclosed probes (such as one or more fusion or flanking probes) are directly labeled. In other examples, the disclosed probes are detected by hybridization with a detection probe, which has a sequence complementary to at least a portion of the fusion or flanking probe and a detectable label. Detectable labels and methods of incorporating such labels into a nucleic acid molecule such as a probe are well known in the art. In non-limiting examples, nucleic acid probes are labeled with dNTPs covalently attached to hapten molecules (such as a nitro-aromatic compound (e.g., dinitrophenyl (DNP)), biotin, fluorophores (such as fluorescein), digoxigenin, etc.). Methods for conjugating haptens and other labels to nucleotides (e.g., to facilitate incorporation into labeled probes) are well known in the art. For examples of procedures, see, e.g., U.S. Pat. Nos. 5,258,507, 4,772,691, 5,328,824, and 4,711,955. A label can be directly or indirectly attached to a dNTP at any location on the dNTP, such as a phosphate (e.g., α, β or γ phosphate) or a sugar.

In one example, where the label is a hapten, detection of labeled nucleic acid molecules can be accomplished by contacting the hapten-labeled nucleic acid molecules bound to the genomic target sequence with a primary anti-hapten antibody. In one example, the primary anti-hapten antibody (such as a mouse anti-hapten antibody) is directly labeled with an enzyme. In another example, a secondary antiantibody (such as a goat anti-mouse IgG antibody) conjugated to an enzyme is used for signal amplification. In one example, the label is biotin and detection is accomplished by contacting the sample with avidin-horseradish peroxidase.

In additional examples, a detectable label includes various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Additional detectable labels include Raman (light scattering) probes.

In additional examples, probes are labeled with fluorescent molecules (or fluorochromes). Numerous fluorochromes are known to those of skill in the art, and can be selected, for example from Life Technologies (formerly Invitrogen), e.g., see, The Handbook—A Guide to Fluorescent Probes and Labeling Technologies. Examples of particular fluorophores that can be attached (for example, chemically conjugated) to a nucleic acid molecule (such as a uniquely specific binding region) are provided in U.S. Pat. No. 5,866,366. Other suitable fluorophores include thiol-reactive europium chelates which emit at approximately 617 nm (Heyduk and Heyduk, *Anal. Biochem.* 248:216-27, 1997; *J. Biol. Chem.* 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art can also be used, for example those available from Life Technologies (Invitrogen; Molecular Probes (Eugene, Oreg.)) and including the ALEXA FLUOR® series of dyes (for example, as described in U.S. Pat. Nos. 5,696,157, 6,130,101 and 6,716,979), the BODIPY series of dyes (dipyrromethenboron difluoride dyes, for example as described in U.S. Pat. Nos. 4,774,339, 5,187,288, 5,248,782, 5,274,113, 5,338,854, 5,451,663 and 5,433,896), Cascade Blue (an amine reactive derivative of the sulfonated pyrene described in U.S. Pat. No. 5,132,432) and Marina Blue (U.S. Pat. No. 5,830,912). A fluorescent label can also be a fluorescent nanoparticle, such as a semiconductor nanocrystal, e.g., a QUANTUM DOT™ (obtained, for example, from Life Technologies (Quantum-Dot Corp, Invitrogen Nanocrystal Technologies, Eugene, Oreg.); see also, U.S. Pat. Nos. 6,815,064; 6,682596; and 6,649,138).

In some examples, the probes are designed such that hybridization of each probe and subsequent nuclease treatment produces a fragment of a specific size. The probes can then be detected (directly or indirectly) utilizing size-separation techniques, such as gel electrophoresis (for example, slab or capillary gel electrophoresis) or liquid chromatography (for example, HPLC). In some examples, the probes can be labeled with different detectable labels (for example different fluors) in order to discriminate fragments that are similar in size. The probes can also be detected utilizing mass spectrometry methods.

In some examples, the disclosed fusion or flanking probes can be labeled with different detectable labels or can be contacted with different detection probes, in order to separately detect each probe if more than one probe is present in a reaction mixture. In other examples, the presence of one or more probes is detected using a microarray. In such examples, the fusion and/or flanking probes can be labeled with the same detectable label, and the probes are distinguished based on the spatial location of signal on the microarray.

In some examples, the probes are detected on a microarray using a quantitative nuclease protection assay technique, for example, as described in International Patent Publications WO 99/032663; WO 00/037683; WO 00/037684; WO 00/079008; WO 03/002750; and WO 08/121927; and U.S. Pat. Nos. 6,238,869; 6,458,533; and 7,659,063, incorporated herein by reference in their entirety. See also, Martel et al, *Assay and Drug Development Technologies.* 2002, 1 (1-1): 61-71; Martel et al, *Progress in Biomedical Optics and Imaging,* 2002, 3:35-43; Martel et al, *Gene Cloning and Expression Technologies,* Q. Lu and M. Weiner, Eds., Eaton Publishing, Natick (2002); Seligmann, B. *PharmacoGenomics,* 2003, 3:36-43; Martel et al, "Array Formats" in "Microarray Technologies and Applications," U. R. Muller and D. Nicolau, Eds, Springer-Verlag, Heidelberg; Sawada et al, *Toxicology in Vitro,* 20:1506-1513; Bakir, et al, *Biorg. & Med. Chem Lett,* 17: 3473-3479; Kris, et al, *Plant Physiol.* 144: 1256-1266; Roberts, et al, *Laboratory Investigation,* 87: 979-997; Rimsza, et al. *Blood,* 2008 Oct. 15, 112 (8): 3425-3433; Pechhold, et al, *Nature Biotechnology,* 27, 1038-1042. All of these are fully incorporated by reference herein.

Briefly, in one non-limiting example, following hybridization and nuclease treatment, the solution is neutralized and transferred onto a microarray, such as a programmed ARRAYPLATE (HTG Molecular, Tucson, Ariz.; each element of the ARRAYPLATE is programmed to capture a specific probe, for example utilizing an anchor attached to the plate and a programming linker associated with the anchor), and the probes are captured during an incubation (for example, overnight at about 50° C.). The platform can instead be a NIMBLEGEN microarray (Roche Nimblegen, Madison, Wis.) or the probes can be captured on X-MAP beads (Luminex, Austin, Tex.), an assay referred to as the QBEAD assay, or processed further, including as desired PCR amplification or ligation reactions, and for instance then measured by sequencing, or by methods such as NANOSTRING). The media is removed and a cocktail of probe-specific detection linkers are added, in the case of the ARRAYPLATE and QBEAD assays, which hybridize to their respective (captured) probes during an incubation (for example, 1 hour at about 50° C.). See, for example, FIG. 5B. This step is skipped in the case of the NIMBLEGEN microarray assays because the probes are directly biotinylated, and there is no use of detection linker (e.g., FIG. 5A). Specific for the ARRAYPLATE and QBEAD assays, the array or beads are washed and then a biotin linker (an oligonucleotide that hybridizes to a common sequence on every detection linker, with biotin incorporated into it) is added and incubated (for example, 1 hour at about 50° C.). For the ARRAYPLATE (mRNA assay), HRP-labeled avidin (avidin-HRP) is added and incubated (for example at about 37° C. for 1 hour), then washed to remove unbound avidin-HRP. Substrate is added and the plate is imaged to measure the intensity of every element within the plate. In the case of QBEAD Avidin-PE is added, the beads are washed, and then measured by flow cytometry using the Luminex 200, FLEXMAP 3D, or other appropriate instrument. In the case of the NIMBLEGEN arrays, after the addition of avidin-HRP a tyramide signal amplification step is optionally carried out in the presence of substrate, resulting in the deposition of Cy3 labeled probe, the slides are washed, dried, and scanned in a standard microarray scanner. Exemplary programming linkers and detection linkers are provided in Table 6 (Example 1). One of skill in the art can design suitable programming linkers, detection linkers, and other reagents for use in a quantitative nuclease protection assay based upon the fusion probes and/or flanking probes utilized in the methods disclosed herein.

One of skill in the art can identify other suitable methods for detecting probes utilized in the methods disclosed herein.

VI. Exemplary Gene Fusions and Probes

One of skill in the art can identify gene fusions and appropriate probes for use in the methods disclosed herein. For example, databases providing gene fusions or identifying genes involved in gene fusions are publicly available. See e.g., HYBRIDdb (primate.or.kr/hybriddb); ChimerDB (ercsb.ewha.ac.kr:8080/FusionGene/index.jsp); Cancer Genome Anatomy Project Recurrent Chromosome Aberrations in Cancer (cgap.nci.nih.gov/Chromosomes/Recurrent-Aberrations); Cancer Genome Project, Sanger Institute (sanger.ac.uk/genetics/CGP/Census/); COSMIC (sanger-.ac.uk/genetics/CGP/cosmic); Atlas of Genetics and Cytogenetics in Oncology and Haematology (atlasgeneticsoncology.org). See also, Hahn et al., *Proc. Natl. Acad. Sci. USA* 101:13257-13261, 2004; Futreal et al., *Nature Rev. Cancer* 4:177-183, 2004.

In some examples, the disclosed methods include the step of selecting a particular gene fusion, referred to herein as a target gene fusion. Based on the target gene fusion, fusion probes and/or flanking probes can be designed to be used in the disclosed methods using the criteria set forth herein in combination with the knowledge of one skilled in the art. In some non-limiting examples, gene fusions are oncogenic gene fusions. For example, if a subject is known or suspected of having a particular type of tumor, such as chronic myelogenous leukemia or acute myelogenous leukemia, the gene fusion selected can be one that is associated with that tumor (such as a Bcr-Abl gene fusion). Exemplary gene fusions and associated tumors are shown in Table 1. Additional gene fusions include non-oncogenic (e.g., non-transforming gene fusions) and genomic changes that provide a selective advantage (e.g., in pathogens such as viruses and bacteria).

Criteria for probe design are well known to one of skill in the art. Factors that affect probe-target hybridization specificity include probe length, melting temperature, self-complementarity, and the presence of repetitive or non-unique sequence. See, e.g., Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999.

The specificity of a probe increases with length. Thus for example, a probe that includes 30 consecutive nucleotides will anneal to a target sequence with a higher specificity than a corresponding probe of only 15 nucleotides. Thus, the fusion and flanking probes disclosed herein can be selected to include at least 10, at least 15, at least 20, at least 25, at least 30, at least 35, at least 40, at least 45, at least 50, at least 55, at least 60, at least 65, at least 70 or more consecutive nucleotides complementary to a gene fusion or complementary to a particular nucleic acid molecule. In some examples the fusion or flanking probes disclosed herein are not more than 500 nucleotides, such as no more than 400, no more than 300, no more than 250, no more than 200, no more than 100, or even no more than 50 consecutive nucleotides complementary to a gene fusion or complementary to a particular nucleic acid molecule such as 10 to 500 nucleotides, 10 to 400 nucleotides, 10 to 250 nucleotides, 10 to 200 nucleotides, 10 to 100 nucleotides, 10 to 75 nucleotides, 10 to 60 nucleotides, 40 to 80 nucleotides, 100 to 200 nucleotides, or 10 to 50 consecutive nucleotides complementary to a gene fusion or complementary to a particular nucleic acid molecule (for example a first or second nucleic acid that is part of a gene fusion). In particular examples, a probe is at least 10 nucleotides in length, such as at least 10 contiguous nucleotides complementary to a nucleic acid sequence, such as a sequence flanking a gene fusion point or gene fusion nucleic acid sequences disclosed herein. Particular lengths of probes that can be used to practice the methods of the present disclosure include probes having at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, or more contiguous nucleotides complementary to a nucleic acid molecule, for example a first or second nucleic acid that is part of a gene fusion. In a particular example, each nucleic acid probe is at least 30 nucleotides in length. In one non-limiting example, each nucleic acid probe is about 40 nucleotides in length. In a particular example, each nucleic acid probe is about 50 nucleotides in length.

Conditions resulting in particular degrees of hybridization (stringency) will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. In some examples, the probes utilized in the disclosed methods have a melting temperature ($T_m$) of at least about 37° C., at least about 42° C., at least about 45° C., 50° C., at least about 55° C., at least about 60° C., at least about 65° C., at least about 70° C., at least about 75° C., at least about 80° C., such as about 37° C.-80° C. (for example, about 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80° C.). Methods of calculating the $T_m$ of a probe are known to one of skill in the art (see e.g., Sambrook et al., *Molecular Cloning: A Laboratory Manual*, 3d ed., Cold Spring Harbor Press, 2001, Chapter 10).

Also provided are probes that are degenerate at one or more positions (such as 1, 2, 3, 4, 5, or more positions), for example, a probe that includes a mixture of nucleotides (such as 2, 3, or 4 nucleotides) at a specified position in the probe. In some examples, the probes disclosed herein include one or more synthetic bases or alternative bases (such as inosine). In other examples, the probes disclosed herein include one or more modified nucleotides or nucleic acid analogues, such as one or more locked nucleic acids (see, e.g., U.S. Pat. No. 6,794,499) or one or more peptide nucleic acids. In some examples, use of one or more locked nucleic acids or peptide nucleic acids in the probe can increase the $T_m$ of the probe relative to the $T_m$ of a probe of the same length and composition which does not include the modified nucleic acid.

A. Exemplary Gene Fusions

The disclosed methods can be used to detect the presence of a gene fusion in a sample from a subject. Gene fusions are well known to one of skill in the art. Gene fusions may produce a gene product with a new or different function than that of either of the two fusion partners. In other examples, a gene fusion includes an intact or mostly intact gene sequence fused to a promoter from another gene, for example a strong promoter that upregulates expression of the gene sequence. In some examples, a gene fusion is an oncogene. Table 1 provides exemplary genes involved in gene fusions and exemplary gene fusions. Other gene fusions, including those not yet identified, can be detected by one of skill in the art utilizing the methods disclosed herein.

TABLE 1

Exemplary genes and gene fusions

| Fusion gene | Gene 1 | Accession No. | Gene 2 | Accession No. | Fusion Accession No. | Associated Tumor |
|---|---|---|---|---|---|---|
| ABL1/BCR | ABL1 | | BCR | | | CML, ALL, |
| BCR/ABL1 | BCR | Hs.446394 | ABL1 | Hs.446504 | AF113911, AJ131466, AJ131467, AY043457, M13096, M25946 | ALL, CML, |
| DDX5/PRKCB | DDX5 | Hs.279806 | PRKCB | Hs.349845 | CD683976 | Nasopharynx |
| CCDC134/ZNF75A | CCDC134 | Hs.474991 | ZNF75A | Hs.513292 | CD691174 | |
| COL3A1/GRSF1 | COL3A1 | Hs.443623 | GRSF1 | Hs.309763 | AW081998 | Esophagus, squamous cell carcinoma |
| IREB2/OXR1 | IREB2 | Hs.370324 | OXR1 | Hs.432398 | AK127563 | Tongue |
| MYB/NFIB | MYB | | NFIB | | FJ969915, FJ969916, FJ969917 | Head and neck, breast |
| TMPRSS2/ERG | TMPRSS2 | | ERG | | DQ831521, DQ204772, DQ204773 | Prostate TMPRSS2 |
| TMPRSS2/ETV4 | TMPRSS2 | | ETV4 | | DQ396625 | Prostate |
| EWSR1/FLI1 | EWSR1 | Hs.374477 | FLI1 | Hs.257049 | AF327066 | Ewing sarcoma |
| EML4/ALK | EML4 | NM_019063 | ALK | NM_004304 | | Lung carcinoma |

B. Fusion Probes

In some embodiments, the probe is a fusion probe, which hybridizes to a portion of each gene included in the gene fusion and spans the fusion point. The fusion probe includes at least two parts, such that the 5' portion of the probe is capable of hybridizing to the first gene and the 3' portion of the probe is capable of hybridizing to the second gene. In some examples, a fusion probe is about 10-200 nucleotides in length (including but not limited to about 20-100, 25-50, or 30-45 nucleotides in length and others as described above) In other examples, a fusion probe is at least about 10, 15, 20, 25, 30, 35, 40, 45, 50, 60, 70, 80, 90, 100, 110, 120, 130, 14, 150, 160, 170, 180, 190, 200, or more nucleotides in length.

In some examples the 5' portion and 3' portion of the fusion probe are the same or a similar length (for example, the 5' portion is at least 9 nucleotides long, such as about 9-25 nucleotides long and the 3' portion is at least 9 nucleotides long, such as about 9-25 nucleotides long). In particular examples, the 5' portion of the probe is 9, 10, 11, 12, 13, 14, 15, 16, 17, 18, 19, 20, 21, 22, 23, 24, 25, or more nucleotides long, and the 3' portion of the probe is the same number of nucleotides. In other examples, the 5' portion and the 3' portion are not the same or a similar length. In some examples, the 5' portion of the probe is 9, 10, 11, 12, 13, 14, 15, 16, 17, 18, 19, 20, 21, 22, 23, 24, 25, or more nucleotides long, and the 3' portion of the probe is about 1-20 (such as 1, 2, 3, 4, 5, 6, 7, 8, 9, 10, 11, 12, 13, 14, 15, 16, 17, 18, 19, or 20) nucleotides shorter or longer than the 5' portion of the probe.

In further examples, the 5' portion of the probe or the 3' portion of the probe is very short, for example about 1-10 nucleotides long, while the other portion of the probe is a length similar to that described above (for example at least 9 nucleotides long, such as about 9-50 nucleotides long). In particular examples, the 5' portion of the probe is at least about 1-10 nucleotides long (such as at least 1, at least 2, at least 3, at least 4, at least 5, at least 6, at least 7, at least 8, at least 9, or at least 10 nucleotides long) and the 3' portion of the probe is about at least 9 nucleotides long, such as at least about 9-50 nucleotides long (such as at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides). In other examples, the 3' portion of the probe is at least about 1-10 nucleotides long (such as at least 1, at least 2, at least 3, at least 4, at least 5, at least 6, at least 7, at least 8, at least 9, or at least 10 nucleotides long) and the 5' portion of the probe is about at least 9 nucleotides long, such as at least about 9-50 nucleotides long (such as at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides). In one example, the 5' portion of the probe is about 1-3 bases long and the 3' portion of the probe is at least about 10 nucleotides long (such as at least about 10-200, at least about 10-100, or at least about 10-50 nucleotides long) or vice versa. In other examples, the 5' portion of the probe is about 3-10 bases long and the 3' portion of the probe is at least about 25 nucleotides long (such as about 25-200, at least about 25-100, or at least about 25-50 nucleotides long).

In some examples, different gene fusions may contain a common portion (for example distinct gene fusions may include the same or a similar 5' portion, but different 3' portions, or vice versa), and the difference in the point of fusions that varies may only vary by a few bases (for example, 20 or less, such as 20, 19, 18, 17, 16, 15, 14, 13, 12, 11, 10, 9, 8, 7, 6, 5, 4, 3, 2, or 1 base). In some examples, the fusion probe is designed in order to discriminate the fusions, for example by slightly offsetting the probe such that the bases which are different between fusions are internal to the sequence that is captured or hybridizes to the programming linker, such that the either the mismatched probe or the mismatched target bases will be hydrolyzed by the nuclease, and then the short matched region left will melt and be hydrolyzed, thus preventing the mismatched probe from being captured. In this way, programming linkers can be utilized to distinguish the gene fusions (for example, based on spatial location on an array). Alternatively, the probe can be designed to have only a few bases covering the sequence that differs between fusions, with the label located at that end such that it is protected when the sequence is hybridized, and otherwise hydrolyzed and thus not detected, and it is captured by the common gene sequence, such that all probes are captured, but only the correctly matched probes produce a detectable signal.

Exemplary fusion probes include those shown in Table 2. Other exemplary fusion probes are shown in Tables 4, 7, and 8 (below). One of skill in the art can design fusion probes for any gene fusion where the fusion point of the two genes is known, for example those provided in Table 1, above.

TABLE 2

Exemplary fusion probes

| Gene 1 (5') | Gene 2 (3') | Fusion Gene Accession No. | Fusion Probe Sequence (5'–> 3')* | Tm | SEQ ID NO: |
|---|---|---|---|---|---|
| DDX5 | PRKCB | CD683976 | gggaccgagggtCATGCTTTCAGAACG | 61.3 | 1 |
| CCDC134 | ZNF75A | CD691174 | gcctggagatctCATTGTTTGTGC | 53.8 | 2 |
| COL3A1 | GRSF1 | AW081998 | gaaatgcttcttgcTTCACCCTTAGC | 54.8 | 3 |
| IREB2 | OXR1 | AK127563 | ctaaacttggcaccaAGTATGAGATATAG | 52.7 | 4 |
| CRTC1 | MAML2 | AY040324 | gccgcgcggCTCCAGGGTTCC | 62.6 | 5 |
| MYB | NFIB var. 1 | FJ969915 | gcgagcccccttgcagCTGAGGATT | 60 | 6 |
|  |  |  | cgagcccccttgcagCTGAGGATTT | 58.2 | 7 |
|  |  |  | gagcccccttgcagCTGAGGATTTG | 57 | 8 |
|  |  |  | agcccccttgcagCTGAGGATTTGT | 57.6 | 9 |
|  |  |  | gcccccttgcagCTGAGGATTTGTG | 57.5 | 10 |
|  |  |  | cccccttgcagCTGAGGATTTGTGA | 56.3 | 11 |
|  |  |  | ccccttgcagCTGAGGATTTGTGAC | 55.5 | 12 |
| MYB | NFIB var. 2 | FJ969916 | cgagcccccttgcagTCCTGGTACC | 60 | 13 |
|  |  |  | gagcccccttgcagTCCTGGTACCT | 58 | 14 |
|  |  |  | agcccccttgcagTCCTGGTACCTG | 59.1 | 15 |
|  |  |  | gcccccttgcagTCCTGGTACCTGG | 59.9 | 16 |
|  |  |  | cccccttgcagTCCTGGTACCTGGG | 59.6 | 17 |
| MYB | NFIB var. 3 | FJ969917 | gcgagcccccttgcagCCTAACGGC | 62.7 | 18 |
|  |  |  | cgagcccccttgcagCCTAACGGCA | 61.9 | 19 |
|  |  |  | gagcccccttgcagCCTAACGGCAG | 60.5 | 20 |
|  |  |  | agcccccttgcagCCTAACGGCAGT | 61.1 | 21 |
|  |  |  | gcccccttgcagCCTAACGGCAGTG | 61 | 22 |
|  |  |  | cccccttgcagCCTAACGGCAGTGG | 60.7 | 23 |
| TMPRSS2 | ERG | EU090248 | tggagcgcggcagGTTATTCCAGG | 60 | 24 |
|  |  |  | ggagcgcggcagGTTATTCCAGGA | 59.8 | 25 |
|  |  |  | gagcgcggcagGTTATTCCAGGAT | 58.1 | 26 |
| TMPRSS2 | ETV4 | EU693079 | ttgaactcagtctCGGCCCCCGCT | 60.8 | 27 |
|  |  |  | tgaactcagtctCGGCCCCCGCTT | 60.8 | 28 |
|  |  |  | gaactcagtctCGGCCCCCGCTTG | 60.5 | 29 |
| EWSR1 | FLI1 | JF290489 | tacgggcagcagaACCCTTCTTAT | 54.8 | 30 |
|  |  |  | acgggcagcagaACCCTTCTTATG | 56.2 | 31 |
|  |  |  | cgggcagcagaACCCTTCTTATGA | 56 | 32 |

*Lower case, gene 1; upper case, gene 2

C. Flanking Probes

In some embodiments, the probe is a "flanking" probe, which hybridizes to a portion of the full-length gene, a portion of which is included in the gene fusion. The flanking probes are complementary to sequence present in the wild type gene and may also be complementary to sequence present in the gene fusion. This is presented schematically in FIG. 3. A "5' flanking probe" is a probe that is complementary to a sequence that is 5' of a fusion point or breakpoint in the wild-type (non-fusion) gene (for example, 5' probe 1 or 5' probe 2 in FIG. 3). A "3' flanking probe" is a probe that is complementary to a sequence that is 3' of a fusion point or a breakpoint in the wild type (non-fusion) gene (for example, 3' probe 1 or 3' probe 2 in FIG. 3). In some examples, a fusion probe is about 10-200 nucleotides in length (including but not limited to about 20-100, 25-50, or 30-45 nucleotides in length and others as described above)

In other examples, a fusion probe is at least about 10, 15, 20, 25, 30, 25, 40, 45, 50, 60, 70, 80, 90, 100, 110, 120, 130, 14, 150, 160, 170, 180, 190, 200, or more nucleotides in length.

In some embodiments, a fusion between two genes is known to occur and the fusion point is also known. Flanking probes can be designed to be complementary to the 5' gene in the fusion (Gene 1 in FIG. 3) at points 5' and 3' to the known fusion point. Likewise, flanking probes can be designed to be complementary to the 3' gene in the fusion (Gene 2 in FIG. 3) at points 5' and 3' to the fusion point. Exemplary flanking probes are provided in Tables 3 and 8.

In other embodiments, a fusion between two genes is not known to occur, or a fusion is known to occur, but the fusion point is not known. In such cases, it is desirable to design the flanking probes as close to the 5' end and 3' end of the gene of interest, in order to increase the likelihood that the fusion point is between the flanking probes.

TABLE 3

Exemplary flanking probes

| Gene | Accession No. | Flanking Probe Sequence (5' -> 3') | $T_m$ | SEQ ID NO: |
|---|---|---|---|---|
| DDX5 | NM_004396 | | | |
| DDX5 5'flanking | | ATAGAGCGGCTCCCAGCGTTCCCTGCGGC GTAGGAGGCGGTCCAGACTAT | 77.9 | 33 |
| | | GCGGCCGGCACCTCATTCATTTCTACCGG TCTCTAGTAGTGCAGCTTCGG | 74.4 | 34 |
| | | CAAGGCTTCGCCGTCATCGAGGCCATTTC CAGCGACTTGTCGCACGCTTT | 76.2 | 35 |
| DDX5 3' flanking | | GTGCTGGCACCAACTCGGGAACTGGCCCA ACAGGTGCAGCAAGTAGCTGC | 77 | 36 |
| | | CAATCTGAGAAGAACAACCTACCTTGTCC TTGATGAAGCAGATAGAATGC | 67.6 | 37 |
| | | GCAATTAATCCCAAGTTGCTTCAGTTGGT CGAAGACAGAGGTTCAGGTCG | 70.8 | 38 |
| PRKCB | NM_002738 | | | |
| PRKCR 5' flanking | | GTCACATTCTCCTGCCCTGGCGCTGACAA GGGTCCAGCCTCCGATGACCC | 77.4 | 39 |
| | | GTGACACCTGCATGATGAATGTGCACAAG CGCTGCGTGATGAATGTTCCC | 73.2 | 40 |
| | | CCGCATCTACATCCAGGCCCACATCGACA GGGACGTCCTCATTGTCCTCG | 75.5 | 41 |
| PRKCB 3' flanking | | GAAAGACAAGAGGCTTGCAAGGACCCTG AAGAGGTCGGAGCATCATACAG | 71.9 | 42 |
| | | CTCATGAGATGGTATCAGCCACCCAATGA CTGGCGTATCTTGGTCCTGTG | 71.9 | 43 |
| | | GAGAGACACCTCCAACTTCGACAAAGAGT TCACCAGACAGCCTGTGGAAC | 72.1 | 44 |
| CCDC134 | NM_024821 | | | |
| CCDC134 5' flanking | | CTTTCAGTTGCTTTGCTGTTAGCCrGTTGG ACCTTCGAGCCTAGCTGCT | 72.2 | 45 |
| | | CACAGGACTCGGCCACCTGCCCTTCCTGC ACCGACTGGCCAGCTCAAGA | 78.2 | 46 |
| | | GTCTGGGATGGGAGCCACAGGCACCTTGA GGACCTCCCTGGACCCAAGCC | 78.1 | 47 |
| CCDC134 3' flanking | | GGAGGCAGGTCGGGAGGAAGAAGAGGTG GAGGTGTGGTTGTGGTGGAGAG | 76.2 | 48 |
| | | CCTGCCTGGACCCTGTTGGTGGCTGAAGA CCTCTGGCCAGCTGGCTTCCG | 78.3 | 49 |
| | | CAGCAGAACTAGGTTCTGAGCCACGGGTC AGGGTGCCACCCTGCTGCTGG | 77.3 | 50 |
| ZNF75A | NM_153028 | | | |
| ZNF75A 5' flanking | | CAAGCTGGCCGAGGTTGCAGTCCATGAGC TGGGAAAGGAGGCAGTGCTCT | 76.3 | 51 |
| | | TTGGGAGAAACAGCAGAGGCCTCAAGTTT CGGGCTGAAGCCAACAGAGTC | 73.9 | 52 |
| | | GTTTCGGGCTGAAGCCAACAGAGTCCCAA CCAGTGGGCGTATCCCAAGAT | 74.8 | 53 |
| ZNF75A 3' flanking | | CTGCAGCCACTCAGTAGTCTTCTGTGGTC ACAGAAGTAAACATTGTTGGC | 70.5 | 54 |
| | | GCAGGCTTACCAATTTCCATAGTCTCATG AGGCCGAAATGAATTACAATG | 68.1 | 55 |
| | | CCACTAGGGAATCTCCAGATGAACTATTA ATGCACTGTCTTATGCCTCTC | 67.7 | 56 |

TABLE 3-continued

Exemplary flanking probes

| Gene | Accession No. | Flanking Probe Sequence (5' -> 3') | $T_m$ | SEQ ID NO: |
|---|---|---|---|---|
| COL3A1 | NM_000090 | | | |
| COL3A1 5' flanking | | TTTATGACGGGCCCGGTGCTGAAGGGCAGGGAACAACTTGATGGTGCTAC | 74.9 | 57 |
| | | GAAGGAGGATGTTCCCATCTTGGTCAGTCCTATGCGGATAGAGATGTCTG | 70.4 | 58 |
| | | GCCAGAACCATGCCAAATATGTGTCTGTGACTCAGGATCCGTTCTCTGCG | 72.3 | 59 |
| COL3A1 3' flanking | | CAAGGGTGAAAGTGGGAAACCAGGAGCTAACGGTCTCAGTGGAGAACGTG | 73.2 | 60 |
| | | GTCCTTGATGTGCAGCTGGCATTCCTTCGACTTCTCTCCAGCCGAGCTTC | 73.8 | 61 |
| | | CACCCTATGACATTGGTGGTCCTGATCAAGAATTTGGTGTGGACGTTGGC | 71.9 | 62 |
| GRSF1 | NM_002092 | | | |
| GRSF1 5' flanking | | CCCAACCGGCCCTGGATTCCACTTCCGTTCCACCATCGCTGCTGGAGCAG | 77.8 | 63 |
| | | CTTTCTCATTCGAGCTCAAGGACTGCCCTGGTCATGCACTATGGAAGATG | 71.1 | 64 |
| | | TGCAGAAAGCCTTAGAGAAGCACCGCATGTACATGGGCCAGCGGTATGTG | 73.8 | 65 |
| GRSF1 3' flanking | | TTTAGCCTAGCTGCTGCTTACGGAGTGCAAGGGAGAACTCTGAGAAGCAG | 72.1 | 66 |
| | | GAGCCATGACTGTTGCTGCACTCCAGCCTGAGTGACAGAGTGAGACCCTG | 74.5 | 67 |
| | | GAGATGGAGTCTTGTATCGCCCAGGCTAGAGTGCAGTGGCCTGGTCTTGG | 74.1 | 68 |
| IREB2 | NM_004136 | | | |
| IREB2 5' flanking | | GCTGGCTCTGCTGCTCTCGCGATATTTGCGCGAGCCTGCTTCCTTCTTTC | 74.8 | 69 |
| | | CTGCTCTCGCGATATTTGCGCGCGAGCCTGCTTCCTTCTTTCCTCCCTTGCC | 74.8 | 70 |
| | | TATTTGCGCGAGCCTGCTTCCTTCTTTCCTCCCTTGCCAGTCCGCCTGTC | 75.5 | 71 |
| IREB2 3' flanking | | GACTACCTGCCGAGGATCTTGTGATTCTGGAGAACTAGGCCGAAACTCAG | 71.5 | 72 |
| | | ATCTTGCCTCTCCACCCTTAGTGGTAGCTTATGCCATAGCAGGCACAGTG | 72.1 | 73 |
| | | GGTTCCCTCCACATATGAAGATGGACCATGGCAGGATACAACTGATTGTG | 70.4 | 74 |
| OXR1 | NM_018002 | | | |
| OXR1 5' flanking | | GTGTTGTCGACTGACCTGCTAATTTCCTGTTCTGGAATCGAGAGAAGAC | 69.5 | 75 |
| | | CTCCAGGGTTCAACCCTTTGGCTGGTGCAGGAAAAGCAAACACCACAAGCC | 74.9 | 76 |
| | | GGTATTCGACCTGCACGAGTTGTATCTTCAACTTCTGAGGAGGAGGAAGC | 70.8 | 77 |
| OXR1 3' flanking | | CTGTTATACATGTGACAGTGACTTTGTGCTGAAATTTCAGCTATTCCAGA | 66.7 | 78 |
| | | TTTGTTCTTACAGAAAGTGTTGATTGCCAGGTTGCTTATAGCACTTTAAG | 66.2 | 79 |
| | | CTTCGGTCTTCCACAGCAGTATTATTGTCTTTGTGGAGTTGACTAATGAT | 67.4 | 80 |
| CRTC1 | NM_015321 | | | |
| CRTC1 5' flanking | | GAGGTGGCGGCGAGAAGATGGCGACTTCGAACAATCCGCGGAAATTCAGC | 75.3 | 81 |
| | | GGCGAGAAGATGGCGACTTCGAACAATCCGCGGAAATTCAGCGAGAAGAT | 73.2 | 82 |
| | | TGGCGACTTCGAACAATCCGCGGAAATTCAGCGAGAAGATCGCGCTGCAC | 75.2 | 83 |
| CRTC1 3' flanking | | GCTCCCATCACCTTCACTGGGTCCCGATGGAGCCGTCTCAGAGGCCGAGG | 77.8 | 84 |
| | | CCAAGTGTCCTGTTCCCTGCGGCCCTTGGCCTTCCAGGGTCCTGGCCAGG | 79.4 | 85 |
| | | GGTGCTGGCTCTGATGATTCCAGAGCCTGTATCCACCTTCTGGGCTCCTG | 74.2 | 86 |
| MAML2 | NM_032427 | | | |
| MAML 2 5' flanking | | CTCCCTCTCCTATCGGAGCACAATGAAAGCCTGTGTATCGCCGTGACTCC | 73.4 | 87 |
| | | CAGACTTGCCTGCAATAGCCAGCAGTAGCCTCTTTCCACCTCACCATCCC | 736. | 88 |
| | | CACCACCTGAGCTGTGAAGGACGATATGAACGAGGTAGGGCCGAGAGCTC | 74.1 | 89 |

TABLE 3-continued

Exemplary flanking probes

| Gene | Accession No. | Flanking Probe Sequence (5' -> 3') | T$_m$ | SEQ ID NO: |
|---|---|---|---|---|
| MAML 2 3'flanking | | CAACAAACTCCTTAATTTGCTCTAATAGATAGGTATGGTTTAATCTTTCC | 62.9 | 90 |
| | | CTTGCAGGATAGATTGAAATGTTATAGGTTTGTTTGGAGTAACCAAACAG | 65.4 | 91 |
| | | TTTCCCACAATCCTCTACTTCAGTGGGATGCTGTGTCTAOTGATTAAACA | 68.7 | 92 |
| MYB | NM_005375 | | | |
| MYB 5' flanking | | CTCCTCCGTGACCTCCTCCTCCTCTTTCTCCTGAGAAACTTCGCCCCAGC | 74.9 | 93 |
| | | CCCGGCACAGCATATATAGCAGTGACGAGGATGATGAGGACTTTGAGATG | 70.7 | 94 |
| | | TGTGTGACCATGACTATGATGGGCTGCTTCCCAAGTCTGGAAAGCGTCAC | 73 | 95 |
| MYB 3' flanking | | GGGAGACAGAAACTGTGGTTGATAGCCAGTCACTGCCTTAAGAACATTTG | 69.7 | 96 |
| | | GATAGCCAGTCACTGCCTTAAGAACATTTGATGCAAGATGGCCAGCACTG | 70.6 | 97 |
| | | AGCCAGTCACTGCCTTAAGAACATTTGATGCAAGATGGCCAGCACTGAAC | 71.6 | 98 |
| NFIB | NM_001190737 | | | |
| NFIB 5' flanking | | GCACGCCGAGTGAACTTGAATCTTTGGCTATTTAAGGAGGACTGGGTTTG | 70.8 | 99 |
| | | CATTCATCGAGGCACTTCTTCCACATGTCCGTGCAATTGCCTATACTTGG | 70.8 | 100 |
| | | CCTTGCCAAACTGCGCAAAGATATTCGCCAGGAGTATCGAGAGGACTTTG | 71.5 | 101 |
| NFIB 3' flanking | | GCATCAGCCAAACTCATTGCCATGACAACTCTTTGTACTGTGTCCGTGCC | 72.1 | 102 |
| | | GTACAACTGTAGGTGACGAGTAGTCAGTTATTGCTTGCTAGCTACACACC | 68.8 | 103 |
| | | CAGCCTATACTGCTAGCAGCTGCTCATACTGCAGTCAATTACTGGAAGCG | 70.5 | 104 |
| EWSR1 | NM_013986 | | | |
| EWSR1 5' flanking | | CAGCGGACGGAACCATTCCAAACAGCCTAGTCTCGTGCTGAGAGCCTCTC | 74.4 | 105 |
| | | GTGTCACGTCGGGCGCTCTTTAGAGAGGACTGGGACAAGAGTTGCGGACG | 75.5 | 106 |
| EWSR1 3' flanking | | GGCGAGCACCGTCAGGAGCGCAGAGATCGGCCCTACTAGATGCAGAGACC | 76.5 | 107 |
| | | TGTGAGCATGCTCAGTATCATTGTGGAGAACCAAGAGGGCCTCTTAACTG | 70.7 | 108 |
| | | GTATCATTGTGGAGAACCAAGAGGGCCTCTTAACTGTAACAATGTTCATG | 67.8 | 109 |
| FLI1 | NM_002017 | | | |
| FLI1 5' flanking | | GTTTCATCCGGTTAACTGTCTCTTTCGCTCCGCTACAACAACAAACGTGC | 71.2 | 110 |
| | | GGGACTATTAAGGAGGCTCTGTCGGTGGTGAGCGACGACCAGTCCCTCTT | 74.7 | 111 |
| | | GCAGGAGTGGATCAATCAGCCAGTGAGGGTCAACGTCAAGCGGGAGTATG | 73.8 | 112 |
| FLI1 3' flanking | | CTTCTTAGGGTAACACTAAGTACCTTCTAGACAACATGTCTACCTAAATG | 64.8 | 113 |
| | | GGGTAACACTAAGTACCTTCTAGACAACATGTCTACCTAAATGAAATGGG | 66.1 | 114 |
| | | CAACATGTCTACCTAAATGAAATGGGATGTGTTTCGGAACATTTGTCTCC | 67.5 | 115 |
| TMPRSS2 | NM_005656 | | | |
| TMPRSS2 5' flanking | | GAGTAGGCGCGAGCTAAGCAGGAGGCGGAGGCGGAGGCGGAGGGCGAGGG | 80.8 | 116 |
| | | GCGCGGCAGGTCATATTGAACATTCCAGATACCTATCATTACTCGATGCT | 69.9 | 117 |
| TMPRSS2 3' flanking | | CACTACTCTACCATGGTTCTGCCTCCTGGCCAAGCAGGCTGGTTTGCAAG | 73.9 | 118 |
| | | GAATGATTCTACAGCTAGGACTTAACCTTGAAATGGAAAGTCATGCAATC | 66 | 119 |
| | | CTGTAGAGAGCAGCATTCCCAGGGACCTTGGAAACAGTTGGCACTGTAAG | 72 | 120 |
| ETV4 | NM_001079675 | | | |
| ETV4 5' flanking | | CCGGCCGTGCGGCCGGAGGGAGCGGCCGGATGGAGCGGAGGATGAAAGCC | 82.7 | 121 |
| | | GGATGAAAGCCGGATACTTGGACCAGCAAGTGCCCTACACCTTCAGCAGC | 73.9 | 122 |
| | | CCTTCAGCAGCAAATCGCCCGGAAATGGGAGCTTGCGCGAAGCGCTGATC | 76.3 | 123 |

TABLE 3-continued

Exemplary flanking probes

| Gene | Accession No. | Flanking Probe Sequence (5' -> 3') | $T_m$ | SEQ ID NO: |
|---|---|---|---|---|
| ETV4 3' flanking | | CTTTCTTCTGCCCTTTCCTAGGCCCAGGCCTGGGTTTGTACTTCCACCTC | 73.7 | 124 |
| | | CTAGGCCCAGGCCTGGGTTTGTACTTCCACCTCCACCACATCTGCCAGAC | 75.4 | 125 |
| | | GGGTTTGTACTTCCACCTCCACCACATCTGCCAGACCTTAATAAAGGCCC | 72.1 | 126 |
| ERG | NM_004449 | | | |
| ERG 5' flanking | | GGGAGAGTGTGCAAGAGATCGCTGCGGGACAGGTTCCTAGAGATCGCTCC | 74.9 | 127 |
| | | CCCGAGGGACATGAGAGAAGAGGAGCGGCGCTCAGGTTATTCCAGGATCT | 74.6 | 128 |
| | | GAGCGGCGCTCAGGTTATTCCAGGATCTTTGGAGACCCGAGGAAAGCCGT | 75.3 | 129 |
| ERG 3' flanking | | GCACTGTGGCTTGGGATTCACTAGCCCTGAGCCTGATGTTGCTGGCTATC | 73.7 | 130 |
| | | CCTTCTGCACAGATGTGGCACCTGCAACCCAGGAGCAGGAGCCGGAGGAG | 77.3 | 131 |
| | | CAGCAGGTGCAGCAGAGATGGCTACAGCTCAGGAGCTGGGAAGGTGATGG | 75.2 | 132 |

VII. Samples

The samples of use in the disclosed methods include any specimen that includes nucleic acid (such as genomic DNA, cDNA, viral DNA or RNA, rRNA, tRNA, mRNA, oligonucleotides, nucleic acid fragments, modified nucleic acids, synthetic nucleic acids, or the like). In particular examples, the sample includes mRNA. In some examples, the disclosed methods include obtaining the sample prior to analysis of the sample. In some examples, the disclosed methods include selecting a subject having a tumor, and then in some examples further selecting the target gene fusion to detect based on the subject's tumor (e.g., see Table 1).

Appropriate samples include any conventional environmental or biological samples, including clinical samples obtained from a human or veterinary subject. Exemplary samples include, without limitation, cells, cell lysates, blood smears, cytocentrifuge preparations, cytology smears, bodily fluids (e.g., blood, plasma, serum, saliva, sputum, urine, bronchoalveolar lavage, semen, etc.), tissue biopsies (e.g., tumor biopsies), fine-needle aspirates, and/or tissue sections (e.g., cryostat tissue sections and/or paraffin-embedded tissue sections). In other examples, the sample includes circulating tumor cells or circulating fetal cells in maternal blood. In particular examples, samples are used directly (e.g., fresh or frozen), or can be manipulated prior to use, for example, by fixation (e.g., using formalin) and/or embedding in wax (such as formalin-fixed paraffin-embedded (FFPE) tissue samples).

In further examples, a sample includes a specimen including bacterial or viral nucleic acids, for example a sample from a subject infected with a virus or bacterium. A sample may also include environmental specimens, for example, water, air, soil, dust, wood, or food or other materials that may contain or be contaminated with a pathogen.

Methods of obtaining a sample from a subject are known in the art. For example, methods of obtaining tissue or cell samples are routine. Exemplary samples may be obtained from normal cells or tissues, or from neoplastic cells or tissues. Neoplasia is a biological condition in which one or more cells have undergone characteristic anaplasia with loss of differentiation, increased rate of growth, invasion of surrounding tissue, and which cells may be capable of metastasis. In particular examples, a biological sample includes a tumor sample, such as a sample containing neoplastic cells.

Exemplary neoplastic cells or tissues may be included in or isolated from solid tumors, including lung cancer (e.g., non-small cell lung cancer, such as lung squamous cell carcinoma), breast carcinomas (e.g. lobular and duct carcinomas), adrenocortical cancer, ameloblastoma, ampullary cancer, bladder cancer, bone cancer, cervical cancer, cholangioma, colorectal cancer, endometrial cancer, esophageal cancer, gastric cancer, glioma, granular call tumor, head and neck cancer, hepatocellular cancer, hydatiform mole, lymphoma, melanoma, mesothelioma, myeloma, neuroblastoma, oral cancer, osteochondroma, osteosarcoma, ovarian cancer, pancreatic cancer, pilomatricoma, prostate cancer, renal cell cancer, salivary gland tumor, soft tissue tumors, Spitz nevus, squamous cell cancer, teratoid cancer, and thyroid cancer. Exemplary neoplastic cells may also be included in or isolated from hematological cancers including leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, and myelodysplasia.

For example, a sample from a tumor that contains cellular material can be obtained by surgical excision of all or part of the tumor, by collecting a fine needle aspirate from the tumor, as well as other methods known in the art. In some examples, a tissue or cell sample is applied to a substrate and analyzed to determine presence of a gene fusion. A solid support useful in a disclosed method need only bear the biological sample and, optionally, but advantageously, permit the convenient detection of components (e.g., proteins and/or nucleic acid sequences) in the sample. Exemplary supports include microscope slides (e.g., glass microscope slides or plastic microscope slides), coverslips (e.g., glass coverslips or plastic coverslips), tissue culture dishes, multiwell plates, membranes (e.g., nitrocellulose or polyvinylidene fluoride (PVDF)) or BIACORE chips.

The samples described herein can be prepared using any method now known or hereafter developed in the art. In some examples, cells in the sample are lysed or permeabilized in an aqueous solution (for example using a lysis buffer). The aqueous solution or lysis buffer includes detergent (such as sodium dodecyl sulfate) and one or more chaotropic agents (such as formamide, guanidinium HCl, guanidinium isothiocyanate, or urea). The solution may also contain a buffer (for example SSC). In some examples, the lysis buffer includes about 15% to 25% formamide (v/v) about 0.01% to 0.1% SDS, and about 0.5-6×SSC (for example, about 3×SSC). The buffer may optionally include tRNA (for example, about 0.001 to about 2.0 mg/ml) or a ribonuclease. The lysis buffer may also include a pH indicator, such as Phenol Red. In a particular example, the lysis buffer includes 20% formamide, 3×SSC (79.5%), 0.05% SDS, 1 µg/ml tRNA, and 1 mg/ml Phenol Red.

Cells (or other sample types) are incubated in the aqueous solution for a sufficient period of time (such as about 1 minute to about 60 minutes, for example about 5 minutes to about 20 minutes, or about 10 minutes) and at a sufficient temperature (such as about 22° C. to about 115° C., for example, about 37° C. to about 105° C., or about 90° C. to about 100° C.) to lyse or permeabilize the cell. In some examples, lysis is performed at about 95° C., if the gene fusion nucleic acid to be detected is RNA. In other examples, lysis is performed at about 105° C., if the gene fusion nucleic acid to be detected is DNA. In some examples, lysis conditions can be such that genomic DNA is not accessible to the probes whereas RNA (for example, mRNA) is, or such that the RNA is destroyed and only the DNA is accessible for probe hybridization. In some examples, the lysis step includes incubating the sample at about 95° C. for about 5-15 minutes to denature the RNA in the sample, but not the genomic DNA. In other examples, the lysis step includes incubating the sample at about 105° C. for about 5-15 minutes to denature both the RNA and the genomic DNA in the sample.

In some examples, the crude cell lysate is used directly without further purification. The cells may be lysed in the presence or absence of one or more of the disclosed probes. If the cells are lysed in the absence of probe, the one or more probes can be subsequently added to the crude lysate. In other examples, nucleic acids (such as DNA and/or RNA) are isolated from the cell lysate prior to contacting with one or more of the disclosed probes.

In some examples, tissue samples are prepared by fixing and embedding the tissue in a medium or include a cell suspension is prepared as a monolayer on a solid support (such as a glass slide), for example by smearing or centrifuging cells onto the solid support. In further examples, fresh frozen (for example, unfixed) tissue or tissue sections may be used in the methods disclosed herein. The tissue sections are used in the methods disclosed herein, for example by placing all or a portion of the section in the lysis buffer and proceeding as described for other sample types.

In some examples an embedding medium is used. An embedding medium is an inert material in which tissues and/or cells are embedded to help preserve them for future analysis. Embedding also enables tissue samples to be sliced into thin sections. Embedding media include paraffin, celloidin, OCT™ compound, agar, plastics, or acrylics. Many embedding media are hydrophobic; therefore, the inert material may need to be removed prior to histological or cytological analysis, which utilizes primarily hydrophilic reagents. The term deparaffinization or dewaxing is broadly used herein to refer to the partial or complete removal of any type of embedding medium from a biological sample. For example, paraffin-embedded tissue sections are dewaxed by passage through organic solvents, such as toluene, xylene, limonene, or other suitable solvents. In some examples, a formalin-fixed paraffin embedded sample is not dewaxed prior to cell lysis.

Tissues can be fixed by any suitable process, including perfusion or by submersion in a fixative. Fixatives can be classified as cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation). Additives may also be included in the fixative, such as buffers, detergents, tannic acid, phenol, metal salts (such as zinc chloride, zinc sulfate, and lithium salts), and lanthanum.

The most commonly used fixative in preparing samples for IHC is formaldehyde, generally in the form of a formalin solution (4% formaldehyde in a buffer solution, referred to as 10% buffered formalin). In one example, the fixative is 10% neutral buffered formalin.

The disclosure is further illustrated by the following non-limiting Examples.

EXAMPLES

Example 1

Detection of Bcr-Abl Fusions

This example describes fusion probes for detection of Bcr-Abl fusions and their use in detecting Bcr-Abl fusion nucleic acids.

Fusion probes spanning Bcr-Abl fusions were designed and are provided in Table 4. In vitro transcribed (IVT) mRNA for Bcr-Abl fusion targets was prepared (Table 5). Specific IVT target was added and the signal from an array containing the entire target fusion probes was measured in a checkerboard assay (FIG. 4). IVT target diluted with lysis buffer was incubated with fusion probes at 95° C. for 10-15 minutes, and incubated at 60° C. for 6-16 hours to allow for RNA-probe hybridization. The mixture was treated with S1 nuclease (1:40 dilution in S1 nuclease buffer) at 50° C. for 60-90 minutes to digest unhybridized RNA and probes. The nuclease reaction was stopped (1.6 N NaOH, 0.135 M EDTA pH 8.0) for 15-20 minutes at 95° C. and then the mixture was added to a plate including programming linkers specific for the fusion probes (Table 6) and incubated at 50° C. for 16-24 hours. Detection linkers (Table 6) were then added and incubated at 60° C. for 60-90 minutes. Detection probe was added and incubated at 50° C. for 60-90 minutes, then detection solution was added and incubated at 37° C. for 60 minutes. Luminescent solution was added and the plate was imaged to detect fusion probe binding to the plate.

The probes were generally specific for the intended target (FIG. 4). The probe for E12A2 cross-reacted with E13A2 target, and the probe for E12A3 cross-reacted with E13A3 target. The probes can be re-designed to eliminate this cross-reactivity, which is believed to arise because the specific fusions are very close to one another, with overlapping bases incorporated into the probe sequences.

TABLE 4

Bcr-Abl fusion targets and probes

| Fusion Probe/Target | Fusion Probe Sequence (5'–> 3')* | SEQ ID NO: |
|---|---|---|
| E1A2 | gatgctactggccgctgaagggcttCTGCGTCTCCATGGAAGGCGCCCTC | 133 |
| E1A3 | tagcctaagacccggagcttttcacCTGCGTCTCCATGGAAGGCGCCCTC | 134 |
| E6A2 | gatgctactggccgctgaagggcttTTTTCCAGAGAGTTCTTGGTCGTTGG | 135 |
| E6A3 | tagcctaagacccggagcttttcacTTTTCCAGAGAGTTCTTGGTCGTTGG | 136 |
| E12A2 | gatgctactggccgctgaagggcttACTTCTTCTGCTGCTCCCGGATGTT | 137 |
| E12A3 | tagcctaagacccggagcttttcacACTTCTTCTGCTGCTCCCGGATGTT | 138 |
| E13A2 | gatgctactggccgctgaagggcttCTTCCTTA/GTTGATGGTCAGCGGAAT | 139 |
| E13A3 | tagcctaagacccggagcttttcacCTTCCTTA/GTTGATGUTCAGCGGAAT | 140 |
| E14A2 | gatgctactggccgctgaagggcttTTGAACTCTGCTTAAATCCAGTGGC | 141 |
| E14A3 | tagcctaagacccggagcttttcacTTGAACTCTGCTTAAATCCAGTGGC | 142 |
| E19A2 | gatgctactggccgctgaagggcttTGACGTCGAAGGCTGCCTTCAGTGC | 143 |
| E19A3 | tagcctaagacccggagcttttcacTGACGTCGAAGGCTGCCTTCAGTGC | 144 |
| E20A2 | gatgctactggccgctgaagggcttCGATGCCCTCTGCGAAGTTGGGGTA | 145 |
| E20A3 | tagcctaagacccggagcttttcacCGATGCCCTCTGCGAAGTTGGGGTA | 146 |

*Lower case, Abl sequence; Upper case, Bcr sequence; Underlined, polymorphic position

TABLE 5

Nucleotide sequences included in IVT Bcr-Abl targets

| Target Fusion | Bcr sequence (nucleotide positions in NM_021574.2) | Abl sequence (nucleotide positions in NM_007313.2) |
|---|---|---|
| E1A2 | 1736-1875 | 576-715 |
| E1A3 | 1736-1875 | 750-900 |
| E6A2 | 2378-2517 | 576-715 |
| E6A3 | 2378-2517 | 750-900 |
| E12A2 | 3059-3198 | 576-715 |
| E12A3 | 3059-3198 | 750-900 |
| E13A2 | 3164-3303 | 576-715 |
| E13A3 | 3164-3303 | 750-900 |
| E14A2 | 3239-3378 | 576-715 |
| E14A3 | 3239-3378 | 750-900 |
| E19A2 | 3647-3786 | 576-715 |
| E19A3 | 3647-3786 | 750-900 |
| E20A2 | 3782-3921 | 576-715 |
| E20A3 | 3782-3921 | 750-900 |

TABLE 6

Programming linkers and detection linkers for Bcr-Abl assay

| Fusion | Sequence (5'-> 3')* | SEQ ID NO: |
|---|---|---|
| Programming linkers | | |
| E1A2 | GCGCTCCCACAACGCTCGACCGGCGGAGGGCGCCTTCCATGGAGACGCAG | 147 |
| E1A3 | GCGCTCCCACAACGCTCGACCGGCGGAGGGCGCCTTCCATGGAGACGCAG | 148 |
| E6A2 | GGACGCCGTCCGGTCCTCACGTGGACCAACGACCAAGAACTCTCTGGAAA | 149 |
| E6A3 | GGACGCCGTCCGGTCCTCACGTGGACCAACGACCAAGAACTCTCTGGAAA | 150 |
| E12A2 | GCAGCGCACGTGCTCAGCCGTAGTGAACATCCGGGAGCAGCAGAAGAAGT | 151 |
| E12A3 | GCAGCGCACGTGCTCAGCCGTAGTGAACATCCGGGAGCAGCAGAAGAAGT | 152 |
| E13A2 | CCACGTCCCTTCCTAGAGACGCTTAATTCCGCTGACCATCAATAAGGAAG | 153 |
| E13A3 | CCACGTCCCTTCCTAGAGACGCTTAATTCCGCTGACCATCAACAAGGAAG | 154 |
| E14A2 | TGGCTGTAGAACACGCGAGCGGTTCGCCACTGGATTTAAGCAGAGTTCAA | 155 |
| E14A3 | TGGCTGTAGAACACGCGAGCGGTTCGCCACTGGATTTAAGCAGAGTTCAA | 156 |
| E19A2 | CTGGCAGCCACGGACGCGAACGAGGCACTGAAGGCAGCCTTCGACGTCA | 157 |
| E19A3 | CTGGCAGCCACGGACGCGAACGAGGCACTGAAGGCAGCCTTCGACGTCA | 158 |
| E20A2 | GCGGACTGTGGTACCATGCCGACCGTACCCCAACTTCGCAGAGGGCATCG | 159 |
| E20A3 | GCGGACTGTGGTACCATGCCGACCGTACCCCAACTTCGCAGAGGGCATCG | 160 |
| Detection Linker | | |
| E1A2 | AAGCCCTTCAGCGGCCAGTAGCATCTGCTCTCCTTCACTGTTTGGAGGTG | 161 |
| E1A3 | GTGAAAAGCTCCGGGTCTTAGGCTATGCTCTCCTTCACTGTTTGGAGGTG | 162 |
| E6A2 | AAGCCCTTCAGCGGCCAGTAGCATCTGCTCTCCTTCACTGTTTGGAGGTG | 163 |
| E6A3 | GTGAAAAGCTCCGGGTCTTAGGCTATGCTCTCCTTCACTGTTTGGAGGTG | 164 |
| E12A2 | AAGCCCTTCAGCGGCCAGTAGCATCTGCTCTCCTTCACTGTTTGGAGGTG | 165 |
| E12A3 | GTGAAAAGCTCCGGGTCTTAGGCTATGCTCTCCTTCACTGTTTGGAGGTG | 166 |
| E13A2 | AAGCCCTTCAGCGGCCAGTAGCATCTGCTCTCCTTCACTGTTTGGAGGTG | 167 |
| E13A3 | GTGAAAAGCTCCGGGTCTTAGGCTATGCTCTCCTTCACTGTTTGGAGGTG | 168 |
| E14A2 | AAGCCCTTCAGCGGCCAGTAGCATCTGCTCTCCTTCACTGTTTGGAGGTG | 169 |
| E14A3 | GTGAAAAGCTCCGGGTCTTAGGCTATGCTCTCCTTCACTGTTTGGAGGTG | 170 |
| E19A2 | AAGCCCTTCAGCGGCCAGTAGCATCTGCTCTCCTTCACTGTTTGGAGGTG | 171 |
| E19A3 | GTGAAAAGCTCCGGGTCTTAGGCTATGCTCTCCTTCACTGTTTGGAGGTG | 172 |

TABLE 6-continued

Programming linkers and detection linkers for Bcr-Abl assay

| Fusion | Sequence (5'-> 3')* | SEQ ID NO: |
|---|---|---|
| E20A2 | AAGCCCTTCAGCGGCCAGTAGCATCTGCTCTCCTTCACTGTTTGGAGGTG | 173 |
| E20A3 | GTGAAAAGCTCCGGGTCTTAGGCTATGCTCTCCTTCACTGTTTGGAGGTG | 174 |

Example 2

Directly Labeled Bcr-Abl Fusion Probes

This example describes exemplary methods for detecting a Bcr-Abl fusion gene in a sample utilizing a directly labeled fusion probe. However, one skilled in the art will appreciate that methods that deviate from these specific methods can also be used to successfully detect the presence of a Bcr-Abl gene fusion in a sample.

A fusion probe is synthesized which spans the Bcr-Abl E1/A2 fusion site, including four nucleotides of Bcr sequence and 40 nucleotides of Abl sequence (Table 7). The probe is labeled with biotin at the 5' end or about one to two nucleotides from the 5' end.

TABLE 7

Bcr-Abl E1A2 fusion and "short overlap" fusion probe sequences

| | Sequence (5'->3')* | SEQ ID NO: |
|---|---|---|
| E1A2 fusion point | acgatggcgagggcgccttccatggagacgcagAAGCCCTTCAGCGGCCAGTAGCATCTGACTTTGAGCCTCA | 175 |
| Fusion probe | gcagAAGCCCTTCAGCGGCCAGTAGCATCTGACTTTGAGCCTCA | 176 |

*Lower case, Bcr sequence; Upper case, Abl sequence

A cell sample is lysed with lysis buffer (for example as described above) and the probe (167 pM) is hybridized to the lysed sample. The sample is treated with S1 nuclease to remove non-hybridized nucleic acids as described above. S1 nuclease treatment also removes the non-hybridized portion of the fusion probe hybridized to the wild-type Abl nucleic acid, including the biotin label (for example, see FIG. 2). The remaining fusion probe, which is hybridized to Bcr-Abl fusion nucleic acid is detected utilizing avidin-horseradish peroxidase or avidin-phycoerythrin. Detection of signal indicates the presence of a Bcr-Abl gene fusion in the sample.

Example 3

Detection of EML4-ALK Gene Fusions Utilizing Fusion Probes

This example describes detection of EML4-ALK fusion variants with fusion probes.

In vitro transcribed (IVT) EML4-ALK gene fusion variants were added to 167 pM final concentration of one or more fusion probes complementary to the target sequences provided in Table 8. The sample was heated at 95° C. for 10-15 minutes and then incubated at 60° C. for 6-16 hours for RNA-probe hybridization. S1 nuclease diluted 1:40 in S1 nuclease buffer (0.25 M sodium acetate, pH 4.5, 1.4 M NaCl, 0.225 M ZnSO$_4$, 0.05% KATHON) was added to the sample. The sample was incubated at 50° C. for 60-90 minutes to digest unbound nucleic acids.

TABLE 8

EML-ALK fusion probe target sequences

| Variant | Target Sequence (5'-> 3') | SEQ ID NO: |
|---|---|---|
| EML4-ALK-v1 | TAGAGCCCACACCTGGGAAAGGACCTAAAGTGTACCGCCGGAAGCACCAG | 177 |
| EML4-ALK-v2 | CTAACTCGGGAGACTATGAAATATTGTACTTGTACCGCCGGAAGCACCAG | 178 |
| EML4-ALK-v3a | CAAGCATAAAGATGICATCATCAACCAAGTGTACCGCCGGAAGCACCAGG | 179 |
| EML4-ALK-v3b-3 | TCAACTCGCGAAAAAAACAGCCAAGTGTACCGCCGGAAGCACCAGGAGCT | 180 |
| EML4-ALK-v4 | CATGATCTGAATCCTGAAAGAGAAATAGAGATATGCTGGATGAGCCCTGA | 181 |

TABLE 8-continued

EML-ALK fusion probe target sequences

| Variant | Target Sequence (5'-> 3') | SEQ ID NO: |
|---|---|---|
| EML4-ALK-v5a | AAAATCAGTCTCAAGTAAAGTGTACCGCCGGAAGCACCAGGAGCTGCAAG | 182 |
| EML4-ALK-v5b-3 | CTCAAGTAAAGGTTCAGAGCTCAGGGGAGGATATGGAGATCCAGGGAGGC | 183 |
| EML4-ALK-v6 | AACAGCTCTCTGTGATGCGCTACTCAATAGTGTACCGCCGGAAGCACCAG | 184 |

An ARRAYPLATE (HTG Molecular) including programming linkers including a portion complementary to a portion of the fusion probe at spatially distinct locations was prepared by diluting 20× wash solution (20×SSC, 0.95% TWEEN-20, 0.05% KATHON) heated to 50° C. by 1:20, adding 250 µl per well to the ARRAYPLATE, incubating for 10-50 seconds and emptying the wells. This was repeated for six cycles. After the last wash, 40 µl of programming solution including 5 nM of each programming linker was added per well and the plate was incubated at 60° C. for 60-90 minutes and then washed.

A Stop plate was prepared with 10 µl S1 stop solution (1.6 N NaOH, 0.135 M EDTA, pH 8.0) and the entire sample was transferred to the stop plate following nuclease incubation. The stop plate was incubated at 95° C. for 15-20 minutes to inactivate the S1 nuclease and hydrolyze bound RNA. The plate was allowed to cool at room temperature for 5-10 minutes and 10 µl neutralization solution (1 M HEPES, pH 7.5, 6×SSC, 1.6 N HCl) was added to the lower aqueous phase of the Stop Plate and mixed.

The wash solution was removed from the ARRAYPLATE and 60 µl of the lower aqueous phase was transferred from the Stop plate to the ARRAYPLATE. The remaining 70 µl of the upper oil phase of the Stop plate was transferred to the ARRAYPLATE and the plate was incubated at 50° C. for 16-24 hours to allow probe hybridization to the plate. The ARRAYPLATE was then washed with wash solution and 40 µl of detection linker solution (5 nM) was added and incubated for 60-90 minutes at 60° C. to allow detection linker hybridization. Following washing, 40 µl of detection probe (5 nM) was added to the plate and incubated for 60-90 minutes at 50° C. Following washing, 40 µl of detection enzyme solution was added to the plate and incubated at 37° C. for 60 minutes. The plate was washed and incubated at room temperature with shaking for 15-30 minutes. After washing, 50 µl of luminescent solution was added and overlaid with 100 µl of imaging oil (99.9% Norpar 15, 0.1% Oil Red O Dye) and imaged using an OMIX, OMIX HD, CAPELLA, or SUPERCAPELLA imager.

Titration curves with increasing amount of IVT fusion mRNA were performed with each EML4-ALK probe. The results for each probe are shown in FIG. 6A-H. All probes provided sensitive detection of IVT mRNA. The EML4-ALK-v2 (FIG. 6B), EML4-ALK-v3a (FIG. 6C), EML4-ALK-v4 (FIG. 6E), and EML4-ALK-v5a (FIG. 6F) probes all exhibited a linear response over the titration curve. The observed differences in signal intensities may be due to differences in efficiency of hybridization of the probes to their target fusion sequence, the quality of the IVTs, or other factors.

Example 4

ALK Flanking Probes

This example describes design and testing of 5' and 3' flanking ALK probes.

Two IVT mRNAs were utilized in these experiments. One was a full-length ALK IVT generated from a commercially available clone. The second IVT was designed to include only the 16 target sequences (Table 9). Experiments were carried out as described in Example 3.

TABLE 9

ALK 5' and 3' flanking probe target sequences

| Target ID | Target position | Target sequence (5'-> 3') | SEQ ID NO: |
|---|---|---|---|
| ALK 5' target 1 | 56 | GCGGTGGTAGCAGCTGGTACCTCCCGCCGCCTCTGTTCGGAGGGTCGCGG | 185 |
| ALK 5' target 2 | 262 | GAGCCGAGGCGCCGGTGAGAGCAAGGACGCTGCAAACTTGCGCAGCGCGG | 186 |
| ALK 5' target 3 | 337 | CAGCAGGCAGACAGTCCGAAGCCTTCCCGCAGCGGAGAGATAGCTTGAGG | 187 |
| ALK 5' target 4 | 595 | CCAACTGCCACCTCCCTTCAACCATAGTAGTTCCTCTGTACCGAGCGCAG | 188 |
| ALK 5' target 5 | 1086 | GCTACTCGCGCCTGCAGAGGAAGAGTCTGGCAGTTGACTTCGTGGTGCCC | 189 |

TABLE 9-continued

ALK 5' and 3' flanking probe target sequences

| Target ID | Target position | Target sequence (5'-> 3') | SEQ ID NO: |
|---|---|---|---|
| ALK 5' target 6 | 1349 | CGCAAGCTCCGGCGTGCCAAGCAGTTGGTGCTGGAGCTGGGC GAGGAGGC | 190 |
| ALK 5' target 7 | 1445 | CTGCTCCAGTTCAATCTCAGCGAGCTGTTCAGTTGGTGGATT CGCCAAGG | 191 |
| ALK 5' target 8 | 1528 | GAAGAAGGCGTCGGAAGTGGGCAGAGAGGGAAGGCTGTCCGC GGCAATTC | 192 |
| ALK 3' target 1 | 4233 | CCAACTACTGCTTTGCTGGCAAGACCTCCTCCATCAGTGACC TGAAGGAG | 193 |
| ALK 3' target 2 | 4578 | GAGAGACCCGCCCTCGCCCGAGCCAGCCCTCCTCCCTGGCCA TGCTGGAC | 194 |
| ALK 3' target 3 | 4723 | GACCTGTCCAGGCCCTGGAAGAGTGGCCAAGATTGGAGACTT CGGGATGG | 195 |
| ALK 3' target 4 | 5125 | TGTAATCAACACCGCTTTGCCGATAGAATATGGTCCACTTGT GGAAGAGG | 196 |
| ALK 3' target 5 | 5394 | CTCAGTCCAACCCTCCTTCGGAGTTGCACAAGGTCCACGGAT CCAGAAAC | 197 |
| ALK 3' target 6 | 5557 | GGAGGGAAGCTGTACTGTCCCACCTAACGTTGCAACTGGGAG ACTTCCGG | 198 |
| ALK 3' target 7 | 5611 | CTCACTGCTCCTAGAGCCCTCTTCGCTGACTGCCAATATGAA GGAGGTAC | 199 |
| ALK 3' target 8 | 5665 | GTTCAGGCTACGTCACTTCCCTTGTGGGAATGTCAATTACGG CTACCAGC | 200 |

Eight different target sequences in the 5' portion of the ALK gene that is not involved in the EML fusion construct were selected and probes were designed. Eight different target sequences in the 3' portion of the ALK gene which are part of the EML fusion construct were also selected and probes were designed. Each probe was tested against the full-length ALK IVT (FIG. 7A) and the truncated ALK IVT (FIG. 7B). Based on these results, the following target sequences were selected for detection of ALK gene fusions: ALK 5' target 3, ALK 5' target 5, ALK 5' target 7, ALK 5' target 8, ALK 3' target 5, ALK 3' target 6, ALK 3' target 7, and ALK 3' target 8.

Example 5

Methods of Detecting a Gene Fusion Utilizing Flanking Probe Ratios

This example describes exemplary methods of detecting the presence of a gene fusion in a sample utilizing probes flanking the fusion region. However, one skilled in the art will appreciate that methods that deviate from these specific methods can also be used to successfully detect the presence of a gene fusion in a sample.

A sample, such as a tumor sample or a blood sample is collected from a subject having or suspected to have a target gene fusion. Cells in the sample are lysed with lysis buffer (described above) at 60° C. for 6-16 hours in the presence of a 5' flanking probe and a 3' flanking probe for one of the genes in the target gene fusion (for example, flanking probes shown in Table 3 or Table 8). The mixture is treated with S1 nuclease (1:40 dilution in S1 nuclease buffer) at 50° C. for 60-90 minutes to digest unhybridized RNA and probes. The nuclease reaction is stopped (1.6 N NaOH, 0.135 M EDTA pH 8.0) for 15-20 minutes at 95° C. and then the mixture is added to a plate including programming linkers specific for the flanking probes and incubated at 50° C. for 16-24 hours. Detection linkers are then added and incubated at 60° C. for 60-90 minutes. Detection probe is added and incubated at 50° C. for 60-90 minutes, then detection solution is added and incubated at 37° C. for 60 minutes. Luminescent solution is added and the plate is imaged to detect fusion probe binding to the plate.

A ratio of the signal intensity of the 5' flanking probe to the 3' flanking probe is calculated. If the ratio is not statistically different from one, then the target gene fusion is not present in the sample. If the flanking probes are complementary to the 5' gene in the target gene fusion, then the gene fusion is present in the sample if the ratio is statistically significantly greater than one. If the flanking probes are complementary to the 3' gene in the target gene fusion, then the gene fusion is present in the sample if the ratio is statistically significantly less than one.

Example 6

Microarray Method of Detecting Gene Fusions

This example describes exemplary methods of detecting a gene fusion in a sample that include utilizing a microarray. However, one skilled in the art will appreciate that methods that deviate from these specific methods can also be used to successfully detect the presence of a gene fusion in a sample.

Lysis buffer, mineral oil (to prevent evaporation) and 167 pM final concentration of one or more fusion probes and/or flanking probes are added to a sample including cells. The sample is heated at 95° C. for 10-15 minutes and then incubated at 60° C. for 6-16 hours for RNA-probe hybridization. If the sample is FFPE tissue or cells, the sample is treated with 1 mg/ml proteinase K at 50° C. prior to incubation at 60° C. S1 nuclease is diluted 1:40 in S1 nuclease buffer (0.25 M sodium acetate, pH 4.5, 1.4 M NaCl, 0.225 M ZnSO$_4$, 0.05% KATHON) and added to the sample. The sample is incubated at 50° C. for 60-90 minutes to digest unbound nucleic acids.

An ARRAYPLATE (HTG Molecular) including programming linkers including a portion complementary to a portion of the fusion probe at spatially distinct locations is prepared by diluting 20× wash solution (20×SSC, 0.95% TWEEN-20, 0.05% KATHON) heated to 50° C. by 1:20, adding 250 µl per well to the ARRAYPLATE, incubating for 10-50 seconds and emptying the wells. This is repeated for six cycles. After the last wash, 40 µl of programming solution including 5 nM of each programming linker is added per well and the plate is incubated at 60° C. for 60-90 minutes and then washed.

A Stop plate is prepared with 10 µl S1 stop solution (1.6 N NaOH, 0.135 M EDTA, pH 8.0) and the entire sample (120 µl) is transferred to the stop plate following nuclease incubation. The stop plate is incubated at 95° C. for 15-20 minutes to inactivate the S1 nuclease and hydrolyze bound RNA. The plate is allowed to cool at room temperature for 5-10 minutes and 10 µl neutralization solution (1 M HEPES, pH 7.5, 6×SSC, 1.6 N HCl) is added to the lower aqueous phase of the Stop Plate and mixed.

The wash solution is removed from the ARRAYPLATE and 60 µl of the lower aqueous phase is transferred from the Stop plate to the ARRAYPLATE. The remaining 70 µl of the upper oil phase of the Stop plate is transferred to the ARRAYPLATE and the plate is incubated at 50° C. for 16-24 hours to allow probe hybridization to the plate. The ARRAYPLATE is then wash with wash solution and 40 µl of detection linker solution (5 nM) is added and incubated for 60-90 minutes at 60° C. to allow detection linker hybridization. Following washing, 40 of detection probe (5 nM) is added to the plate and incubated for 60-90 minutes at 50° C. Following washing, 40 µl of detection enzyme solution is added to the plate and incubated at 37° C. for 60 minutes. The plate is washed and incubated at room temperature with shaking for 15-30 minutes. After washing, 50 µl of luminescent solution is added and overlaid with 100 µl of imaging oil (99.9% Norpar 15, 0.1% Oil Red O Dye) and imaged using an OMIX, OMIX HD, CAPELLA, or SUPER-CAPELLA imager. Signal intensity indicates presence and amount of fusion probe hybridization, indicating presence of the target gene fusion (if a fusion probe is used), or presence of full length and/or gene (if flanking probes are used).

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of detecting presence of a gene fusion in a sample from a subject comprising:
   contacting the sample with one or more first probes complementary to a first nucleic acid from a first gene, wherein the one or more first probes are linear nucleic acids and complementary to the first nucleic acid 5' to a fusion point between the first nucleic acid and a second nucleic acid from a second gene, under conditions sufficient for the one or more first probes to specifically hybridize to the first nucleic acid, wherein the sample comprises cell lysate or isolated nucleic acids, and wherein the first nucleic acid and the second nucleic acid are mRNA;
   contacting the sample with one or more second probes complementary to the first nucleic acid, wherein the one or more second probes are linear nucleic acids and complementary to the first nucleic acid 3' to the fusion point between the first nucleic acid and the second nucleic acid, under conditions sufficient for the one or more second probes to specifically hybridize to the first nucleic acid;
   wherein the one or more first probes comprise the nucleic acid sequence of any one of SEQ ID NOs: 187, 189, 191, or 192 or the complement thereof, the one or more second probes comprise the nucleic acid sequence of any one of SEQ ID NOs: 197-200 or the complement thereof, or a combination of two or more thereof;
   contacting the sample with a nuclease specific for single-stranded nucleic acids;
   detecting an amount of the one or more first probes and an amount of the one or more second probes in the sample;
   determining a ratio consisting of the amount of the one or more first probes to the amount of the one or more second probes in the sample; and
   detecting the presence of the gene fusion if the ratio of the one or more first probes to the one or more second probes is significantly different from a control by at least two standard deviations.

2. The method of claim 1, further comprising determining that the gene fusion does not comprise a 3' portion of the first nucleic acid if the ratio of the one or more first probes to the one or more second probes is greater than a control by at least two standard deviations or determining that the gene fusion does not comprise a 5' portion of the first nucleic acid if the ratio of the one or more first probes to the one or more second probes is less than a control by at least two standard deviations.

3. The method of claim 1, wherein the one or more first probes and the one or more second probes are each 50-200 nucleotides in length.

4. The method of claim 1, wherein detecting the one or more first probes and the one or more second probes comprises contacting the sample with one or more first detection probes which are capable of hybridizing with the one or more first probes and one or more second detection probes which are capable of hybridizing with the one or more second probes.

5. The method of claim 1, further comprising:
   contacting the sample with a fusion probe comprising a 5' portion complementary to the first nucleic acid and a 3' portion complementary to the second nucleic acid under conditions sufficient for the probe to specifically hybridize to the gene fusion, wherein the fusion probe spans a fusion point of the first nucleic acid and the second nucleic acid, prior to contacting the sample with the nuclease;
   detecting an amount of the fusion probe;
   determining a ratio consisting of the amount of the fusion probe to the amount of the one or more first probes in the sample, thereby determining a percentage of the gene fusion in the sample relative to the first nucleic acid or determining a ratio consisting of the amount of the fusion probe to the amount of the one or more second probes in the sample, thereby determining a percentage of the gene fusion in the sample relative to the second nucleic acid.

6. The method of claim 5, wherein the fusion probe is about 10 to 200 nucleotides in length.

7. The method of claim 1, wherein the one or more first probes and the one or more second probes each further comprise a detectable label.

8. The method of claim 7, wherein the one or more first probes and the one or more second probes each comprise a different detectable label or wherein the one or more first probes and the one or more second probes each comprise the same detectable label.

9. The method of claim 1, wherein the cell lysate or isolated nucleic acid sample is obtained from tissue, a tumor biopsy, blood, or a bodily fluid.

10. The method of claim 1, wherein:
    contacting the sample with one or more first probes comprises contacting the sample with two or more first probes complementary to the first nucleic acid 5' to a fusion point between the first nucleic acid and the second nucleic acid; and
    contacting the sample with one or more second probes comprises contacting the sample with two or more second probes complementary to the first nucleic acid 3' to the fusion point between the first nucleic acid and the second nucleic acid.

11. The method of claim 10, further comprising:
    contacting the sample with one or more third probes complementary to a third nucleic acid from a third gene, wherein the one or more third probes are complementary to the third nucleic acid 5' to a fusion point between the third nucleic acid and a fourth nucleic acid from a fourth gene, under conditions sufficient for the one or more third probes to specifically hybridize to the third nucleic acid; and
    contacting the sample with one or more fourth probes complementary to the third nucleic acid, wherein the one or more fourth probes are complementary to the third nucleic acid 3' to the fusion point between the third nucleic acid and the fourth nucleic acid, under conditions sufficient for the one or more fourth probes to specifically hybridize to the third nucleic acid;
    detecting an amount of the one or more third probes and an amount of the one or more fourth probes in the sample;
    determining a ratio consisting of the amount of the one or more third probes to the amount of the one or more fourth probes in the sample; and
    detecting the presence of a gene fusion between the third and fourth genes if the ratio of the one or more third probes to the one or more fourth probes is significantly different from a control by at least two standard deviations.

12. The method of claim 11, wherein:
    contacting the sample with one or more third probes comprises contacting the sample with two or more third probes complementary to the third nucleic acid 5' to a fusion point between the third nucleic acid and the fourth nucleic acid; and contacting the sample with one or more fourth probes
contacting the sample with two or more fourth probes
complementary to the third nucleic acid 3' to the fusion
point between the third nucleic acid and the fourth
nucleic acid.

13. The method of claim 1, further comprising:
contacting the sample with one or more third probes
complementary to a third nucleic acid from a third
gene, wherein the one or more third probes are complementary to the third nucleic acid 5' to a fusion point
between the third nucleic acid and a fourth nucleic acid
from a fourth gene, under conditions sufficient for the
one or more third probes to specifically hybridize to the
third nucleic acid;
contacting the sample with one or more fourth probes
complementary to the third nucleic acid, wherein the
one or more fourth probes are complementary to the
third nucleic acid 3' to the fusion point between the
third nucleic acid and the fourth nucleic acid, under
conditions sufficient for the one or more fourth probes
to specifically hybridize to the third nucleic acid;
detecting an amount of the one or more third probes and
an amount of the one or more fourth probes in the
sample;
determining a ratio consisting of the amount of the one or
more third probes to the amount of the one or more
fourth probes in the sample; and
detecting the presence of a gene fusion between the third
and fourth genes if the ratio of the one or more third
probes to the one or more fourth probes is significantly
different from a control by at least two standard deviations.

14. The method of claim 13, wherein:
contacting the sample with one or more third probes
comprises contacting the sample with two or more third
probes complementary to the third nucleic acid 5' to a
fusion point between the third nucleic acid and the
fourth nucleic acid; and
contacting the sample with one or more fourth probes
comprises contacting the sample with two or more
fourth probes complementary to the third nucleic acid
3' to the fusion point between the third nucleic acid and
the fourth nucleic acid.

15. The method of claim 1, wherein the one or more first probes and the one or more second probes are DNA.

16. A method of detecting presence of a gene fusion in a sample from a subject, comprising:
contacting the sample with one or more first probes
complementary to a first nucleic acid from a first gene,
wherein the one or more first probes are linear nucleic
acids 50-200 nucleotides in length and complementary
to the first nucleic acid 5' to a fusion point between the
first nucleic acid and a second nucleic acid from a
second gene, under conditions sufficient for the one or
more first probes to specifically hybridize to the first
nucleic acid, wherein the sample comprises cell lysate
or isolated nucleic acids, and wherein the first nucleic
acid and the second nucleic acid are mRNA;
contacting the sample with one or more second probes
complementary to the first nucleic acid, wherein the
one or more second probes are linear nucleic acids
50-200 nucleotides in length and complementary to the
first nucleic acid 3' to the fusion point between the first
nucleic acid and the second nucleic acid, under conditions sufficient for the one or more second probes to
specifically hybridize to the first nucleic acid;
wherein the one or more first probes comprise the nucleic
acid sequence of any one of SEQ ID NOs: 187, 189, 191, or
192 or the complement thereof, the one or more second
probes comprise the nucleic acid sequence of any one of
SEQ ID NOs: 197-200 or the complement thereof, or a
combination of two or more thereof;
contacting the sample with a nuclease specific for single-stranded nucleic acids;
detecting an amount of the one or more first probes and an
amount of the one or more second probes in the sample;
determining a ratio consisting of the amount of the one or
more first probes to the amount of the one or more
second probes in the sample; and
detecting the presence of the gene fusion if the ratio of the
one or more first probes to the one or more second
probes is significantly different from a control by at
least two standard deviations.

17. A high-throughput method of detecting presence of gene fusions in multiple samples from one or more subjects, comprising:
contacting two or more samples contemporaneously with
one or more first probes complementary to a first
nucleic acid from a first gene, wherein the one or more
first probes are linear nucleic acids 50-200 nucleotides
in length and complementary to the first nucleic acid 5'
to a fusion point between the first nucleic acid and a
second nucleic acid from a second gene, under conditions sufficient for the one or more first probes to
specifically hybridize to the first nucleic acid, wherein
the two or more samples comprise cell lysate or isolated nucleic acids, and wherein the first nucleic acid
and the second nucleic acid are mRNA;
contacting the two or more samples contemporaneously
with one or more second probes complementary to the
first nucleic acid, wherein the one or more second
probes are linear nucleic acids 50-200 nucleotides in
length and complementary to the first nucleic acid 3' to
the fusion point between the first nucleic acid and the
second nucleic acid, under conditions sufficient for the
one or more second probes to specifically hybridize to
the first nucleic acid; wherein the one or more first
probes comprise the nucleic acid sequence of any one
of SEQ ID NOs: 187, 189, 191, or 192 or the complement thereof, the one or more second probes comprise
the nucleic acid sequence of any one of SEQ ID NOs:
197-200 or the complement thereof, or a combination
of two or more thereof;
contacting the two or more samples contemporaneously
with a nuclease specific for single-stranded nucleic
acids;
detecting an amount of the one or more first probes and an
amount of the one or more second probes in the two or
more samples contemporaneously;
determining a ratio consisting of the amount of the one or
more first probes to the amount of the one or more
second probes in the two or more samples contemporaneously; and
detecting the presence of the gene fusion if the ratio of the
one or more first probes to the one or more second
probes is significantly different from a control by at
least two standard deviations.

18. The method of claim 17, further comprising:
contacting the two or more samples contemporaneously
with one or more third probes complementary to a third
nucleic acid from a third gene, wherein the one or more
third probes are linear nucleic acids 10 to 200 nucleotides in length and complementary to the third nucleic acid 5' to a fusion point between the third nucleic acid and a fourth nucleic acid from a fourth gene, under conditions sufficient for the one or more third probes to specifically hybridize to the third nucleic acid;

contacting the two or more samples contemporaneously with one or more fourth probes complementary to the third nucleic acid, wherein the one or more fourth probes are linear nucleic acids 10 to 200 nucleotides in length and complementary to the third nucleic acid 3' to the fusion point between the third nucleic acid and the fourth nucleic acid, under conditions sufficient for the one or more fourth probes to specifically hybridize to the third nucleic acid;

detecting an amount of the one or more third probes and an amount of the one or more fourth probes in the two or more samples contemporaneously;

determining a ratio consisting of the amount of the one or more third probes to the amount of the one or more fourth probes in the two or more samples contemporaneously; and detecting the presence of a gene fusion between the third and fourth genes if the ratio of the one or more third probes to the one or more fourth probes is significantly different from a control by at least two standard deviations.

19. The method of claim 17, wherein at least 10 different gene fusions are detected.

* * * * *

SEQUENCE LISTING

```
<160> NUMBER OF SEQ ID NOS: 200

<210> SEQ ID NO 1
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 1
gggaccgagg gtcatgcttt cagaacg                                        27

<210> SEQ ID NO 2
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 2
gcctggagat ctcattgttt gtgc                                           24

<210> SEQ ID NO 3
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 3
gaaatgcttc ttgcttcacc cttagc                                         26

<210> SEQ ID NO 4
<211> LENGTH: 29
<212> TYPE: DNA
```

```
<213> ORGANISM: Artificial Sequence
<220> FEATURE:
<223> OTHER INFORMATION: Synthetic oligonucleotide

<400> SEQUENCE: 4
ctaaacttgg caccaagtat gagatatag                                      29

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
gccgcgcggc tccagggttc c                                              21

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 6
gcgagcccct tgcagctgag gatt                                           24

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 7
cgagcccctt gcagctgagg attt                                           24

<210> SEQ ID NO 8
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 8
gagccccttg cagctgagga tttg                                           24

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 9
agccccttgc agctgaggat ttgt                                           24

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
gccccttgca gctgaggatt tgtg                                           24
```

```
<210> SEQ ID NO 11
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 11
ccccttgcag ctgaggattt gtga                                              24

<210> SEQ ID NO 12
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 12
cccttgcagc tgaggatttg tgac                                              24

<210> SEQ ID NO 13
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 13
cgagcccctt gcagtcctgg tacc                                              24

<210> SEQ ID NO 14
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 14
gagccccttg cagtcctggt acct                                              24

<210> SEQ ID NO 15
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 15
agccccttgc agtcctggta cctg                                              24

<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 16
gccccttgca gtcctggtac ctgg                                              24

<210> SEQ ID NO 17
<211> LENGTH: 24
<212> TYPE: DNA
<213> ORGANISM: Artificial Sequence
<220> FEATURE:
```

<223> OTHER INFORMATION: Synthetic oligonucleotide

<400> SEQUENCE: 17
ccccttgcag tcctggtacc tggg                                              24

<210> SEQ ID NO 18
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 18
gcgagcccct tgcagcctaa cggc                                              24

<210> SEQ ID NO 19
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 19 cgagccccatt gcagcctaac ggca                                             24

<210> SEQ ID NO 20
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 20
gagccccttg cagcctaacg gcag                                              24

<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 21
agccccttgc agcctaacgg cagt                                              24

<210> SEQ ID NO 22
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 22
gccccttgca gcctaacggc agtg                                              24

<210> SEQ ID NO 23
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 23
ccccttgcag cctaacggca gtgg                                              24

```
<210> SEQ ID NO 24
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 24
tggagcgcgg caggttattc cagg                                              24

<210> SEQ ID NO 25
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 25
ggagcgcggc aggttattcc agga                                              24

<210> SEQ ID NO 26
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 26
gagcgcggca ggttattcca ggat                                              24

<210> SEQ ID NO 27
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 27
ttgaactcag tctcggcccc cgct                                              24

<210> SEQ ID NO 28
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 28
tgaactcagt ctcggccccc gctt                                              24

<210> SEQ ID NO 29
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 29
gaactcagtc tcggcccccg cttg                                              24

<210> SEQ ID NO 30
<211> LENGTH: 24
<212> TYPE: DNA
<213> ORGANISM: Artificial Sequence
<220> FEATURE:
<223> OTHER INFORMATION: Synthetic oligonucleotide
```

<400> SEQUENCE: 30
tacgggcagc agaacccttc ttat                                          24

<210> SEQ ID NO 31
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 31
acgggcagca gaacccttct tatg                                          24

<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 32
cgggcagcag aaccttctt atga                                           24

<210> SEQ ID NO 33
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 33
atagagcggc tcccagcgtt ccctgcggcg taggaggcgg tccagactat              50

<210> SEQ ID NO 34
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 34
gcggccggca cctcattcat ttctaccggt ctctagtagt gcagcttcgg              50

<210> SEQ ID NO 35
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 35
caaggcttcg ccgtcatcga ggccatttcc agcgacttgt cgcacgcttt              50

<210> SEQ ID NO 36
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 36
gtgctggcac caactcggga actggcccaa caggtgcagc aagtagctgc              50

<210> SEQ ID NO 37
<211> LENGTH: 50

<212> TYPE: DNA
<213> ORGANISM: Artificial Sequence
<220> FEATURE:
<223> OTHER INFORMATION: Synthetic oligonucleotide

<400> SEQUENCE: 37
caatctgaga agaacaacct accttgtcct tgatgaagca gatagaatgc                50

<210> SEQ ID NO 38
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 38
gcaattaatc ccaagttgct tcagttggtc gaagacagag gttcaggtcg                50

<210> SEQ ID NO 39
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 39
gtcacattct cctgccctgg cgctgacaag ggtccagcct ccgatgaccc                50

<210> SEQ ID NO 40
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 40
gtgacacctg catgatgaat gtgcacaagc gctgcgtgat gaatgttccc                50

<210> SEQ ID NO 41
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 41
ccgcatctac atccaggccc acatcgacag ggacgtcctc attgtcctcg                50

<210> SEQ ID NO 42
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 42
gaaagacaag aggcttgcaa ggaccctgaa gaggtcggag catcatacag                50

<210> SEQ ID NO 43
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 43
ctcatgagat ggtatcagcc acccaatgac tggcgtatct tggtcctgtg                50

<210> SEQ ID NO 44
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 44
gagagacacc tccaacttcg acaaagagtt caccagacag cctgtggaac                50

<210> SEQ ID NO 45
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 45
ctttcagttg ctttgctgtt agcctgttgg accttcgagc ctagctgctc                50

<210> SEQ ID NO 46
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 46
cacaggactc ggccacctgc ccttcctgca ccgactggcc agctcaaga                 49

<210> SEQ ID NO 47
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 47
gtctgggatg ggagccacag gcaccttgag gacctccctg gacccaagcc                50

<210> SEQ ID NO 48
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 48
ggaggcaggt cgggaggaag aagaggtgga ggtgtggttg tggtggagag                50

<210> SEQ ID NO 49
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 49
cctgcctgga ccctgttggt ggctgaagac ctctggccag ctggcttccg                50

<210> SEQ ID NO 50
<211> LENGTH: 50
<212> TYPE: DNA
<213> ORGANISM: Artificial Sequence

```
<220> FEATURE:
<223> OTHER INFORMATION: Synthetic oligonucleotide

<400> SEQUENCE: 50
cagcagaact aggttctgag ccacgggtca gggtgccacc ctgctgctgg          50

<210> SEQ ID NO 51
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 51
caagctggcc gaggttgcag tccatgagct gggaaaggag gcagtgctct          50

<210> SEQ ID NO 52
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 52
ttgggagaaa cagcagaggc ctcaagtttc gggctgaagc aacagagtc           50

<210> SEQ ID NO 53
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 53
gtttcgggct gaagccaaca gagtcccaac cagtgggcgt atcccaagat          50

<210> SEQ ID NO 54
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 54
ctgcagccac tcagtagtct tctgtggtca cagaagtaaa cattgttggc          50

<210> SEQ ID NO 55
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 55
gcaggcttac caatttccat agtctcatga ggccgaaatg aattacaatg          50

<210> SEQ ID NO 56
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 56
ccactaggga atctccagat gaactattaa tgcactgtct tatgcctctc          50
```

<210> SEQ ID NO 57
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 57
tttatgacgg gcccggtgct gaagggcagg gaacaacttg atggtgctac                50

<210> SEQ ID NO 58
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 58
gaaggaggat gttcccatct tggtcagtcc tatgcggata gagatgtctg                50

<210> SEQ ID NO 59
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 59
gccagaacca tgccaaatat gtgtctgtga ctcaggatcc gttctctgcg                50

<210> SEQ ID NO 60
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 60
caagggtgaa agtgggaaac caggagctaa cggtctcagt ggagaacgtg                50

<210> SEQ ID NO 61
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 61
gtccttgatg tgcagctggc attccttcga cttctctcca gccgagcttc                50

<210> SEQ ID NO 62
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 62
caccctatga cattggtggt cctgatcaag aatttggtgt ggacgttggc                50

<210> SEQ ID NO 63
<211> LENGTH: 50
<212> TYPE: DNA
<213> ORGANISM: Artificial Sequence
<220> FEATURE:
<223> OTHER INFORMATION: Synthetic oligonucleotide
<210> SEQ ID NO 64
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 64
ctttctcatt cgagctcaag gactgccctg gtcatgcact atggaagatg          50

<210> SEQ ID NO 65
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 65
tgcagaaagc cttagagaag caccgcatgt acatgggcca gcggtatgtg          50

<210> SEQ ID NO 66
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 66
tttagcctag ctgctgctta cggagtgcaa gggagaactc tgagaagcag          50

<210> SEQ ID NO 67
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 67
gagccatgac tgttgctgca ctccagcctg agtgacagag tgagaccctg          50

<210> SEQ ID NO 68
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 68
gagatggagt cttgtatcgc ccaggctaga gtgcagtggc ctggtcttgg          50

<210> SEQ ID NO 69
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 69
gctggctctg ctgctctcgc gatatttgcg cgagcctgct tccttctttc          50

<210> SEQ ID NO 70

<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 70
ctgctctcgc gatatttgcg cgagcctgct tccttctttc ctcccttgcc     50

<210> SEQ ID NO 71
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 71
tatttgcgcg agcctgcttc cttctttcct cccttgccag tccgcctgtc     50

<210> SEQ ID NO 72
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 72
gactacctgc cgaggatctt gtgattctgg agaactaggc cgaaactcag     50

<210> SEQ ID NO 73
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 73
atcttgcctc tccaccctta gtggtagctt atgccatagc aggcacagtg     50

<210> SEQ ID NO 74
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 74
ggttccctcc acatatgaag atggaccatg gcaggataca actgattgtg     50

<210> SEQ ID NO 75
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 75
gtgttgtcga cttgacctgc taatttcctg ttctggaatc gagagaagac     50

<210> SEQ ID NO 76
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 76
ctccagggtt caacccttg gctggtgcag gaaagcaaac accacaagcc 50

<210> SEQ ID NO 77
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 77
ggtattcgac ctgcacgagt tgtatcttca acttctgagg aggaggaagc 50

<210> SEQ ID NO 78
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 78
ctgttataca tgtgacagtg actttgtgct gaaatttcag ctattccaga 50

<210> SEQ ID NO 79
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 79
tttgttctta cagaaagtgt tgattgccag gttgcttata gcactttaag 50

<210> SEQ ID NO 80
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 80
cttcggtctt ccacagcagt attattgtct tgtggagtt gactaatgat 50

<210> SEQ ID NO 81
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 81
gaggtggcgg cgagaagatg gcgacttcga acaatccgcg gaaattcagc 50

<210> SEQ ID NO 82
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 82
ggcgagaaga tggcgacttc gaacaatccg cggaaattca gcgagaagat 50

<210> SEQ ID NO 83
<211> LENGTH: 50
<212> TYPE: DNA

<213> ORGANISM: Artificial Sequence
<220> FEATURE:
<223> OTHER INFORMATION: Synthetic oligonucleotide

<400> SEQUENCE: 83
tggcgacttc gaacaatccg cggaaattca gcgagaagat cgcgctgcac    50

<210> SEQ ID NO 84
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 84
gctcccatca ccttcactgg gtcccgatgg agccgtctca gaggccgagg    50

<210> SEQ ID NO 85
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 85
ccaagtgtcc tgttccctgc ggcccttggc cttccagggt cctggccagg    50

<210> SEQ ID NO 86
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 86
ggtgctggct ctgatgattc cagagcctgt atccaccttc tgggctcctg    50

<210> SEQ ID NO 87
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 87
ctccctctcc tatcggagca caatgaaagc ctgtgtatcg ccgtgactcc    50

<210> SEQ ID NO 88
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 88
cagacttgcc tgcaatagcc agcagtagcc tctttccacc tcaccatccc    50

<210> SEQ ID NO 89
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 89
caccacctga gctgtgaagg acgatatgaa cgaggtaggg ccgagagctc    50

<210> SEQ ID NO 90
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 90
caacaaactc cttaatttgc tctaatagat aggtatggtt taatctttcc          50

<210> SEQ ID NO 91
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 91
cttgcaggat agattgaaat gttataggtt tgtttggagt aaccaaacag          50

<210> SEQ ID NO 92
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 92
tttcccacaa tcctctactt cagtgggatg ctgtgtctag tgattaaaca          50

<210> SEQ ID NO 93
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 93
ctcctccgtg acctcctcct cctctttctc ctgagaaact tcgccccagc          50

<210> SEQ ID NO 94
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 94
cccggcacag catatatagc agtgacgagg atgatgagga ctttgagatg          50

<210> SEQ ID NO 95
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 95
tgtgtgacca tgactatgat gggctgcttc ccaagtctgg aaagcgtcac          50

<210> SEQ ID NO 96
<211> LENGTH: 50
<212> TYPE: DNA
<213> ORGANISM: Artificial Sequence
<220> FEATURE:

<223> OTHER INFORMATION: Synthetic oligonucleotide

<400> SEQUENCE: 96
gggagacaga aactgtggtt gatagccagt cactgcctta agaacatttg         50

<210> SEQ ID NO 97
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 97
gatagccagt cactgcctta agaacatttg atgcaagatg gccagcactg         50

<210> SEQ ID NO 98
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 98
agccagtcac tgccttaaga acatttgatg caagatggcc agcactgaac         50

<210> SEQ ID NO 99
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 99
gcacgccgag tgaacttgaa tctttggcta tttaaggagg actgggtttg         50

<210> SEQ ID NO 100
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 100
cattcatcga ggcacttctt ccacatgtcc gtgcaattgc ctatacttgg         50

<210> SEQ ID NO 101
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 101
ccttgccaaa ctgcgcaaag atattcgcca ggagtatcga gaggactttg         50

<210> SEQ ID NO 102
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 102
gcatcagcca aactcattgc catgacaact ctttgtactg tgtccgtgcc         50

<210> SEQ ID NO 103
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 103
gtacaactgt aggtgacgag tagtcagtta ttgcttgcta gctacacacc            50

<210> SEQ ID NO 104
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 104
cagcctatac tgctagcagc tgctcatact gcagtcaatt actggaagcg            50

<210> SEQ ID NO 105
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 105
cagcggacgg aaccattcca aacagcctag tctcgtgctg agagcctctc            50

<210> SEQ ID NO 106
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 106
gtgtcacgtc gggcgctctt tagagaggac tgggacaaga gttgcggacg            50

<210> SEQ ID NO 107
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 107
ggcgagcacc gtcaggagcg cagagatcgg ccctactaga tgcagagacc            50

<210> SEQ ID NO 108
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 108
tgtgagcatg ctcagtatca ttgtggagaa ccaagagggc ctcttaactg            50

<210> SEQ ID NO 109
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 109
gtatcattgt ggagaaccaa gagggcctct taactgtaac aatgttcatg         50

<210> SEQ ID NO 110
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 110
gtttcatccg gttaactgtc tctttcgctc cgctacaaca caaacgtgc         50

<210> SEQ ID NO 111
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 111
gggactatta aggaggctct gtcggtggtg agcgacgacc agtccctctt         50

<210> SEQ ID NO 112
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 112
gcaggagtgg atcaatcagc cagtgagggt caacgtcaag cgggagtatg         50

<210> SEQ ID NO 113
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 113
cttcttaggg taacactaag taccttctag acaacatgtc tacctaaatg         50

<210> SEQ ID NO 114
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 114
gggtaacact aagtaccttc tagacaacat gtctacctaa atgaaatggg         50

<210> SEQ ID NO 115
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 115
caacatgtct acctaaatga aatgggatgt gtttcggaac atttgtctcc         50

<210> SEQ ID NO 116
<211> LENGTH: 50

<212> TYPE: DNA
<213> ORGANISM: Artificial Sequence
<220> FEATURE:
<223> OTHER INFORMATION: Synthetic oligonucleotide

<400> SEQUENCE: 116
gagtaggcgc gagctaagca ggaggcggag gcggaggcgg agggcgaggg        50

<210> SEQ ID NO 117
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 117
gcgcggcagg tcatattgaa cattccagat acctatcatt actcgatgct        50

<210> SEQ ID NO 118
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 118
cactactcta ccatggttct gcctcctggc caagcaggct ggtttgcaag        50

<210> SEQ ID NO 119
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 119
gaatgattct acagctagga cttaaccttg aaatggaaag tcatgcaatc        50

<210> SEQ ID NO 120
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 120
ctgtagagag cagcattccc agggaccttg gaaacagttg gcactgtaag        50

<210> SEQ ID NO 121
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 121
ccggccgtgc ggccggaggg agcggccgga tggagcggag gatgaaagcc        50

<210> SEQ ID NO 122
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 122
ggatgaaagc cggatacttg gaccagcaag tgccctacac cttcagcagc                50

<210> SEQ ID NO 123
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 123
ccttcagcag caaatcgccc ggaaatggga gcttgcgcga agcgctgatc                50

<210> SEQ ID NO 124
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 124
ctttcttctg ccctttccta ggcccaggcc tgggtttgta cttccacctc                50

<210> SEQ ID NO 125
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 125
ctaggcccag gcctgggttt gtacttccac ctccaccaca tctgccagac                50

<210> SEQ ID NO 126
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 126
gggtttgtac ttccacctcc accacatctg ccagacctta ataaaggccc                50

<210> SEQ ID NO 127
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 127
gggagagtgt gcaagagatc gctgcgggac aggttcctag agatcgctcc                50

<210> SEQ ID NO 128
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 128
cccgagggac atgagagaag aggagcggcg ctcaggttat tccaggatct                50

<210> SEQ ID NO 129
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 129
gagcggcgct caggttattc caggatcttt ggagacccga ggaaagccgt    50

<210> SEQ ID NO 130
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 130
gcactgtggc ttgggattca ctagccctga gcctgatgtt gctggctatc    50

<210> SEQ ID NO 131
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 131
ccttctgcac agatgtggca cctgcaaccc aggagcagga gccggaggag    50

<210> SEQ ID NO 132
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 132
cagcaggtgc agcagagatg gctacagctc aggagctggg aaggtgatgg    50

<210> SEQ ID NO 133
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 133
gatgctactg gccgctgaag ggcttctgcg tctccatgga aggcgccctc    50

<210> SEQ ID NO 134
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 134
tagcctaaga cccggagctt ttcacctgcg tctccatgga aggcgccctc    50

<210> SEQ ID NO 135
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 135
gatgctactg gccgctgaag ggcttttttc cagagagttc ttggtcgttg g    51

<210> SEQ ID NO 136
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 136
tagcctaaga cccggagctt ttcactttcc agagagttct tggtcgttgg           50

<210> SEQ ID NO 137
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 137
gatgctactg gccgctgaag ggcttacttc ttctgctgct cccggatgtt           50

<210> SEQ ID NO 138
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 138
tagcctaaga cccggagctt ttcacacttc ttctgctgct cccggatgtt           50

<210> SEQ ID NO 139
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 139
gatgctactg gccgctgaag ggcttcttcc ttagttgatg gtcagcggaa t         51

<210> SEQ ID NO 140
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 140
tagcctaaga cccggagctt ttcaccttcc ttagttgatg gtcagcggaa t         51

<210> SEQ ID NO 141
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 141
gatgctactg gccgctgaag ggcttttgaa ctctgcttaa atccagtggc           50

<210> SEQ ID NO 142
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 142
tagcctaaga cccggagctt ttcacttgaa ctctgcttaa atccagtggc         50

<210> SEQ ID NO 143
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 143
gatgctactg gccgctgaag ggctttgacg tcgaaggctg ccttcagtgc         50

<210> SEQ ID NO 144
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 144
tagcctaaga cccggagctt ttcactgacg tcgaaggctg ccttcagtgc         50

<210> SEQ ID NO 145
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 145
gatgctactg gccgctgaag ggcttcgatg ccctctgcga agttggggta         50

<210> SEQ ID NO 146
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 146
tagcctaaga cccggagctt ttcaccgatg ccctctgcga agttggggta         50

<210> SEQ ID NO 147
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 147
gcgctcccac aacgctcgac cggcggaggg cgccttccat ggagacgcag         50

<210> SEQ ID NO 148
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 148
gcgctcccac aacgctcgac cggcggaggg cgccttccat ggagacgcag         50

<210> SEQ ID NO 149

```
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 149
ggacgccgtc cggtcctcac gtggaccaac gaccaagaac tctctggaaa          50

<210> SEQ ID NO 150
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 150
ggacgccgtc cggtcctcac gtggaccaac gaccaagaac tctctggaaa          50

<210> SEQ ID NO 151
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 151
gcagcgcacg tgctcagccg tagtgaacat ccgggagcag cagaagaagt          50

<210> SEQ ID NO 152
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 152
gcagcgcacg tgctcagccg tagtgaacat ccgggagcag cagaagaagt          50

<210> SEQ ID NO 153
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 153
ccacgtccct tcctagagac gcttaattcc gctgaccatc aataaggaag          50

<210> SEQ ID NO 154
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 154
ccacgtccct tcctagagac gcttaattcc gctgaccatc aacaaggaag          50

<210> SEQ ID NO 155
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 155
```
tggctgtaga acacgcgagc ggttcgccac tggatttaag cagagttcaa            50

<210> SEQ ID NO 156
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 156
tggctgtaga acacgcgagc ggttcgccac tggatttaag cagagttcaa            50

<210> SEQ ID NO 157
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 157
ctggcagcca cggacgcgga acgaggcact gaaggcagcc ttcgacgtca            50

<210> SEQ ID NO 158
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 158
ctggcagcca cggacgcgga acgaggcact gaaggcagcc ttcgacgtca            50

<210> SEQ ID NO 159
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 159
gcggactgtg gtaccatgcc gaccgtaccc caacttcgca gagggcatcg            50

<210> SEQ ID NO 160
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 160
gcggactgtg gtaccatgcc gaccgtaccc caacttcgca gagggcatcg            50

<210> SEQ ID NO 161
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 161
aagcccttca gcggccagta gcatctgctc tccttcactg tttggaggtg            50

<210> SEQ ID NO 162
<211> LENGTH: 50
<212> TYPE: DNA

<213> ORGANISM: Artificial Sequence
<220> FEATURE:
<223> OTHER INFORMATION: Synthetic oligonucleotide

<400> SEQUENCE: 162
gtgaaaagct ccgggtctta ggctatgctc tccttcactg tttggaggtg    50

<210> SEQ ID NO 163
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 163
aagcccttca gcggccagta gcatctgctc tccttcactg tttggaggtg    50

<210> SEQ ID NO 164
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 164
gtgaaaagct ccgggtctta ggctatgctc tccttcactg tttggaggtg    50

<210> SEQ ID NO 165
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 165
aagcccttca gcggccagta gcatctgctc tccttcactg tttggaggtg    50

<210> SEQ ID NO 166
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 166
gtgaaaagct ccgggtctta ggctatgctc tccttcactg tttggaggtg    50

<210> SEQ ID NO 167
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 167
aagcccttca gcggccagta gcatctgctc tccttcactg tttggaggtg    50

<210> SEQ ID NO 168
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 168
gtgaaaagct ccgggtctta ggctatgctc tccttcactg tttggaggtg    50

```
<210> SEQ ID NO 169
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 169
aagcccttca gcggccagta gcatctgctc tccttcactg tttggaggtg            50

<210> SEQ ID NO 170
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 170
gtgaaaagct ccgggtctta ggctatgctc tccttcactg tttggaggtg            50

<210> SEQ ID NO 171
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 171
aagcccttca gcggccagta gcatctgctc tccttcactg tttggaggtg            50

<210> SEQ ID NO 172
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 172
gtgaaaagct ccgggtctta ggctatgctc tccttcactg tttggaggtg            50

<210> SEQ ID NO 173
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 173
aagcccttca gcggccagta gcatctgctc tccttcactg tttggaggtg            50

<210> SEQ ID NO 174
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 174
gtgaaaagct ccgggtctta ggctatgctc tccttcactg tttggaggtg            50

<210> SEQ ID NO 175
<211> LENGTH: 73
<212> TYPE: DNA
<213> ORGANISM: Artificial Sequence
<220> FEATURE:
```

<223> OTHER INFORMATION: Synthetic oligonucleotide

<400> SEQUENCE: 175
acgatggcga gggcgccttc catggagacg cagaagccct tcagcggcca gtagcatctg    60
actttgagcc tca                                                       73

<210> SEQ ID NO 176
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 176
gcagaagccc ttcagcggcc agtagcatct gactttgagc ctca                     44

<210> SEQ ID NO 177
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 177
tagagcccac acctgggaaa ggacctaaag tgtaccgccg gaagcaccag                50

<210> SEQ ID NO 178
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 178
ctaactcggg agactatgaa atattgtact tgtaccgccg gaagcaccag                50

<210> SEQ ID NO 179
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 179
caagcataaa gatgtcatca tcaaccaagt gtaccgccgg aagcaccagg                50

<210> SEQ ID NO 180
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 180
tcaactcgcg aaaaaaacag ccaagtgtac cgccggaagc accaggagct                50

<210> SEQ ID NO 181
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 181
catgatctga atcctgaaag agaaatagag atatgctgga tgagccctga                50

<210> SEQ ID NO 182
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 182
aaaatcagtc tcaagtaaag tgtaccgccg gaagcaccag gagctgcaag    50

<210> SEQ ID NO 183
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 183
ctcaagtaaa ggttcagagc tcagggagg atatggagat ccagggaggc    50

<210> SEQ ID NO 184
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 184
aacagctctc tgtgatgcgc tactcaatag tgtaccgccg gaagcaccag    50

<210> SEQ ID NO 185
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 185
gcggtggtag cagctggtac ctcccgccgc ctctgttcgg agggtcgcgg    50

<210> SEQ ID NO 186
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 186
gagccgaggc gccggtgaga gcaaggacgc tgcaaacttg cgcagcgcgg    50

<210> SEQ ID NO 187
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 187
cagcaggcag acagtccgaa gccttcccgc agcggagaga tagcttgagg    50

<210> SEQ ID NO 188
<211> LENGTH: 50
<212> TYPE: DNA
<213> ORGANISM: Artificial Sequence
<220> FEATURE:

<223> OTHER INFORMATION: Synthetic oligonucleotide

<400> SEQUENCE: 188
ccaactgcca cctcccttca accatagtag ttcctctgta ccgagcgcag            50

<210> SEQ ID NO 189
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 189
gctactcgcg cctgcagagg aagagtctgg cagttgactt cgtggtgccc            50

<210> SEQ ID NO 190
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 190
cgcaagctcc ggcgtgccaa gcagttggtg ctggagctgg gcgaggaggc            50

<210> SEQ ID NO 191
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 191
ctgctccagt tcaatctcag cgagctgttc agttggtgga ttcgccaagg            50

<210> SEQ ID NO 192
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 192
gaagaaggcg tcggaagtgg gcagagaggg aaggctgtcc gcggcaattc            50

<210> SEQ ID NO 193
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 193
ccaactactg ctttgctggc aagacctcct ccatcagtga cctgaaggag            50

<210> SEQ ID NO 194
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 194
gagagacccg ccctcgcccg agccagccct cctccctggc catgctggac            50

```
<210> SEQ ID NO 195
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 195
gacctgtcca ggccctggaa gagtggccaa gattggagac ttcgggatgg          50

<210> SEQ ID NO 196
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 196
tgtaatcaac accgctttgc cgatagaata tggtccactt gtggaagagg          50

<210> SEQ ID NO 197
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 197
ctcagtccaa ccctccttcg gagttgcaca aggtccacgg atccagaaac          50

<210> SEQ ID NO 198
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 198
ggagggaagc tgtactgtcc cacctaacgt tgcaactggg agacttccgg          50

<210> SEQ ID NO 199
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 199
ctcactgctc ctagagccct cttcgctgac tgccaatatg aaggaggtac          50

<210> SEQ ID NO 200
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 200
gttcaggcta cgtcacttcc cttgtgggaa tgtcaattac ggctaccagc          50
```